United States Patent
Boland et al.

(10) Patent No.: US 10,529,446 B2
(45) Date of Patent: Jan. 7, 2020

(54) CONTINUOUS HEALTH CARE PLAN COORDINATION BETWEEN PATIENT AND PATIENT CARE TEAM

(71) Applicant: International Business Machines Corporation, Armonk, NY (US)

(72) Inventors: Gregory F. Boland, Katonah, NY (US); Kristina M. Brimijoin, Hastings on Hudson, NY (US); Atul Kumar, Irving, TX (US); Avraham Leff, Spring Valley, NY (US); Yu Ma, White Plains, NY (US); Russell G. Olsen, Flower Mound, TX (US); James T. Rayfield, Ridgefield, CT (US); Katherine Vogt, New York, NY (US); Justin D. Weisz, Stamford, CT (US)

(73) Assignee: International Business Machines Corporation, Armonk, NY (US)

( * ) Notice: Subject to any disclaimer, the term of this patent is extended or adjusted under 35 U.S.C. 154(b) by 398 days.

(21) Appl. No.: 15/387,760

(22) Filed: Dec. 22, 2016

(65) Prior Publication Data
US 2018/0181721 A1 Jun. 28, 2018

(51) Int. Cl.
*G16H 10/60* (2018.01)
*G16H 80/00* (2018.01)
(Continued)

(52) U.S. Cl.
CPC ............. *G16H 10/60* (2018.01); *G16H 40/67* (2018.01); *G16H 80/00* (2018.01); *G16H 20/10* (2018.01);
(Continued)

(58) Field of Classification Search
CPC ........ G16H 10/60; G16H 20/10; G16H 20/30; G16H 20/60; G16H 80/00
See application file for complete search history.

(56) References Cited

U.S. PATENT DOCUMENTS

| | | |
|---|---|---|
| 6,699,195 B2 | 3/2004 | Nakazawa et al. |
| 7,315,825 B2 | 1/2008 | Rosenfeld et al. |

(Continued)

OTHER PUBLICATIONS

List of IBM Patents or Patent Applications Treated as Related, Sep. 13, 2017, 2 pages.
(Continued)

*Primary Examiner* — Gregory H Curran
(74) *Attorney, Agent, or Firm* — Stephen J. Walder, Jr.; Ryan G. Lewis

(57) ABSTRACT

Mechanisms are provided for implementing a personalized health care management system. The mechanisms receive a personalized health care plan for a patient having at least one health goal of the patient, and dynamic patient monitoring data from one or more patient monitoring devices associated with the patient. The mechanisms analyze the dynamic patient monitoring data to determine at least one first communication to output to the patient containing content eliciting conformance of the patient with the personalized health care plan to achieve the at least one health goal. The mechanisms send, to a patient care manager computing device of a patient care manager associated with the patient, a second communication based on results of analyzing the dynamic patient monitoring data. The second communication initiates a new communication session, or continues an existing communication session, between the patient care manager computing device and a patient communication device associated with the patient.

20 Claims, 19 Drawing Sheets

(51) Int. Cl.
*G16H 40/67* (2018.01)
*G16H 20/30* (2018.01)
*G16H 20/60* (2018.01)
*G16H 20/10* (2018.01)
*H04L 29/08* (2006.01)

(52) U.S. Cl.
CPC .............. *G16H 20/30* (2018.01); *G16H 20/60* (2018.01); *H04L 67/12* (2013.01)

(56) References Cited

U.S. PATENT DOCUMENTS

| | | | |
|---|---|---|---|
| 7,743,340 | B2 | 6/2010 | Horvitz et al. |
| 7,967,749 | B2 | 6/2011 | Hutchinson et al. |
| 7,996,240 | B2 | 8/2011 | Canda |
| 8,374,988 | B2 | 2/2013 | Gawlick |
| 8,417,662 | B2 | 4/2013 | Gawlick |
| 8,428,632 | B2 | 4/2013 | Ye et al. |
| 8,489,428 | B2 | 7/2013 | Brown |
| 8,554,195 | B2 | 10/2013 | Rao |
| 8,847,767 | B2 | 9/2014 | Lim et al. |
| 8,880,454 | B2 | 11/2014 | Christie, IV et al. |
| 8,930,223 | B2 | 1/2015 | Friedlander et al. |
| 8,949,082 | B2 | 2/2015 | Farooq et al. |
| 8,996,428 | B2 | 3/2015 | Baras et al. |
| 9,015,054 | B2 | 4/2015 | Lara et al. |
| 9,113,776 | B2 | 8/2015 | Connor |
| 9,250,104 | B2 | 2/2016 | Greiner et al. |
| 9,298,882 | B2 | 3/2016 | Proud |
| 10,176,300 | B1* | 1/2019 | South ................ G16H 40/67 |
| 2004/0171918 | A1 | 9/2004 | Suzuki et al. |
| 2011/0202490 | A1 | 8/2011 | Gawlick |
| 2012/0004924 | A1 | 1/2012 | Kachnowski et al. |
| 2012/0209650 | A1* | 8/2012 | Romagnino ........... G06Q 10/06 705/7.15 |
| 2013/0179176 | A1 | 7/2013 | Gotthardt |
| 2013/0197369 | A1 | 8/2013 | Xiang |
| 2013/0223606 | A1 | 8/2013 | Lee |
| 2013/0246512 | A1 | 9/2013 | Lawler et al. |
| 2013/0267795 | A1 | 10/2013 | Cosentino et al. |
| 2013/0311193 | A1 | 11/2013 | Know et al. |
| 2014/0025393 | A1 | 1/2014 | Wang et al. |
| 2014/0114142 | A1 | 4/2014 | Shaoulian |
| 2014/0129249 | A1 | 5/2014 | Nkoy et al. |
| 2014/0278544 | A1 | 9/2014 | Khurana et al. |
| 2014/0297301 | A1 | 10/2014 | Rock |
| 2014/0348318 | A1 | 11/2014 | Talapady et al. |
| 2015/0009045 | A1 | 1/2015 | Proud |
| 2015/0127385 | A1 | 5/2015 | Pecora |
| 2015/0297904 | A1 | 10/2015 | Kavounas |
| 2015/0359966 | A1 | 12/2015 | Day et al. |

OTHER PUBLICATIONS

"Patient Registration System", Kramer Technologies, http://www.kramergroup.com/patient-registration-system.html; accessed from the Internet on Aug. 30, 2016, 1 page.

"System, Method and Apparatus for Providing Per-contact Status Information within an Instant-messaging System", An IP.com Prior Art Database Technical Disclosure, Anonymous, http://IP.com/IPCOM/000215762D, Mar. 11, 2012, 5 pages.

IBM, "Application of a single moveable input box to allow concise realtime instant multi-threaded messaging", An IP.com Prior Art Database Technical Disclosure, IBM, http://IP.com/IPCOM/000193027D, Feb. 8, 2010, 8 pages.

Kosir, Spela, "Wearables in Healthcare", https://www.wearable-technologies.com/2015/04/wearables-in-healthcare/, Apr. 2015, 8 pages.

Mell, Peter et al., "The NIST Definition of Cloud Computing", National Institute of Standards and Technology, Information Technology Laboratory, Version 15, Oct. 7, 2009, 2 pages.

Wolman, Alec et al., "Using Trusted Sensors to Monitor Patients' Habits", Research.microsoft.com; healthsec-2010, Jan. 2010, 2 pages.

\* cited by examiner

CODE TABLE – POP DM-1 HEDIS

PHYTEL CODES | CONTRACT CODES | PROTOCOLS | ICD/CPT OPTIONS

STANDARD CODES:

| CODING SYSTEM | CODE | CODE DESCRIPTION | REASON | REQ. |
|---|---|---|---|---|
| 19 | 250 | DIABETES MELLITUS | HEDIS 2011 | PHYTEL |
| 19 | 250.0 | DIABETES MELLITUS W/O COMPLICATION | HEDIS 2011 | PHYTEL |
| 19 | 250.00 | DIABETES MELLITUS (NIDDM) | HEDIS 2011 | PHYTEL |
| 19 | 250.01 | DIABETES MELLITUS W/O COMPLICATION TYPE I (... | HEDIS 2011 | PHYTEL |
| 19 | 250.02 | DIABETES MELLITUS W/O COMPLICATION TYPE II (... | HEDIS 2011 | PHYTEL |
| 19 | 250.03 | DIABETES MELLITUS W/O COMPLICATION TYPE I (... | HEDIS 2011 | PHYTEL |
| 19 | 250.1 | DIABETES WITH KETOACIDOSIS | HEDIS 2011 | PHYTEL |
| 19 | 250.10 | DIABETES WITH KETOACIDOSIS TYPE II OR UNSPE... | HEDIS 2011 | PHYTEL |
| 19 | 250.11 | DIABETES WITH KETOACIDOSIS TYPE I (JUVENILE... | HEDIS 2011 | PHYTEL |
| 19 | 250.12 | DIABETES WITH KETOACIDOSIS TYPE II OR UNSPE... | HEDIS 2011 | PHYTEL |
| 19 | 250.13 | DIABETES WITH KETOACIDOSIS TYPE I (JUVENILE... | HEDIS 2011 | PHYTEL |
| 19 | 250.2 | DIABETES WITH HYPEROSMOLARITY | HEDIS 2011 | PHYTEL |
| 19 | 250.20 | DIABETES WITH HYPEROSMOLARITY TYPE II OR... | HEDIS 2011 | PHYTEL |
| 19 | 250.21 | DIABETES WITH HYPEROSMOLARITY TYPE I (JUVE... | HEDIS 2011 | PHYTEL |

IMPORT...

SAVE | SAVE & CLOSE | CANCEL

Diabetes - HEDIS

- Diabetes - HEDIS
  - All Of
    - Pts 18-75
  - Any Of
    - Two ICD/EM combinations
    - One ICD/EM combination
    - DM Problem
      - All Of
        - Diabetes Problem
      - Not Any Of
        - Secondary Diabetes
    - Any Of
      - Polycystic Ovaries
      - SIDM or GDM
    - Not Any Of
      - Diabetes ICD Rule Name: Diabetes - HEDIS
Short Name: pDM_HEDIS
Keywords:

Variables | Rule Criteria

CODE RULE

Title: Two ICE/EM combinations ☑ Child Rule Enabled
Code Table: Pop DM-1 INSIGHT Look Back | Set Variable Name | Multiple Instances (Combo – 2 Instances)

Are Multiple Instances/Codes Required?
○ No, single instance of code qualifies.
● Yes, requires at least [2] instances [1] days apart.

☑ Code must have a combo to qualify

Code Table
ENC-27

Add...

OK    CANCEL

Select Parent Rules

Rule Name

Diabetes HbA1C Poor Control (>9%)

Short Name sDM_A1C_UNC

Select at least one parent from available rules:

Available Parent Rules pDM_HEDIS
sDM_Health
sDM_A1C
sDM_Health_INVERSE

* At least one parent rule required

Available Sibling Rules sDM_A1C_C8
sDM_A1C_H

ALL of these (*)

AND ANY of these (*)

sDM_A1C_INVERSE
sDM_A1C_VH

AND NOT in any of these

OK    CANCEL

*FIG. 9D*

CONTINUOUS HEALTH CARE PLAN COORDINATION BETWEEN PATIENT AND PATIENT CARE TEAM

BACKGROUND

The present application relates generally to an improved data processing apparatus and method and more specifically to mechanisms for providing continuous health care plan coordination between a patient and the patient's care team member(s).

Monitoring patients with chronic illnesses, such as congestive heart failure, diabetes, and asthma represents one of the greatest challenges facing modern medicine. Patients with chronic illnesses require ongoing, follow-up treatment and care to properly manage their conditions. Unfortunately, a number of these patients do not receive ongoing treatment and care, receive treatment and care on a sporadic basis, or receive treatment and care which is not in accordance with recommended guidelines. Worse, patients often fail to do the basic simple day-to-day tasks that could prevent or reduce the frequency and magnitude of a catastrophic event such as a hospitalization. As a result, these patients often unnecessarily suffer from symptoms of their chronic illness which would have been minimized or prevented with proper ongoing treatment and care. Additionally, some of these patients may later require hospitalization, or in severe cases some of these patients may die, both of which may have been prevented if the patient was receiving the proper ongoing treatment and care.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, wherein the at least one memory comprises instructions which are executed by the at least one processor to configure the data processing system to implement a personalized health care management system that operates to perform the method. The method comprises receiving, by the personalized health care management system, a personalized health care plan for a patient, where the personalized health care plan comprises at least one health goal of the patient. The method comprises receiving, by the personalized health care management system, dynamic patient monitoring data from one or more patient monitoring devices associated with the patient. Furthermore, the method comprises analyzing, by the personalized health care management system, the dynamic patient monitoring data to determine at least one first communication to output to the patient containing content eliciting conformance of the patient with the personalized health care plan to achieve the at least one health goal. In addition, the method comprises sending, by the personalized health care management system, to a patient care manager computing device of a patient care manager associated with the patient, a second communication based on results of analyzing the dynamic patient monitoring data. The second communication initiates a new communication session, or continues an existing communication session, between the patient care manager computing device and a patient communication device associated with the patient, the second communication causing at least one of: the patient care manager computing device to automatically send a scripted communication corresponding to the at least one first communication to the patient communication device, or the patient care manager computing device to output instructions to the patient care manager to perform an ad hoc communication with the patient communication device based on the at least one first communication.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 9A-9D are diagrams illustrating example graphical user interfaces for rule generation in accordance with one illustrative embodiment;

DETAILED DESCRIPTION

Figure 1:
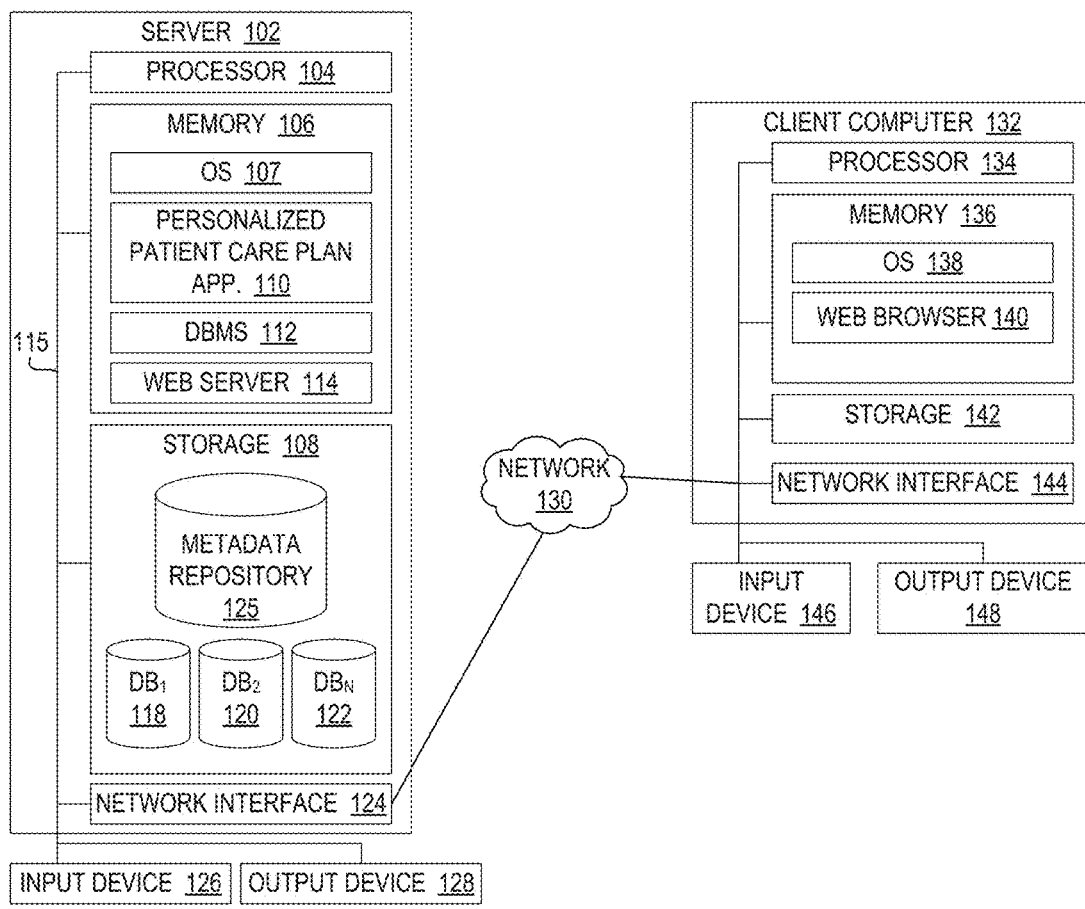
FIG. 1 is a block diagram illustrating a cloud computing system 100 for providing software as a service, where a server provides applications and stores data for multiple clients in databases according to one example embodiment of the invention.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In the following description, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

In addition, it should be appreciated that the present description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Overview

As noted above, providing treatment and care for patients having illness requiring ongoing treatment is a major issue in modern medicine. Many times this ongoing treatment and care is a shared responsibility between the medical workers, e.g., doctors, nurses, etc. and the patient. That is, the patient must perform certain actions on their own to provide self-treatment for the illness, which often involves making different lifestyle choices, e.g., changing diet, increasing physical activity, taking prescribed medications, eliminating habits and consumption of products that are detrimental to health, etc., with the medical workers providing monitoring and periodic checks of the patient's progress to ensure that the patient is adhering to the treatment needed to control and/or improve the patient's condition.

A number of mechanisms have been developed for assisting the patient and medical workers in handling their shared responsibilities including mechanisms for generating patient care plans based on the patient's medical condition, mechanisms for patient's to self-monitor their adherence to their own care plans, and the like. Such mechanisms often regard patients as generic types of patients, e.g., a generic asthma patient, a generic diabetes patient, etc. possibly with some classification within these generic categories based on the patient's age, gender, race, and other generic demographics. Even with such classification within the generic categories, the resulting care plan associated with the patient is one that is applicable to multiple patients having the same set of medical diagnosis and demographics. The care plan is not in fact personalized to the specific patient but to a general categorization of the patient.

Each individual patient has a specific and different set of lifestyle conditions that make that patient unique from other patients. It is this uniqueness that is not reflected in the patient care plans generated by known mechanisms.

That is, the known patient care plan mechanisms are created to classify patients into generic categories and apply generic care plans to these patients. While mechanisms employing such patient care plan mechanisms may refer to them as being "personalized" or "customized" to the patient, they in fact are only superficially customized in that they may be customized based on generic customization categories, e.g., customized based on generic demographics such as age, race, gender, etc. As a result, patients are not in fact presented with a patient care plan that the patient feels is specifically suited to them. The patient care plans do not in fact take into account the patient's own individual circumstances and can be applied to a plurality of patients having the same demographics and medical condition, e.g., all 40 year old female diabetes patients. There are no mechanisms that personalize a patient's on-going treatment and care based on both their medical condition and the patient's own personal lifestyle, taking into account multiple lifestyle conditions and the facilities and resources available to that particular patient based on their lifestyle.

It should be appreciated that the term "lifestyle" as it is used herein refers to the way in which a person lives their lives. The term "lifestyle information" refers to the data collected that characterizes the lifestyle of the patient and may encompass various temporal, spatial, environmental, and behavioral information/data about the patient that together comprises a unique combination of information/data that characterizes and represents the way in which that specific patient conducts their life on a daily basis. The lifestyle information for a patient is specific to that patient and is not generally applicable to multiple patients. The lifestyle information may be provided at various levels of granularity depending upon the particular implementation. As part of this lifestyle information, data generated by the specific patient via one or more computing devices or other data communication devices may be included such as actions performed by the patient on a daily basis, personal schedules, specifications of preferences, etc. For example, lifestyle information may include the patient entering information, such as into a computing device executing a patient tracking application, indicating that the patient ate breakfast at a fast food restaurant in the airport on the way to Virginia this morning. In addition, data generated by external systems associated with third parties that characterizes the patient's lifestyle may be included in the lifestyle information as well, e.g., a healthcare insurance company may have information about the patient's lifestyle, e.g., smoker, overweight, sedentary, high risk for diabetes, etc., which may be characteristic of the patient's lifestyle.

For example, with regard to temporal lifestyle information, the lifestyle information may comprise one or more data structures specifying one or more schedules of events that the patient undergoes either on a routine basis or on a dynamic basis, e.g., a baseline routine schedule that may be dynamically updated as events occur or do not occur. The temporal lifestyle information may comprise, for example, the time that the patient wakes in the morning, when they have their meals, when they go to work and return home, when they take their children to school, when they shop for groceries, when they go to bed at night, scheduled non-routine events, free time, scheduled flight, ferry, train, or other ground transportation departure/arrival times, and/or any other temporal information characteristic of the patient's daily life and other non-routine scheduled events.

With regard to spatial lifestyle information, this information may comprise one or more data structures identifying locations associated with the patient's daily lifestyle including routine locations frequented by the patient, e.g., the location of their home, the location of their work, the location of their child's school, the location of the retail establishments that they frequent, the location of their doctors, the typical travel paths between locations utilized by the patient, and the like. The spatial lifestyle information may further comprise information about each location including the number of stories or levels in the buildings, e.g., two-story home, five-story office building, etc., whether the location has stairs, etc. The spatial lifestyle information may further comprise geographic information including the city, state, county, country, etc., in which the patient lives, works, travels to, or otherwise conducts their life.

With regard to environmental lifestyle information, this information comprises one or more data structures with indications of the environmental quality and resource availability in the environments in which the patient is present, is predicted to be present at a later time (such as based on the temporal and spatial lifestyle information), or typically is present on a daily or routine basis. For example, environmental lifestyle information may include information about the patient's home location, e.g., in a rural, urban, or suburban environment, has access to parks, walking trails, etc. This environmental lifestyle information may include information about the patient's work location including whether the patient works in an office setting with fluorescent lights and relative quiet, in a manufacturing setting with heavy machinery and loud noises, works with computers the majority of the day, has his/her own office or is in a cubicle, the number of co-workers the patient has that they interface with on a daily basis, the types and/or identities of establishments around the patient's home/work for purposes of determining access to resources (e.g., products and services), air quality, weather conditions, elevation (for purposes of oxygen level determination, for example), and the like.

Regarding behavioral lifestyle information, this information comprises one or more data structures having indications of the patient's own behavior and likes/dislikes, i.e. lifestyle preferences. The behavioral lifestyle information may comprise such information as the patient's habits, responses to communications of different modalities, patterns of activity, and the like. For example, such behavioral lifestyle information may indicate that the patient has a habit of eating a snack every evening after 9 p.m. or takes his/her dog for a walk in the mornings before 9 a.m. and after 5 p.m. The behavioral lifestyle information may further indicate the patient's likes and dislikes (preferences) with regard to various elements of daily life including types of foods the patient likes/dislikes, types of physical activity the patient likes/dislikes, when the patient likes to engage in certain activities, e.g., exercising before work/after work, or the like.

The various lifestyle information data may be obtained directly from the patient, such as via an electronic questionnaire, through analysis of electronic medical records (EMRs) or other entries in databases associated with the patient (e.g., governmental databases associated with a patient's social security number, address, or the like), or otherwise obtained from one or more monitoring devices and/or applications utilized on one or more computing devices associated with the patient and with which the patient interacts, e.g., patient tracking applications on a smart phone, a medical monitoring device, or the like, that monitors physical activity, food logs, and the like. This lifestyle information may be generated from static information and may also be dynamically updated on a periodic or constant basis to obtain the most current lifestyle information representative of the patient's current lifestyle. The lifestyle information is utilized to customize or personalize a patient care plan for the specific patient such that the patient is presented with a resulting patient care plan that the patient feels is tailored specifically to them and the way they conduct their lives.

In addition to known patient care plan mechanisms suffering from the drawback of not in fact generating personalized patient care plans taking into account a patient's unique lifestyle, the known patient care plan mechanisms also do not provide for the ability to integrate third-party information about the lifestyle of a patient into the patient care plan personalization, such that a more complete understanding of the capabilities of the patient based on their lifestyle is realized when generating and monitoring the patient's adherence to the patient care plan. For example, third-party lifestyle information may comprise information from commercial and governmental computing systems, databases, and the like, that characterize the patient's environment, availability to resources (e.g., products/services/facilities), etc., or is otherwise ancillary and further defining of other lifestyle information associated with the patient.

As one example, a third-party lifestyle information source may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, specialty grocery stores, vitamin stores, pharmacies, restaurants, gyms, walking paths, parks, recreational areas, community pools, and the like, may be identified based on a GPS system and its associated databases of information. This information may include identifications of types (e.g., Vietnamese Restaurant) and specific identities of the particular establishments which can be used with other third-party lifestyle information sources (e.g., a particular restaurant's website comprising menu and nutrition information) to retrieve specific information about those identified establishments. For example, a particular restaurant may be determined to be within a specified distance of the patient's home location and corresponding restaurant menu item information and hours of operation information may be retrieved from that particular restaurant's website, computing system, or other database. The retrieved menu item information and hours of operation information may be used, as described hereafter, to correlate the information with patient care plan information, e.g., nutritional and caloric information may be correlated with the patient care plan, to generate patient care plan actions/tasks and/or recommendations for assisting the patient in adhering to the patient's personalized patient care plan. Similarly, other third-party lifestyle information sources may provide information for correlation with patient care plan actions/tasks including hours of operations, products/services provided, distance from the patient's locations, and the like.

The illustrative embodiments of the present invention collect patient demographic and medical data, such as from questionnaires, electronic medical records, and the like, and generate a baseline patient care plan based on an initial diagnosis of the patient's medical condition, one or more categorizations of the patient based on the collected demographic and medical data, established patient care plan guidelines, and goals to be achieved by the patient care plan. Thus, for example, a patient's demographic information and electronic medical records may indicate that the patient is a 40 year old female that has been diagnosed with diabetes. Various pre-established categories and sub-categories may be defined for different types of patients in an ontology based on the various demographic and medical history characteristics, e.g., a category for diabetes patients, a sub-category of patients in the age range of 40 to 50 years old, a sub-sub-category of female patients, and so on.

Similarly, treatment guidelines may be established for defining ways in which to treat various medical maladies with these treatment guidelines having various triggering patient characteristics. For example, a treatment guideline may specify that for female diabetes patients that are in the age range of 40 to 60 years old, the patient should follow a low sugar diet and have at least 30 minutes of stressful exercise per day. A database of such treatments and their guidelines may be provided that correlates various combinations of patient characteristics with a corresponding treatment. Thus, by categorizing the patient in accordance with their characteristic information as obtained from demographic and medical data for the patient, these categories may be used to evaluate the applicability of the various treatments by matching the categories with the patient characteristics of the treatments to identify the best treatment for the patient, i.e. the treatment having the most matches between the patient categories and the treatment's required patient characteristics.

At this point, a general patient care plan is generated for the patient that identifies the treatment, which may be an on-going treatment, which should be prescribed for the patient. A patient care plan in this context is essentially a set of goals and actions for achieving those goals. As will be described hereafter, in addition, the present invention includes, in a patient care plan, a patient monitoring plan with specific actions to be taken on the part of an assessor to monitor and interface with the patient to elicit positive results from the patient, e.g., adherence to the patient care plan.

While a general patient care plan is present at this point, the general patient care plan has not yet been personalized or customized to the specific patient's unique lifestyle information. That is, while in general a 40 year old female diabetes patient should follow a low sugar diet with 30 minutes of stressful exercise each day, not every patient's lifestyle will accommodate such actions in the same way.

The illustrative embodiments further operate to personalize the general patient care plan to the particular lifestyle of the specific patient. Lifestyle information data is obtained from various sources to obtain an overall representation of the lifestyle of the patient. Examples of such sources include geospatial information sources, weather information sources, commercial establishment websites or computing devices/databases, governmental or regulatory organization information sources, and the like.

A patient's lifestyle information may also include data gathered from social media sources, including social media posts, comments, likes, browsing and other activity by the patient to determine their social circle, hobbies, likes, dislikes, interests, etc. This may include, but is not limited to, data from websites like Facebook™, Twitter™, Instagram™, Reddit™, Pinterest™, blog posts, and the like.

Purchases and shopping activity are also a powerful indicators of lifestyle. Purchase data may include not only data about past purchases, but also shopping and activity online. Web browsing and search history, similar to that used in driving online advertising, can also be used to build lifestyle information and a lifestyle profile for a patient. Membership in customer loyalty programs from retail stores, grocery chains, and restaurants can also be used. Data that can be obtained from these programs may include membership, frequency of store visits, prior purchases, and the like. This data provides meaningful information about store, dining, grocery preferences, personal habits and schedules, and dietary data, among other information. This data may be used when building lifestyle information for the patient using products, goods, services, stores, and restaurants that the patient favors.

These third-party lifestyle information sources may provide lifestyle information that is combined with lifestyle information provided by the patient himself/herself for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan, e.g., prescribe a specific type of diet plan which the patient has access to foods that meet with the diet plan and has a schedule that facilitates preparation of particular types of food.

For example, if the patient has limited time due to long work hours, having young children that require attention in the mornings/evenings before/after work, and the like, then food preparation time will be determined to be a minimum and thus, a corresponding diet plan will be selected for this particular type of lifestyle involving more processed foods than another patient that may have more time to perform more complex food preparation actions. Similarly, based on the patient's lifestyle information as obtained from the various sources, the mechanisms of the illustrative embodiments may prescribe a walking regimen based on the fact that the patient lives near a walking trail (as obtained from GPS data) and works in a building that has multiple floors (as obtained from patient supplied lifestyle information, GPS data, and/or governmental real estate databases) such that walking the stairs is an option. The patient's lifestyle information may further indicate an ability to prescribe a strength-building regimen since the patient lives near a gym (obtained from GPS data) or has gym facilities at their office (obtained from the patient supplied lifestyle information and/or real estate database information listing amenities of the building where the patient works). The timing of such actions may be specified in the patient care plan such that the walking regimen may instruct the patient to take a 25 minute walk at 8 a.m. every weekday and walk up/down the stairs at their office on their way to and from work, and to and from lunch. The patient care plan may further specify that the patient is to go to the gym on Tuesday and Thursday at 7:30 p.m. to do 30 minutes of strength building exercise.

The granularity of the patient care plan may be even more specific depending upon the implementation. For example, with regard to a walking regimen, a particular path for the patient to walk may be specified in order to achieve a desired level of stress on the patient may be specified based on the geospatial information for the patient's home, work, and other locations, e.g., "Walk up Main Street to $2^{nd}$ Street, take a left, walk along $2^{nd}$ Street to Picard Street, take a left, walk down Picard Street to $1^{st}$ Street, take a left, and return to building." Such a path determination may be made based on information obtained about the geographical location of the patient's office building including the elevations of the streets to indicate uphill or downhill walking, distances, etc.

Because the lifestyle information may comprise specific establishment information, the patient care plan actions may be further personalized to the patient's particular locations and may specify particular establishments that can be frequented as well as what products/services the patient can utilize to be in compliance with the patient's prescribed care plan. For example, the menu items at a local restaurant may be analyzed to identify which menu items meet the diet requirements of the patient's care plan, e.g., low sugar foods, and the restaurant and its compliant menu items may be provided to the patient as part of their patient care plan. Personal trainer information for gyms may be obtained which includes the personal trainers' schedules, class schedules, and times of availability such that the patient may be instructed, as part of their personal patient care plan, when would be the best time for them to go to the gym to obtain personal trainer assistance with their strength building exercise regimen.

This more personalized patient care plan may further be customized to the specific lifestyle of the patient by evaluating the temporal lifestyle information and behavioral lifestyle information for the patient. Thus, having established a set of goals and actions to achieve those goals that are specific to the patient based on their demographics, medical data, and the patient's lifestyle information, the goals and actions may be converted to specific actions to be taken by the patient on a daily basis. For example, the patient's lifestyle information may be further analyzed to identify specific exercise actions to be taken by the patient based on their location, the facilities available, the patient's personal schedule of activities during the day, the patient's personal likes/dislikes (preferences), etc. For example, the patient may have a schedule that shows that the patient is available to exercise between 8 and 9 a.m. and 7:00 p.m. till 8:00 p.m. on most weekdays, is not available Thursday evenings after work for exercise, is available between 1 and 2 p.m. on Saturdays, and all day on Sundays. The preferences may further state that the patient does not like hot or rainy weather. The patient lifestyle information may further indicate that the patient likes to sleep late on Saturdays and Sundays and thus, while available early on these days, the mechanisms of the illustrative embodiments may adjust the scheduling of actions in the personalized care plan to accommodate this timing preference of the patient. Furthermore, the patient care plan may be dynamically adjusted based on determine weather and temperature conditions, e.g., instead of a standard walking regime that may have been previously part of the patient care plan, because the weather outside indicates a temperature of approximately 90 degrees and 20% chance of rain, the patient care plan may be adjusted to walking for 25 minutes in a neighborhood shopping mall.

It can be appreciated that because the lifestyle information that may be utilized to provide personalization of patient care plans is varied and vast, the types of personalizations that may be made to a patient care plan are likewise varied and vast. The patient care plan personalization mechanism of the illustrative embodiments provides logic for analyzing and evaluating a large set of lifestyle information data from various sources, determine specific patient care plan actions that meet the categorization and characterization of the patient's lifestyle as obtained from the analysis of the patient's lifestyle information, as well as achieves the goals and general actions associated with the generalized patient care plan corresponding to the patient's demographics and medical data, and compose the various personalized patient care plan actions into a series of actions to be taken by the patient over a set time period, e.g., daily, weekly, monthly, etc., in order to achieve desired goals of the patient care plan.

Thus, the illustrative embodiments provide various mechanisms for providing actual personalized patient care plans based not only on a categorization of the patient based on their medical diagnosis and demographic information, but also based on their own specific lifestyle information and lifestyle information obtained from third-party sources, e.g., information sources that provide information about a user's geographical surroundings, establishments in the user's geographical surroundings, event information sources, and the like. By personalizing the patient's care plan to their specific lifestyle, the likelihood that the patient will adhere to the care plan and perform the actions specified in the care plan is increased. Essentially, the personalized patient care plan helps to instruct the patient how the patient can integrate the care plan into their existing lifestyle without placing the burden on the patient to perform the analysis and evaluation on how to achieve such integration.

Having generated a personalized patient care plan taking into account the patient's personal lifestyle, the illustrative embodiments further provide mechanism for assisting and controlling the monitoring of a patient's adherence to the personalized care plan as well as assist health professionals, assessors, automated assessment systems, and the like, in performing actions and initiating communications to maintain ongoing treatment and care of the patient. Such mechanisms may involve evaluating the lifestyle information for the patient, the personalized care plan with its associated care plan actions, and determining appropriate monitoring actions/communications to be performed, timing of monitoring actions/communications, communication modes to be utilized, content of such communications, and the like, so as to maximize a positive response from the patient. Examples of such monitoring actions may be interrogating health monitoring devices and/or applications associated with the patient, e.g., wearable devices such as a FitBit™, pedometer, GPS device, applications running on a patient's smart phone or other computing device, or the like, initiating a reminder communication to be sent to the patient to remind them to perform an action in accordance with their personalized patient care plan, scheduling a doctor's appointment for the patient and informing them of the appointment, initiating a call to the patient's telephone to discuss their progress, or any other action that a human or automated assessment system may perform to assist with the monitoring of the patient's adherence to the patient's personalized patient care plan.

The particular monitoring actions to be employed are matched to the specific personalized patient care plan that is associated with the patient. That is, for each patient care plan action, there may be a set of one or more possible monitoring actions that may be associated with that type of patient care plan action. Selection from amongst the one or more possible monitoring actions may be performed based on an analysis of the patient's lifestyle information to determine the most appropriate monitoring action that will not interfere with the patient's lifestyle and will most likely result in a positive response from the patient. For example, if it is determined that the patient's lifestyle is such that the patient eats breakfast at 8:30 a.m. and one of the patient care plan actions is to eat oatmeal for breakfast three times a week, then a monitoring action may be selected that involves texting the patient with a message at 8:25 a.m., with the message having content that states "consider eating oatmeal for breakfast today." Other options may be to call the patient or send an electronic mail message but the patient's lifestyle information indicates that the patient is not a "morning person" and thus, is unlikely to respond well to calls in the morning and is generally in a rush to go to work since the patient eats breakfast at 8:30 a.m. and needs to be at the office by 9:30 a.m. indicating little time for checking electronic mail.

As with the personalized patient care plan, the monitoring plan and its monitoring actions, as well as their timing, may be personalized to the personalized patient care plan and the specific patient's lifestyle information. For example, if the patient works in a manufacturing environment where noise levels are high, it is unlikely that the patient will want to conduct a telephone conversation with a human assessor and is more likely to be responsive to textual communications. Thus, during working hours, monitoring actions may be restricted to textual communications, such as instant messaging or electronic mail. Similarly, if the patient works in a hospital, school, or other location where disturbances are to be minimized, communications may not be made during times of the day where the patient is likely to be present in such locations. Furthermore, as another example, if it is known that this particular patient weighs himself and takes his blood sugar measurements each morning at approximately 9:00 a.m., then a monitoring action may be to send a request to the electronic scale and/or blood sugar analysis mechanism to request the results of that day's measurements.

Thus, monitoring plans and corresponding monitoring actions are selected based on the patient's personalized patient care plan, the patient actions specified in the personalized patient care plan, and the lifestyle information for the particular patient. It should be appreciated that as the patient care plan changes over time, the monitoring plan also changes to match the changes to the patient care plan. Hence, in embodiments where the patient's personalized patient care plan is dynamically modified, such as in the case of dynamic changes based on weather, temperature, availability of facilities or resources, etc., the monitoring plan may likewise be dynamically modified.

Thus, in general, as can be seen from the above description and examples, the mechanisms of the illustrative embodiments combine information about a patient's medical condition, medical history, lifestyle information, geographical location(s), facilities located in these geographical locations(s), products and services available in these geographical location(s), desired goals of the care plan, and other lifestyle information, and personalizes the patient care plan to the patient's particular medical condition, particular lifestyle, and available facilities and resources to provide a specific personalized patient care plan for this specific patient that is not widely applicable to generalized categories of patients.

This information may further be used to personalize the assessment activities to be performed by the assessment system/personnel and influence the timing, communication modes, and monitoring actions performed. That is, based on the particular care plan goals and care plan actions that are part of the patient's care plan, these goals/actions may be paired with monitoring actions to be taken by an assessor, e.g., a medical professional, other individual whose duty it is to monitor and interface with patients to ensure that they are following a prescribed care plan, or automated system. The monitoring actions may likewise be personalized based on the patient's lifestyle information, geographical information, available products and services in the patient's geographical area(s) of interest (e.g., home, work, etc.), and the like. The assessment tasks may be automatically or semi-automatically performed so as to gather information for monitoring the patient's adherence to the personalized patient care plan and either automatically or semi-automatically adjust the personalized patient care plan accordingly, send notifications to the patient, notify the doctor, or perform some other desired actions for maximizing the probability that the patient will maintain adherence to the personalized patient care plan.

It should be appreciated that the personalized patient care plans, and the personalized patient care plan actions (patient actions performed by the patient and monitoring actions performed by the assessor), may be dynamically adjusted based on the patient's current environmental conditions, changes in schedule, determined deviations from the care plan, and other dynamic conditions that may interfere or otherwise require modification, either temporarily or permanently, of the patient's personalized patient care plan. As noted above, such factors as weather conditions, temperature conditions, resource availability (e.g., gym is closed), and the like may require temporary modifications to a patient's personalized patient care plan. Other factors, such as the patient moving to a new location, obtaining a new place of employment, or the like, may require more permanent modifications to the patient's personalized patient care plan. Such factors may be identified and corresponding modifications initiated taking into account the new temporary/permanent lifestyle changes of the patient.

In some illustrative embodiments, the analysis of the various patient information for generating of a personalized care plan, modification of personalized care plans, determining appropriate actions to perform, sending communications and selecting communication modes, and the like, may be performed utilizing a hierarchical system of clinical rules defined based on standardized guidelines from health care providers, health care payment providers, best practices determined by subject matter experts, e.g., physicians and other medical personnel, the general knowledge of subject matter experts, and the like. In some embodiments, the clinical rules may be generated based on natural language processing of natural language text defining these guidelines, best practices, and other knowledge of subject matter experts. A graphical user interface may be provided for facilitating creation of the clinical rules utilizing an object oriented engine user interface elements. The graphical user interface permits the creation of such clinical rules without having to have expert medical knowledge. The clinical rules may be applied to a patient registry comprising electronic medical records, demographics information, lifestyle information, and the like. Moreover, the clinical rules may be applied to patient information to determined care opportunities and what actions to be performed to improve the care provided to patients.

From the above general overview of the mechanisms of the illustrative embodiments, it is clear that the illustrative embodiments are implemented in a computing system environment and thus, the present invention may be implemented as a data processing system, a method implemented in a data processing system, and/or a computer program product that, when executed by one or more processors of one or more computing devices, causes the processor(s) to perform operations as described herein with regard to one or more of the illustrative embodiments. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in the figures, and described hereafter, one or more computing devices comprising a distributed data processing system, may be specifically configured to implement a personalized patient care plan system in accordance with one or more of the illustrative embodiments. The configuring of the computing device(s) may comprise the providing of application specific hardware, firmware, or the like to facilitate the performance of the operations and generation of the outputs described herein with regard to the illustrative embodiments. The configuring of the computing device(s) may also, or alternatively, comprise the providing of software applications stored in one or more storage devices and loaded into memory of a computing device for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of one or more of the illustrative embodiments and is not a general purpose computing device. Moreover, as described hereafter, the implementation of the mechanisms of the illustrative embodiments improves the functionality of the computing device(s) and provides a useful and concrete result that facilitates creation, monitoring, and adjusting personalized patient care plans based on personalized lifestyle information and assessment of patient adherence to the personalized patient care plan.

As mentioned above, the mechanisms of the illustrative embodiments may be implemented in many different types of data processing systems, both stand-alone and distributed. Some illustrative embodiments implement the mechanisms described herein in a cloud computing environment. It should be understood in advance that although a detailed description on cloud computing is included herein, implementation of the teachings recited herein are not limited to a cloud computing environment. Rather, embodiments of the present invention are capable of being implemented in conjunction with any other type of computing environment now known or later developed. For convenience, the Detailed Description includes the following definitions which have been derived from the "Draft NIST Working Definition of Cloud Computing" by Peter Mell and Tim Grance, dated Oct. 7, 2009.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics of a cloud model are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service models of a cloud model are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment models of a cloud model are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes. A node in a cloud computing network is a computing device, including, but not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. A cloud computing node is capable of being implemented and/or performing any of the functionality set forth hereinabove.

Personalized Care Plan Generation and Monitoring

FIG. 1 is a block diagram illustrating a cloud computing system 100 for providing software as a service, where a server provides applications and stores data for multiple clients in databases according to one example embodiment of the invention. The networked system 100 includes a server 102 and a client computer 132. The server 102 and client 132 are connected to each other via a network 130, and may be connected to other computers via the network 130. In general, the network 130 may be a telecommunications network and/or a wide area network (WAN). In a particular embodiment, the network 130 is the Internet.

The server 102 generally includes a processor 104 connected via a bus 115 to a memory 106, a network interface device 124, a storage 108, an input device 126, and an output device 128. The server 102 is generally under the control of an operating system 107. Examples of operating systems include UNIX, versions of the Microsoft Windows™ operating system, and distributions of the Linux™ operating system. More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single identity, it should be understood that the memory 106 may comprise a plurality of modules, and that the memory 106 may exist at multiple levels, from high speed registers and caches to lower speed but larger DRAM chips. The network interface device 124 may be any type of network communications device allowing the server 102 to communicate with other computers via the network 130.

The storage 108 may be a persistent storage device. Although the storage 108 is shown as a single unit, the storage 108 may be a combination of fixed and/or removable storage devices, such as fixed disc drives, solid state drives, floppy disc drives, tape drives, removable memory cards or optical storage. The memory 106 and the storage 108 may be part of one virtual address space spanning multiple primary and secondary storage devices.

As shown, the storage 108 of the server contains a plurality of databases. In this particular drawing, four databases are shown, although any number of databases may be stored in the storage 108 of server 102. Storage 108 is shown as containing databases numbered 118, 120, and 122, each corresponding to different types of patient related data, e.g., electronic medical records (EMRs) and demographic information, lifestyle information, treatment guidelines, personalized patient care plans, and the like, for facilitating the operations of the illustrative embodiments with regard to personalized patient care plan creation, monitoring, and modification. Storage 108 is also shown containing metadata repository 125, which stores identification information, pointers, system policies, and any other relevant information that describes the data stored in the various databases and facilitates processing and accessing the databases.

The input device 126 may be any device for providing input to the server 102. For example, a keyboard and/or a mouse may be used. The output device 128 may be any device for providing output to a user of the server 102. For example, the output device 108 may be any conventional display screen or set of speakers. Although shown separately from the input device 126, the output device 128 and input device 126 may be combined. For example, a display screen with an integrated touch-screen may be used.

As shown, the memory 106 of the server 102 includes a personalized patient care plan application 110 configured to provide a plurality of services to users via the network 130. As shown, the memory 106 of server 102 also contains a database management system (DBMS) 112 configured to manage a plurality of databases contained in the storage 108 of the server 102. The memory 106 of server 102 also contains a web server 114, which performs traditional web service functions, and may also provide application server functions (e.g. a J2EE application server) as runtime environments for different applications, such as the personalized patient care plan application 110.

As shown, client computer 132 contains a processor 134, memory 136, operating system 138, storage 142, network interface 144, input device 146, and output device 148, according to an embodiment of the invention. The description and functionality of these components is the same as the equivalent components described in reference to server 102. As shown, the memory 136 of client computer 132 also contains web browser 140, which is used to access services provided by server 102 in some embodiments. The client computer 132, in some illustrative embodiments, may be a mobile communication device in which computing capabilities are provided, e.g., a tablet computing device, a mobile smart phone, a laptop computing device, or the like.

The particular description in FIG. 1 is for illustrative purposes only and it should be understood that the invention is not limited to specific described embodiments, and any combination is contemplated to implement and practice the invention. Although FIG. 1 depicts a single server 102, embodiments of the invention contemplate any number of servers for providing the services and functionality described herein. Furthermore, although depicted together in server 102 in FIG. 1, the services and functions of the personalized patient care plan application 110 may be housed in separate physical servers, or separate virtual servers within the same server. The personalized patient care plan application 110, in some embodiments, may be deployed in multiple instances in a computing cluster. As is known to those of ordinary skill in the art, the modules performing their respective functions for the personalized patient care plan application 110 may be housed in the same server, on different servers, or any combination thereof. The items in storage, such as metadata repository 125, databases 118, 120, and 122, may also be stored in the same server, on different servers, or in any combination thereof, and may also reside on the same or different servers as the application modules.

Figure 2:
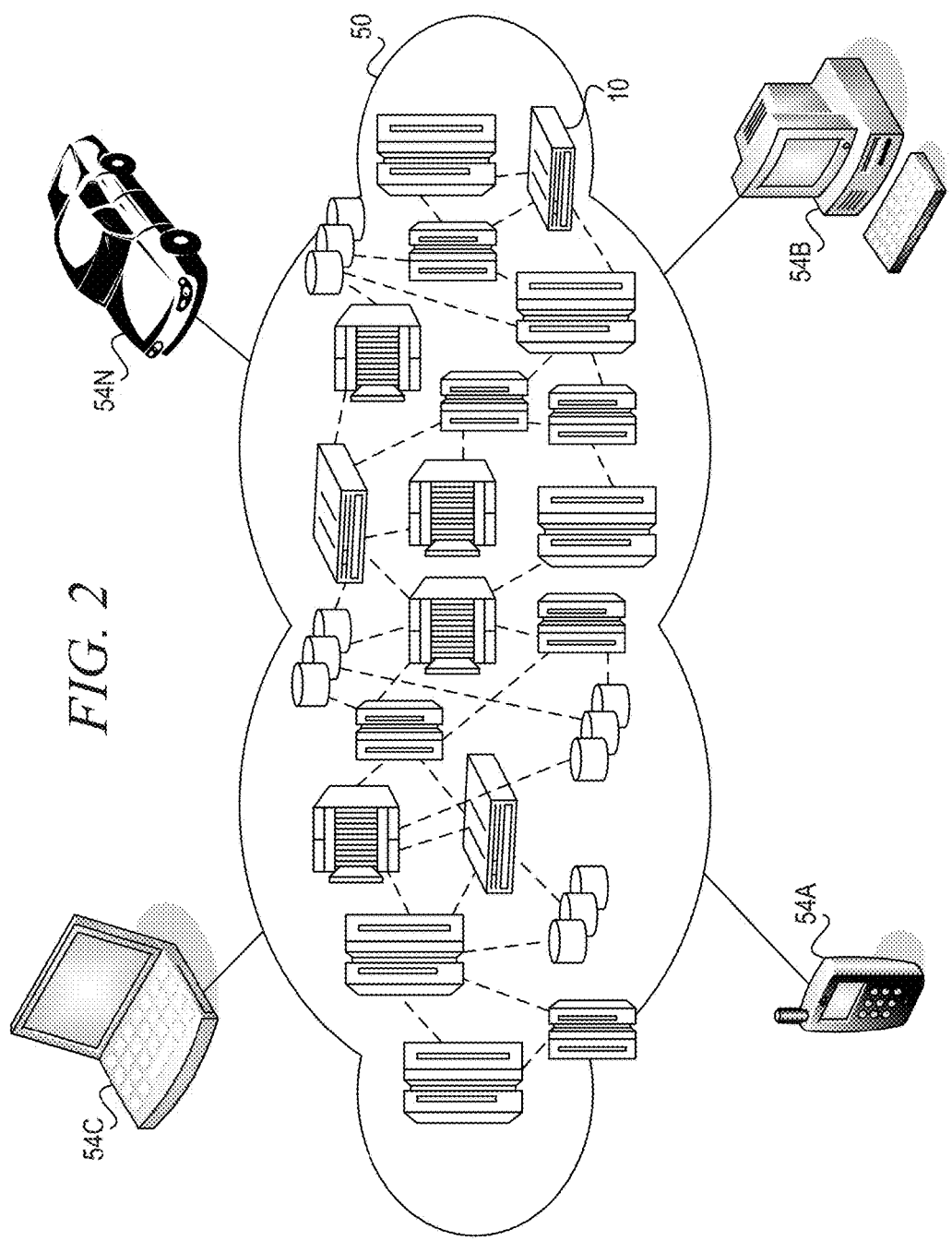
FIG. 2 is another perspective of an illustrative cloud computing environment in which aspects of the illustrative embodiments may be implemented.

Referring now to FIG. 2, another perspective of an illustrative cloud computing environment 250 is depicted. As shown, cloud computing environment 250 comprises one or more cloud computing nodes 210, which may include servers such as server 102 in FIG. 1, with which local computing devices used by cloud consumers, such as, for example, personal digital assistant (PDA) or cellular telephone 254A, desktop computer 254B, laptop computer 254D, and/or automobile computer system 254N may communicate. Nodes 210 may communicate with one another. A computing node 210 may have the same attributes as server 102 and client computer 132, each of which may be computing nodes 210 in a cloud computing environment. They may be grouped (not shown) physically or virtually, in one or more networks, such as Private, Community, Public, or Hybrid clouds as described hereinabove, or a combination thereof. This allows cloud computing environment 250 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
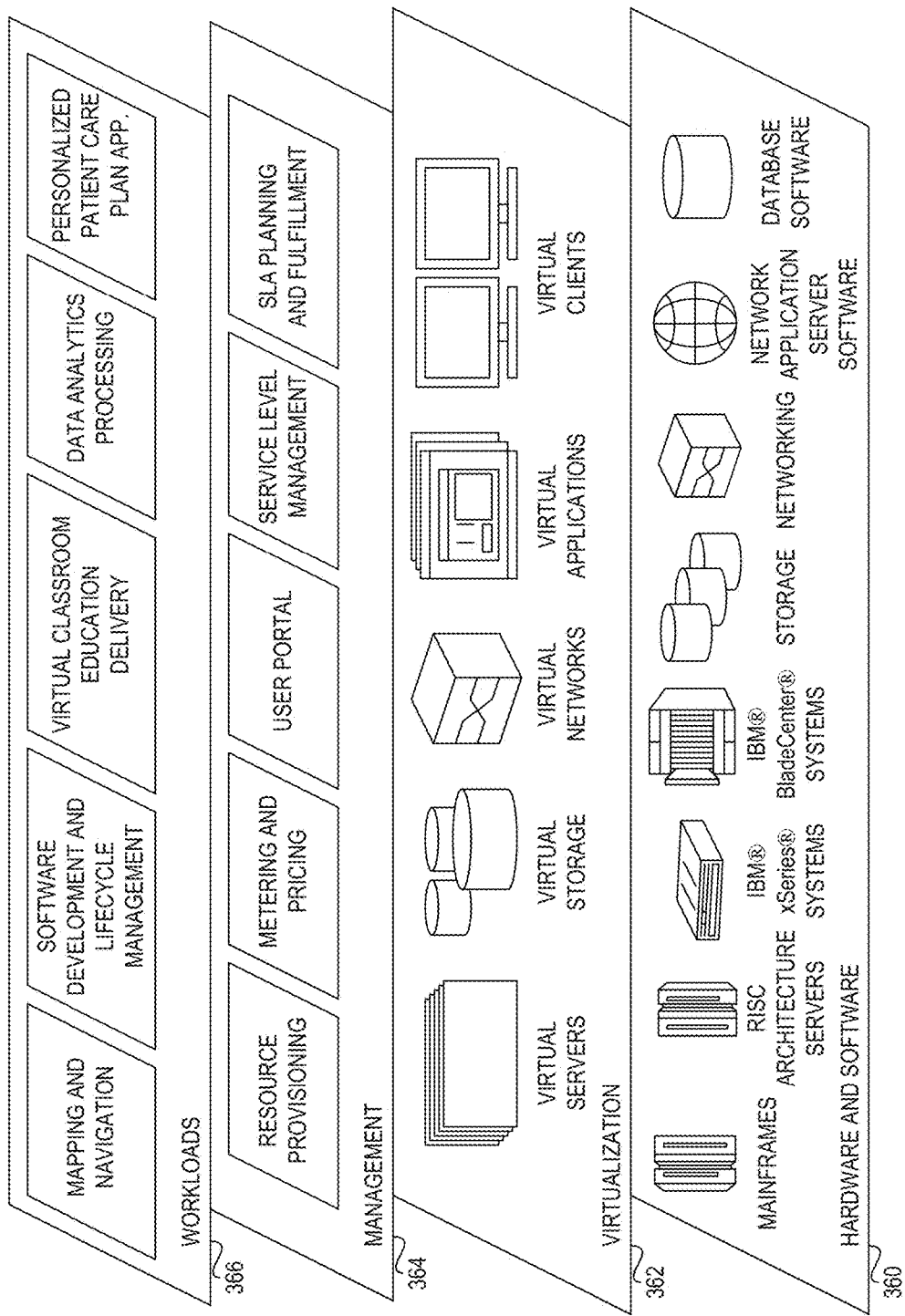
FIG. 3 is an example diagram illustrating a set of functional abstraction layers provided by a cloud computing environment in accordance with one illustrative embodiment.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided.

The hardware and software layer 360 includes hardware and software components. Examples of hardware components include mainframes, in one example IBM™ zSeries™ systems; RISC (Reduced Instruction Set Computer) architecture based servers, in one example IBM pSeries™ systems; IBM xSeries™ systems; IBM BladeCenter™ systems; storage devices; networks and networking components. Examples of software components include network application server software, in one example IBM Web Sphere™ application server software; and database software, in one example IBM DB2™ database software. (IBM, zSeries, pSeries, xSeries, BladeCenter, WebSphere, and DB2 are trademarks of International Business Machines Corporation registered in many jurisdictions worldwide).

The virtualization layer 362 provides an abstraction layer from which the following examples of virtual entities may be provided: virtual servers; virtual storage; virtual networks, including virtual private networks; virtual applications and operating systems; and virtual clients. In one example, management layer 364 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 366 provides examples of functionality for which the cloud computing environment may be utilized. Examples of workloads and functions which may be provided from this layer include: mapping and navigation; software development and lifecycle management; virtual classroom education delivery; data analytics processing; transaction processing; and, in accordance with the mechanisms of the illustrative embodiments, a personalized patient care plan creation and monitoring functionality.

Figure 4:
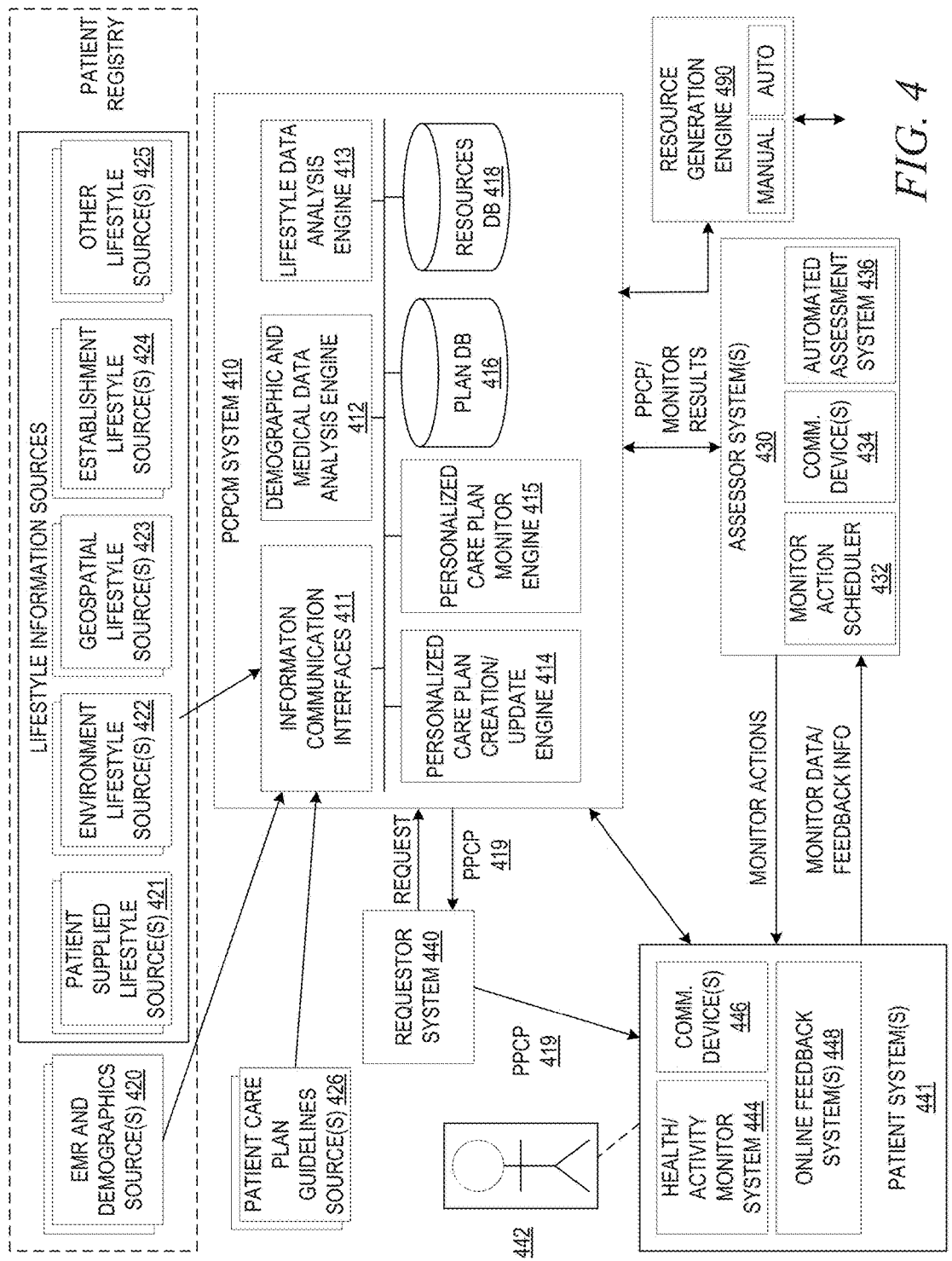
FIG. 4 is an example block diagram illustrating the primary operational elements of such a personalized patient care plan creation and monitoring system in accordance with one illustrative embodiment.

As discussed above, the illustrative embodiments provide a personalized patient care plan creation and monitoring system which may be implemented in various types of data processing systems. FIG. 4 is an example block diagram illustrating the primary operational elements of such a personalized patient care plan creation and monitoring system in accordance with one illustrative embodiment. The operational elements shown in FIG. 4 may be implemented as specialized hardware elements, software executing on hardware elements, or any combination of specialized hardware elements and software executing on hardware elements without departing from the spirit and scope of the present invention.

As shown in FIG. 4, a personalized patient care plan creation and monitoring (PCPCM) system 410 comprises information source interfaces 411, demographic and medical data analysis engine 412, lifestyle data analysis engine 413, personalized care plan creation/update engine 414, and personalized care plan monitor engine 415. In addition, the PCPCM system 410 maintains a personalized patient care plan database 416 that stores data corresponding to the personalized patient care plans generated for various patients.

A personalization resources storage 418 provides resources utilized by the personalized care plan creation/update engine 414 for identify and correlate demographic, medical, lifestyle information, and general patient care plan information associated with a patient into a series of personalized patient care plan actions and corresponding monitor actions for an assessor. The personalization resources storage 418 may comprise systems of rules, patterns, equations, algorithms, and various other types of logic that codify or otherwise implement functions for selecting and deciding how to personalize a general set of goals and actions in a general patient care plan to a personalized patient care plan. These rules, patterns, equations, algorithms, and the like, may be developed over time by subject matter experts, automatically identified by automated systems, such as natural language processing systems, or the like. For example, such automated and manual based mechanisms may be provided as part of a resource generating engine 419 described in greater detail hereafter.

The rules, patterns, equations, algorithms, etc., may be applied to the large set of demographic, medical, and lifestyle information obtained for the patient to obtain an automatically generated personalized patient care plan which may then be presented to a subject matter expert, such as a doctor, nurse, other medical professional, or the like, for confirmation before prescribing the personalized patient care plan to the patient. It should be appreciated that the resources 418 may further be utilized by the personalized care plan monitor engine 415 when monitoring adherence to a personalized patient care plan and determining modifications to the personalized patient care plan based on determined levels of adherence, as discussed hereafter. Moreover, the resources 418 may be used to determine appropriate actions for interacting with patients, care providers, payment providers, and the like.

The information source interfaces 411 provides a data communication interface through which patient data may be obtained from various sources including electronic medical records (EMRs) data source 420, patient supplied lifestyle data source 421, environment lifestyle information source 422, geospatial lifestyle information source 423, establishment lifestyle information source 424, and other various lifestyle information data sources 425. Moreover, the interfaces 411 comprise interfaces for obtaining patient care plan guidelines information from source 426. The EMR data source 420 may comprise various sources of electronic medical records including individual doctor medical practice systems, hospital computing systems, medical lab computing systems, personal patient devices for monitoring health of the patient, dietary information, and/or activity information of the patient, or any other source of medical data that represents a particular patient's current and historical medical condition. The EMR data source 420 may further comprise data representing the patient demographics since such information is typically gathered by providers of such medical data.

The patient supplied lifestyle data source 421 may be a database and/or computing system that gathers and stores information from the patient indicating the patient's response to questionnaires, presented either physically and then entered through a data entry process or presented electronically and gathered automatically, directed to the patient's lifestyle, preferences, and the like. For example, questions in the questionnaire may ask questions about the patient's personal daily schedule, home and work environment conditions, family information, preferences regarding food types, exercise types, times of the day for performing actions, and the like. This information is gathered directly from the patient but may not cover all aspects of the patient's lifestyle. This lifestyle information may be augmented by other lifestyle information gathered from other sources which may be third-party lifestyle information sources. These third-party lifestyle information may comprise information from commercial and governmental computing systems, databases, and the like, that characterize the patient's environment, availability to resources (e.g., products/services/facilities), etc.

In the depicted example, third-party lifestyle information sources comprise environment lifestyle information source 422, geospatial lifestyle information source 423, establishment lifestyle information source 424, and other various lifestyle information data sources 425. Examples of environment lifestyle information source 422 comprise weather information services, air quality information services, traffic information services, crime information services, governmental information services regarding public utilities, or any other environment lifestyle information source 424. As one example, a third-party geospatial lifestyle information source 423 may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, as mentioned above, specialty grocery stores, vitamin stores, pharmacies, restaurants, gyms, walking paths, parks, recreational areas, community pools, and the like, may be identified based on a GPS system and its associated databases of information.

The information from the geospatial lifestyle information source 423 may be used to request or lookup establishment information in the establishment lifestyle information source 424. For example, if the geospatial lifestyle information source 423 identifies an establishment type and specific identity of a particular establishment, this information may be used to request or lookup other third-party lifestyle information for the establishment in the establishment lifestyle information source 424, e.g., the establishment's website, an industry based website, blogs, commercial establishment information repository, or the like, to retrieve specific information about the identified establishment, e.g., menu items, nutrition information, hours of operation, and the like. Similarly, other third-party lifestyle information source 425 may provide information for correlation with patient care plan actions/tasks including hours of operations, products/services provided, distance from the patient's locations, and the like.

The lifestyle information obtained from the lifestyle information sources 421-425 may be combined with EMR and demographics information for a patient to generate a patient registry record of a patient registry. The patient registry may comprise information for a plurality of patients which may be operated on by the PCPCM system 410 to identify personalized patient care plans for patients, identify potential opportunities for improving care of patients in accordance with clinical rules applied to the patient information in the patient registry records, and the like.

The patient care plan guidelines source 426 provides information regarding the preferred treatments for various medical conditions or maladies in association with patient characteristics. These guidelines are generally associated with demographic and medical information about patients and provide general guidelines as to who qualifies for a treatment, or patient care plan, and who does not based on their medical information and demographic information. The patient care plan guidelines provide an initial basis for determining a general patient care plan for a patient which may then be personalized to the particular patient based on the lifestyle information specific to that particular patient. The patient care plan guidelines from the patient care plan guidelines sources 426 may be provided in a natural language text form which may be processed by natural language processing mechanisms of a resource generation engine 490 to generate clinical rules for determining actions to be performed, communications to be sent, portions of personal care plans to be applied to a patient, or the like. These automated mechanisms may be used in addition to, or in replacement of, manual processes of subject matter experts for generating clinical rules as part of the resources database 418.

The PCPCM system 410 may receive a request to generate a personalized patient care plan for a particular patient, such as from a physician's computing system, a patient computing system, or the like, which initiates the processes of the PCPCM system 410 including retrieving information about the specified patient from the EMR sources 420. The EMR sources 420 provide patient demographic and medical data, gathered from questionnaires, electronic medical records, and the like, to the medical data analysis engine 412 which analyzes the received data and extracts the necessary data for generating patient care plan from the demographic and medical data received. This information is then used as a basis for submitting a request to the patient care plan guidelines source 426 to retrieve patient care plan guidelines for the patient's specific demographics and medical data, e.g., the patient is a 40 year old female diagnosed with type 2 diabetes and thus, corresponding patient care plan guidelines for this combination of patient demographics and medical condition are retrieved from the patient care plan guidelines source 426. Alternatively, the patient care plan guidelines from source 426 may be previously ingested and converted to applicable clinical rules, either through an automated process, manual process, or combination of manual and automated processes. These clinical rules that codify the patient care plan guidelines may be stored in the resources database 418, for example.

The retrieved patient care plan guidelines and/or clinical rules are used along with the demographics and medical data for the patient to generate a baseline patient care plan based on an initial diagnosis of the patient's medical condition, one or more categorizations of the patient based on the collected demographic and medical data, the established patient care plan guidelines, and goals to be achieved by the patient care plan, such as may be specified in the established patient care plan guidelines and/or patient medical data. These operations are performed by the PCPCM system 410 utilizing the resources 418 which provide the clinical rules, logic, equations, algorithms and other logic for evaluating patient information and correlating that information with a patient care plan that comprises patient actions to be performed by the patient and monitoring actions to be performed by the assessor. It should be appreciated that based on the demographic information about the patient and the patient's medical data, only a general patient care plan is generated at this point.

The resulting general patient care plan generated by the personalized care plan creation/update engine 414 is then personalized based on the lifestyle information for the patient obtained via the lifestyle data analysis engine 413 convert the general patient care plan to a personalized patient care plan for the specific patient based on their own unique combination of lifestyle information. The lifestyle data analysis engine 413 obtains the lifestyle information from the various sources 421-425 and performs analysis to generate lifestyle inferences from the lifestyle data. Again, resources may be provided in the resources storage 418 for providing logic, algorithms, clinical rules, patterns, etc., for drawing these inferences from the received lifestyle information. For example, from schedule data for the patient, geospatial lifestyle information, environment lifestyle information, and the like for the patient, it may be determined, based on clinical rules, patterns, algorithms, and the like, that the patient has a sedentary occupation, works in a multi-story building that has a gym, lives in an area with access to parks and walking paths, and the like. As one example, the lifestyle information may indicate that the patient's occupation is a lawyer. From that information, a lookup of the occupation in an occupation database provided in the resources 418 may indicate characteristics of the occupation including characteristics of "stressful", "sedentary", and "long hours" which provides lifestyle inferences about the patient that can be utilized by rules in the resources 418 implemented by the personalized care plan creation/update engine 414 to personalize the general patient actions in the general patient care plan to the particular patient. Various analysis of lifestyle information may be used to extract such inferences from the data which can then be used to personalize a general patient care plan.

As mentioned above, lifestyle information data is obtained from various sources 421-425 to obtain an overall representation of the lifestyle of the patient. These third-party lifestyle information sources 422-425 may provide lifestyle information that is combined with lifestyle information provided by the patient himself/herself 421 for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided in the lifestyle data analysis engine 413 to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan. Non-limiting examples of ways in which general patient care plans may be personalized based on lifestyle information have been provided above. Such personalization may be performed by the personalized care plan creation/update engine 414.

It should be appreciated that the lifestyle information and/or resources 418 may comprise various reference resources from which the mechanisms of the PCPCM system 410 may obtain information for making decisions as to how to personalize the patient care plan actions (patient actions and monitoring actions). Such reference resources may comprise drug information repositories, food nutrition repositories, exercise information repositories, medical procedure repositories, and the like. The "reference" resources differ from other lifestyle information sources in that these "reference" resources tend to be universal for all patients. Such reference resources may be utilized, for example, to assist in determining drug affects on other lifestyle characteristics (e.g., drugs that make one lethargic, prone to disorientation, or the like), selecting foods whose nutritional content falls within the desired goals of a patient care plan, selecting exercises that generate a desired level of activity within a given period of time, and the like.

It should be appreciated that in addition to the evaluation of the patient's demographic, medical, and lifestyle information, the personalized care plan creation/update engine 414 may evaluate the historical personalized care plan information for a patient to determine appropriate patient actions to include in a personalized care plan. For example, the personalized care plan creation/update engine 414 may look to a history of personalized care plans created for this patient, as may be maintained in the personalized patient care plan database 416 in association with an identifier of the patient, to determine what patient actions the patient was able to successfully complete in previously prescribed personalized patient care plans and use this information to select those same patient actions for a current personalized patient care plan should the current personalized patient care plan have similar goals, general patient actions, and the like that the previously successful patient actions would satisfy. Thus, when selecting personalized patient actions to include in the personalized patient care plan, different weightings may be applied to patient actions based on whether or not they were previously prescribed to this patient, whether or not they were previously successfully completed by the patient in previously prescribed personalized patient care plans, and a level of successful or non-successful completion of the patient action in previously prescribed personalized patient care plans. A highest ranking patient action, amongst the possible patient actions, may then be selected for inclusion in the personalized patient care plan.

Thus, the PCPCM system 410 provides the various mechanisms for providing actual personalized patient care plans based not only on a categorization of the patient based on their medical diagnosis and demographic information, but also based on their own specific lifestyle information and lifestyle information obtained from third-party sources. In addition, the PCPCM system 410 further provides the mechanisms for generating, as part of the personalized patient care plan, monitoring actions to be performed by an assessor, e.g., a care team member which may be a single care team member or one in a plurality of care team members (human beings that are responsible for assisting the patient in adhering to their PCP), associated with the patient in monitoring the patient's performance of the patient actions of the personalized patient care plan. That is, based on the creation of the series of patient actions to be performed by the patient over a designated period of time, e.g., daily, weekly, monthly, etc., corresponding monitoring actions are identified by the personalized care plan monitor engine 415 using the resources 418. The resources 418 may comprise rules, logic, patterns, algorithms, etc. that match monitoring actions to types of patient actions. Based on timing information for the patient actions, preferences specified by the patient in the patient supplied lifestyle information 421, and the like, these monitoring actions may be scheduled as part of the personalized patient care plan monitor, e.g., every day the patient wakes at 7:00 a.m. and eats breakfast at 7:30 a.m., therefore schedule a monitoring action at 7:25 a.m. to send a text message to the patient's communication device to inform the patient that they should eat bran flakes for breakfast on Monday, Wednesday, and Friday of the week. It should be appreciated that not every patient action needs to have a corresponding monitoring action and that monitoring actions may be schedule for only a subset of the patient actions which are determined to be of most value in assisting the patient with adherence to the personalized patient care plan.

Thus, the resulting personalized patient care plan comprises patient actions to be performed by the patient, and corresponding monitoring actions to be performed by the assessor. Having generated a personalized patient care plan (PPCP) taking into account the patient's personal lifestyle, the PCPCM system 410 outputs the personalized patient care plan 419 to the requestor system 440 for use by the patient 442 in performing the patient actions of the personalized patient care plan. In addition, as noted above, the personalized patient care plan 419 further comprises monitoring actions that are to be performed by an assessor via assessor systems 430, which may be a human being utilizing communications and/or computing equipment 432-436 to perform their monitoring actions, an automated system 436 that automatically performs monitoring actions, or a combination of human and automated systems. The personalized patient care plan 419 is output to the assessor system(s) 430 such that the assessor may utilize the monitoring actions in the personalized patient care plan 419 to monitor and evaluate the patient's performance of the patient actions.

In monitoring the patient 442 and the patient's adherence to the personalized patient care plan 419, the assessor system(s) 430 may obtain feedback information from various patient systems 441 including a health/activity monitor system 444, communication device(s) 446, online feedback system(s) 448, or the like. Examples of health/activity monitor system 444 include wearable devices, such as a FitBit™, iFit™ Fitness Tracker, pedometers, smart scales, medical equipment with data connectivity to one or more networks via wired or wireless data communication links, Internet of Things (IoT) devices, or the like. Examples of communication device(s) 446 may include smart phones with applications for communication via data networks to log health and activity data for the patient 442, conventional phones through which a human or automated mechanism places calls to the patient 442, or the like. Examples of online feedback system(s) 448 include websites for tracking a patient's medical condition including online food logs, weight monitoring services, and other health and activity monitoring systems. Any systems that facilitate monitoring and/or communication with an assessor may be used as part of the patient system(s) 441 without departing from the spirit and scope of the illustrative embodiments.

Examples of monitoring actions performed by the assessor system(s) 430 may include interrogating the health/activity monitoring devices and/or applications executing on the communication devices 446 or online feedback system(s) 448 associated with the patient, and initiating a reminder communication to be sent to the patient's communication device 446 via the assessor communication device 434 to remind the patient 442 to perform an action in accordance with their personalized patient care plan 419, scheduling a doctor's appointment for the patient and informing them of the appointment, initiating a call to the patient's communication device 446 to discuss their progress, or any other action that a human or automated assessment system 436 may perform to assist with the monitoring of the patient's adherence to the patients' personalized patient care plan 419. Moreover, results of the monitoring may be returned to the PCPCM system 410 for use in modifying the personalized patient care plan 419 based on the patient's determined level of adherence to the personalized patient care plan 419.

In response to monitoring results and feedback gathered by the assessor system(s) 430, and provided back to the PCPCM system 410, or provided directly to the PCPCM system 410 from the patient system(s) 441, the personalized care plan creation/update engine 414 may dynamically adjust or modify the personalized patient care plan 419 based on a determined level of adherence to the personalized patient care plan 419. That is, the patient's adherence to their personalized patient care plan 419 is monitored via the assessor system(s) 430 and the patient system(s) 441, and determinations are made as to whether the patient meets the goals set forth in the personalized patient care plan 419 and/or performs the patient actions in the personalized patient care plan 419. If the patient does not meet the requirements of one or more goals in the patient care plan 419, an alternative goal determination logic of the personalized care plan creation/update engine 414 is employed to determine an alternative goal that the patient is more likely to be able to accomplish. This determination may be made based on the patient's actual progress towards attaining the original goal, the importance and type of the goal to the overall personalized patient care plan, e.g., adjustments to medication may not be able to be made depending on the particular care plan, and a pre-determined inter-changeability of the goals. These determinations may be made in a similar manner as previously described above with regard to the original generation of the personalized patient care plan utilizing the resources 418 and the like, with the adherence feedback and monitoring data being used as additional lifestyle information for influencing the selection of patient actions and corresponding monitoring actions.

In some cases, one goal may be adjusted in one direction and another in a different direction so as to balance the patient's ability to achieve a missed goal with an alternative goal while maintaining overall results that are to be generated, e.g., physical activity goal may be reduced while dietary goals may be increased so that the balance achieves the same overall effect. In some illustrative embodiments, the determination of alternative patient actions for performing the alternative goals may be based on a historical analysis of patient actions in other patient care plans that the patient has undergone. This historical analysis may identify other similar patient actions that achieved similar results to the patient actions that the patient is found to not be able to achieve in the patient's current personalized patient care plan. Such historical analysis may be performed in a similar manner as previously described above but with a focus on patient actions that were not achieved by the patient 442 in the PPCP 419.

It should be appreciated that the patient systems may further comprise systems for identifying the current location, environmental conditions, changes in a schedule, and the like, for use by the assessor systems 430 in providing feedback to the PCPCM system 410 to adjust the PPCP 419 for the patient's current location and environment. That is, the PPCP 419 may be dynamically adjusted based on the patient's current environmental conditions, changes in schedule, determined deviations from the care plan, and other dynamic conditions that may interfere or otherwise require modification, either temporarily or permanently, of the patient's personalized patient care plan. As noted above, such factors as weather conditions, temperature conditions, resource availability (e.g., gym is closed), and the like may require temporary modifications to a patient's personalized patient care plan. Other factors, such as the patient moving to a new location, obtaining a new place of employment, or the like, may require more permanent modifications to the patient's personalized patient care plan. Such factors may be identified and corresponding modifications initiated taking into account the new temporary/permanent lifestyle changes of the patient.

Figure 5:
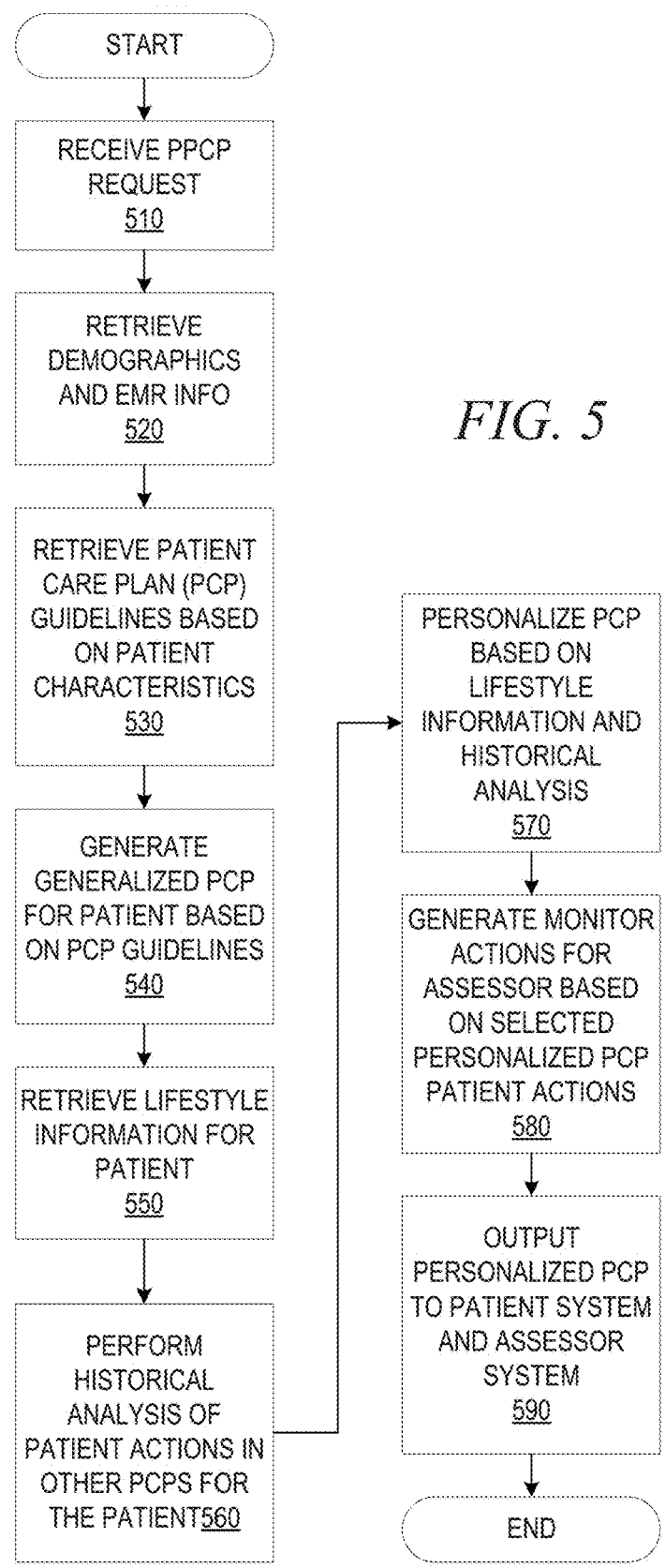
FIG. 5 is a flowchart outlining an example operation for creating a personalized patient care plan in accordance with one illustrative embodiment.

FIG. 5 is a flowchart outlining an example operation for creating a personalized patient care plan in accordance with one illustrative embodiment. As shown in FIG. 5, the operation comprises receiving a request (Personalized Patient Care Plan (PPCP) request) for the creation of a personalized patient care plan specifically identifying a patient for which the personalized patient care plan is to be created (step 510). EMR and demographic information is retrieved for the patient (step 520) and used to retrieve one or more patient care plan guidelines corresponding to the patient's characteristics (step 530). A generalized patient care plan (PCP) is generated for the patient based on the retrieved PCP guidelines and the patient's demographics and medical information (step 540).

Patient specific lifestyle information is retrieved for the patient from a plurality of different lifestyle information sources (step 550). Moreover, in some illustrative embodiments, a historical analysis is performed on patient actions in previously prescribed PCPs for this patient to identify patient actions that are ones that the patient is likely to be able to adhere to and weight them more heavily during a selection process (step 560). A personalized PCP is generated based on the generalized PCP as a basis which is then customized and personalized to the specific patient using the retrieved lifestyle information, the historical analysis results identifying patient actions that are likely to be adhered to by this patient, and established rules, patterns, algorithms, logic, etc., for generating personalized patient actions and combining them in a serial manner to generate a sequence of patient actions and goals that together constitute the patient's side of the personalized patient care plan (step 570). Based on the selected patient actions in the personalized patient care plan, corresponding monitor actions for all or a subset of the patient actions are generated using monitoring action rules, patterns, algorithms, logic, or the like (step 580). The monitoring actions are combined with the patient actions in the personalized PCP (PPCP) which is then output to the patient system(s) and assessor system(s) for implementation and monitoring of the PPCP (step 590). The operation then ends.

Figure 6:
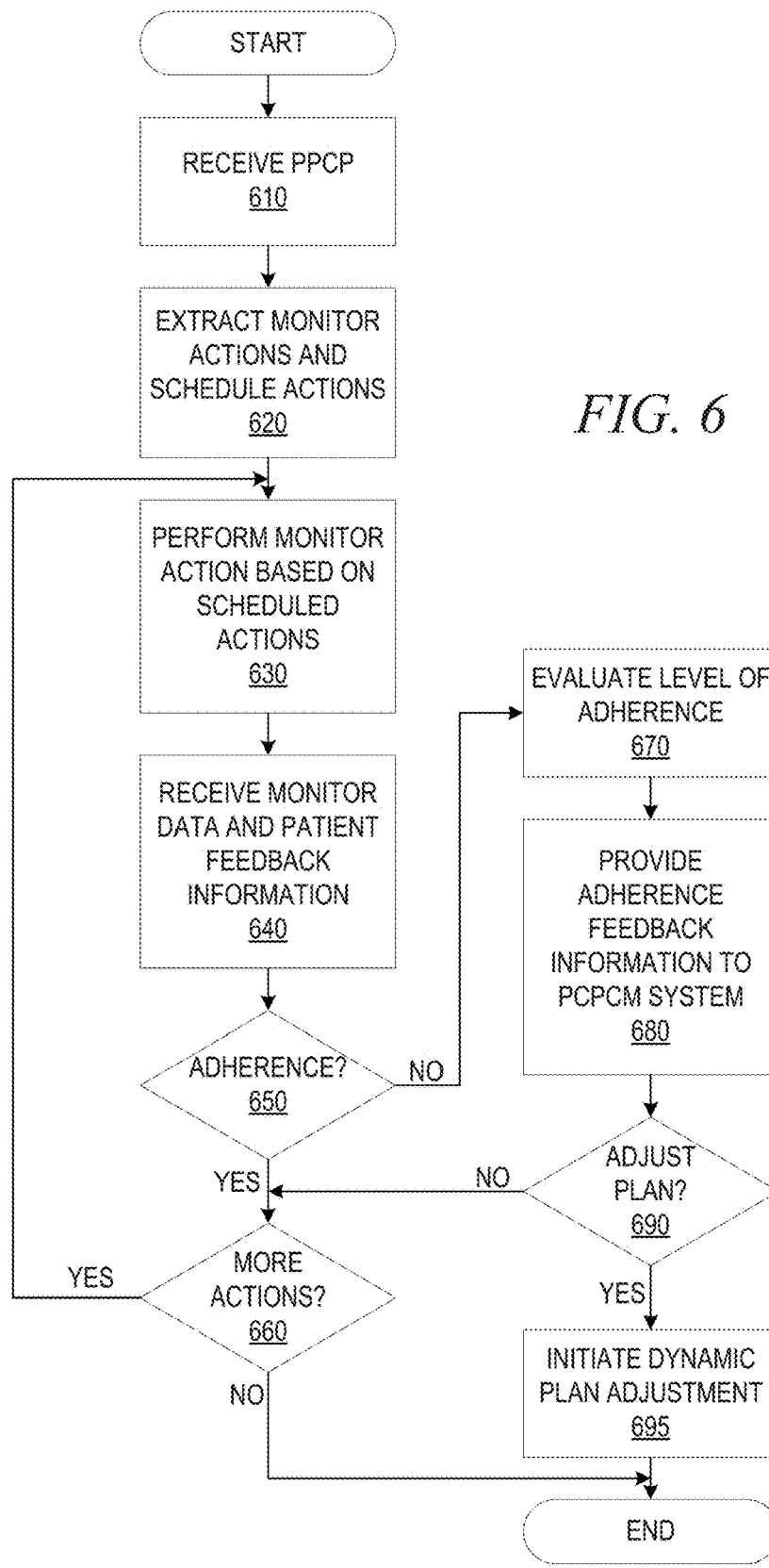
FIG. 6 is a flowchart outlining an example operation for monitoring a patient's performance with regard to a prescribed personalized patient care plan in accordance with one illustrative embodiment.

FIG. 6 is a flowchart outlining an example operation for monitoring a patient's performance with regard to a prescribed personalized patient care plan in accordance with one illustrative embodiment. As shown in FIG. 6, the operation starts by receiving a PPCP (step 610) from which monitor actions are extracted and scheduled by an assessor system (step 620). A next monitor action in the schedule of monitor actions with regard to this patient is performed based on the schedule (step 630). It should be appreciated that the performance of such monitor actions may be automated, may be performed by a human, or may be a semi-automatic process in which different aspects of the monitor action are performed by an automated system and by a human.

In response to the monitor action being performed, monitor data and patient feedback information are received (step 640). For example, this may involve interrogating a health/activity monitoring device associated with the patient and receiving the corresponding data as a result. As another example, this may involve a human assessor calling the patient, asking the patient some questions about the patient's adherence to the PPCP, and then performing data entry to enter the monitor data and patient feedback information into the assessor system. In still another example, this may involve the patient logging onto an online system and inputting monitor data into the system which then reports the information to the assessor system, e.g., a patient entering blood sugar measurement data, weight data, symptom data, or the like. Many different ways of obtaining monitor data and patient feedback data may be utilized depending on the desired implementation of the illustrative embodiments.

Based on the monitor data and patient feedback information received, a determination is made by the assessor system as to whether the patient is adhering to the patient action required in the PPCP (step 650). If the patient action in the PPCP is being adhered to, then a determination is made as to whether more patient actions in the PPCP to be checked (step 660). If so, the operation returns to step 630. If there are no more patient actions to be checked, then the operation terminates.

If the patient action is not being adhered to, as may be determined from a comparison of the patient's monitor data and feedback to the requirements of the patient action in the PPCP, then an evaluation of the level of adherence is performed (step 670). Adherence feedback information is provided to the PCPCM system (step 680) and a determination is made as to whether the level of adherence is such that it warrants an adjustment of the patient actions in the PPCP (step 690). This determination may take into account various factors including the nature and importance of the patient action to the overall goal of the PPCP, e.g., taking medication may be considered much more important that walking for 30 minutes a day, a number of times this patient action has not been adhered to over a specified period of time, e.g., patient fails to walk for 30 minutes for 3 days in the past 5 days, an amount of the patient action that was actually achieved, e.g., the patient walked for 20 minutes but not 30 minutes, and the like. Based on a determined level of adherence and the nature and importance of the patient action, the assessor system determines whether an adjustment of the PPCP is needed (step 690).

If an adjustment is needed, then the dynamic plan adjustment operations of the PCPCM system 410 are initiated by a request from the assessor system (step 695). If an adjustment is not needed, then the operation continues to step 660 where it is determined whether more patient actions in the PPCP need to be evaluated. If so, the operation returns to step 630, otherwise the operation terminates.

Figure 7:
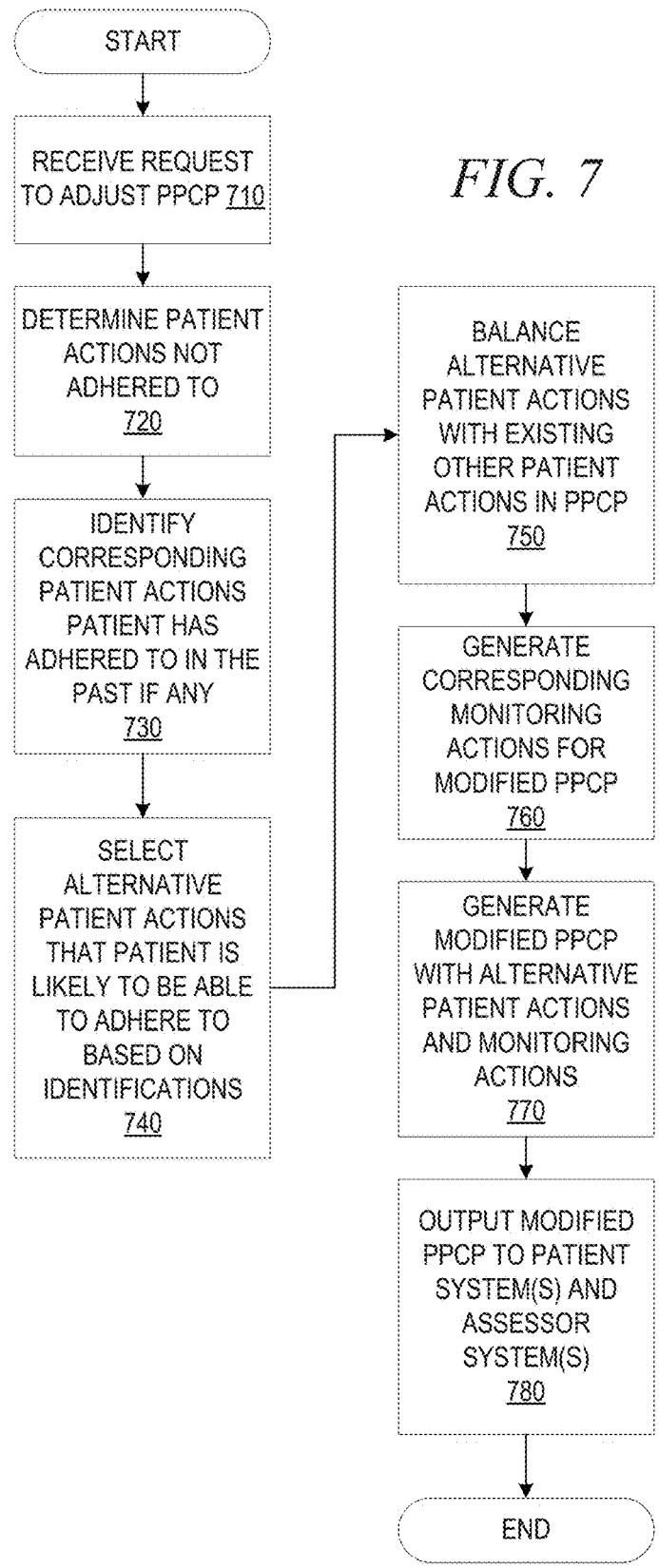
FIG. 7 is a flowchart outlining an example operation for adjusting a personalized patient health care plan based on an evaluation of a patient's adherence to a prescribed personalized patient health care plan in accordance with one illustrative embodiment.

FIG. 7 is a flowchart outlining an example operation for adjusting a personalized patient health care plan based on an evaluation of a patient's adherence to a prescribed personalized patient health care plan in accordance with one illustrative embodiment. As shown in FIG. 7, the operation starts by receiving a request to adjust the PPCP for a patient, such as from the assessor system (step 710). The patient actions not adhered to are determined (step 720) and corresponding patient actions that the patient has adhered to in the past (if any) are identified (step 730).

Alternative patient actions that the patient is likely to be able to adhere to are selected based on the identification in step 730 (step 740). The alternative patient actions are balanced with existing patient actions in the PPCP (step 750). This balancing may comprise adjusting other patient actions based on the alternative patient actions so as to achieve the same overall goals of the patient care plan, e.g., adjusting nutrition based patient actions based on changes to exercise or medication based patient actions.

Based on the modified patient actions, corresponding monitoring actions for the modified PPCP are generated (step 760) and a modified PPCP with the alternative patient actions and monitoring actions is generated (step 770). The modified PPCP is output to the patient system(s) and assessor system(s) (step 780) and the operation terminates.

Thus, the illustrative embodiments provide mechanisms for personalizing a patient care plan for a specific patient's own unique set of lifestyle characteristics such that the patient care plan is not generally applicable to a plurality of patients but is specific for the one patient. Information from various lifestyle information sources may be used along with patient care plan guidelines, demographic information, medical information, various resources, and the like, to generate a personalization of a more generic patient care plan that meets the desired goals for addressing a patient's medical condition. The personalization of the patient care plan may take into consideration patient actions that are successfully and unsuccessfully performed by the patient in other patient care plans. This may be done on a historical basis as well. Furthermore, the mechanisms of the illustrative embodiments provide monitoring actions for monitoring the patient's adherence to the personalized patient care plan and initiation of modifications to the personalized patient care plan when such adherence meets pre-defined criteria indicative of a need for a modification in the patient care plan.

Generation of Clinical Rules for Application to Patient Information

As noted above, the resources database 418 may comprise rules, logic, equations, and the like that are applied by the one or more of the demographic and medical data analysis engine 412, lifestyle data analysis engine 413, and personalized care plan creation/update engine 414 for evaluating patient information from EMR and demographics sources 420 and patient lifestyle information sources 427 to perform various operations. For example, clinical rules may be applied by the demographic and medical data analysis engine 412 and lifestyle data analysis engine 413 to determine one or more patient lifestyle classifications of the corresponding patient and store such classification information in association with the patient's lifestyle information 425, as part of the patient's PPCP stored in the plan database 416, or the like. Based on the classification of the patient into one or more patient lifestyle classifications, corresponding personalized care plan actions, requirements, and the like, may be associated with the patient to generate a personalized care plan and actions to be performed by an assessor. Moreover, application of such rules may be used to perform other actions such as identifying patients that represent care opportunities for providing improved care to patients, communicating with patients, and the like.

The rules may be generated by resource generation engine 490 using a manual, automatic, or semi-automatic operation and corresponding tools for performing such operations. Although shown in FIG. 4 as separate from the PCPCM system 410, it should be appreciated that the resource generating engine 490 may be integrated in PCPCM system 410 in some illustrative embodiments. In some illustrative embodiments, the resource generation engine 490 may provide user interfaces to users of client computing devices for their use in defining rules, equations, and/or logic for evaluating patient information. In one illustrative embodiment, these user interfaces comprise graphical user interfaces with object oriented representations of rule elements that may be dragged and dropped, user interfaces for selection of rule elements from a pre-determined listing, user interface elements for free-form text entry, and the like.

As noted above, in some illustrative embodiments, automated tools may be used either alone or with manual intervention to generate resources for the resources database 418, such as clinical rules, equations, and/or logic to be applied to patient information. These tools may be created by users utilizing a traditional graphical user interface (GUI), or they may use cognitive computing concepts to assist the user with creating or modifying rules. Cognitive computing techniques used to build rules might include natural language processing or speech-to-text algorithms and systems for taking natural language input, parsing the input, extracting key features from the natural language input, associating these key features with corresponding concepts and values, and generating a structured output that essentially converts the non-structured natural language input to structured information that may be used to generate results/responses. One example of a cognitive based mechanism that may be employed for performing such analysis, extracting features, and generating structured information is the IBM Watson™ cognitive system available from International Business Machines (IBM) Corporation of Armonk, N.Y.

For example, natural language processing may evaluate a patient care plan guideline from source 426 that states "Medication A is safe for adult male patients younger than 65 years of age and having type 2 diabetes without amputation." From this information, structured data may be specified for defining a clinical rule such as the result being administering medication A and the corresponding structured characteristics being male, 18-65, type 2 diabetes, no amputation. These structured characteristics may then be automatically combined into a rule specifying the characteristics required to be present or not present for the corresponding result to be applicable, e.g., the corresponding action to be applicable, corresponding personalized care plan element to be added to the patient's personalized care plan, or any other result that is appropriate for the particular implementation which can be triggered as a result of the conditions/criteria of the rule being satisfied.

The rules themselves may be specified in a structured manner as a set of conditions/criteria specifying characteristics of the patient that must be present (AND requirements), those that may be present (OR requirements), and/or those that must not be present (AND NOT requirements) for the corresponding result to be applicable to the particular patient. The characteristics themselves may take many different forms including demographic information, lifestyle information, medical information, source information, and the like. The characteristics may be specified in terms of date ranges, values, data source identifies, medical codes, combinations of characteristics of the same or different types, or the like.

The rules may be nested or otherwise configured in a hierarchical manner such that if one rule is satisfied by the patient information, this may trigger additional rules to be applied until a final determination as to the action, communication, or other result is generated. This configuration sets forth one or more cascading sets of rules such that one rule triggers another rule to be evaluated. For example, a first rule may look to a first subset of patient information to determine if the patient is within a specified age range, is a particular gender, and has been diagnosed with a particular medical malady. If all of these criteria are satisfied, then this may trigger a second rule that looks to lifestyle information of the patient to determine where the patient lives and if the patient lives in a specified geographical area, as well as the patient's amount of physical activity as determined from the patient's occupation and hobbies or interests. This information may be classified and compared to the criteria of the second rule to determine if the criteria of the second rule are satisfied, e.g., lives is north America and has a sedentary lifestyle, which would then trigger the corresponding result, e.g., add exercise to the patient care plan, initiate a communication to promote a gym membership, or the like.

In accordance with some illustrative embodiments, the rules may be categorized into three main types of rules: demographic rules, medical code rules, and lifestyle information rules. Demographic rules specify one or more conditions or criteria associated with patient demographics, e.g., age, gender, geographical location (e.g., portions of the residence address), occupation, and the like. Medical code rules specify one or more conditions or criteria associated with medical codes that define symptoms, diagnoses, treatments, medical procedures, and the like, associated with the patient. Such medical codes may be specified in the medical history of the patient set forth in the patient registry entries for the patient, a current medical record entry, lab results, and the like. Lifestyle information rules specify one or more conditions or criteria associated with lifestyle patient supplied, environmental, geospatial, establishment, or other lifestyle information as discussed above. It should be appreciated that rules, of the same or different types, may be chained together to generate complex rule ontologies having hierarchical or tree-like structures in which cascading sets of rules are provided. Moreover, some rules may bridge more than one type such that a single rule may look at two or more of demographics, medical codes, and lifestyle information.

In some illustrative embodiments, the rules may be generally thought of as comprising conditions/criteria specified in three different categories, i.e. "AND" criteria, "OR" criteria, and "AND NOT" criteria. The "AND" criteria specify one or more criteria, all of which must be present in order for the rule to be triggered, where triggering a rule means that the criteria of the rule has been satisfied and the result of the rule is applicable to the patient information. The "OR" criteria specify one or more criteria where at least one of the "OR" criteria must be present in order for the rule to be triggered. The "AND NOT" criteria specify one or more criteria where none of the "AND NOT" criteria can be present for the rule to be triggered.

In some illustrative embodiments, an "Any X" qualifier may be applied to the different categories of criteria. What is meant by an "Any X" qualifier is that rather than requiring all of the "AND" criteria to be present, none of the "AND NOT" criteria to be present, and at least one of the "OR" criteria to be present, a number of criteria may be specified as the "X" value and thus, override the default operation of the "AND", "OR," and "AND NOT" criteria. Or, alternatively, the X may specify a number of instances of the corresponding criteria that must be present in the patient information. For example, an X value of 2 may be set for the "AND" criteria meaning that the patient information must include at least 2 of the "AND" criteria or at least two instances of the "AND" criteria (where these 2 instances may be for the same "AND" criteria, e.g., 2 instances of a medical code of type 2 diabetes). Moreover, an "Any X" qualifier may be applied to the "OR" criteria that states that at least X number of the "OR" criteria must be present in the patient information, or at least X instances of at least one of the "OR" criteria must be present in the patient information. If the required number of criteria or instances is not met, then the rule is not triggered.

Moreover, an "Any X" qualifier associated with the "AND NOT" criteria may specify that the patient information must have at least X number of the "AND NOT" criteria to be eliminated from further consideration as triggering the rule. As a default operation, with the "AND NOT" criteria, if a patient's information indicates that the patient has any one of the criteria specified as an "AND NOT" criteria, then the patient is eliminated from further consideration for triggering the rule. However, by applying an "Any X" qualifier, this default operation may be modified to require more than one of the criteria to be present or more than one instances of one or more of the criteria to be present before the patient is disqualified for potentially triggering the rule.

By specifying all three categories of criteria, complex rules are generated that may be applied to patient information to identify specific types of patients for application of the result of the rules. Furthermore, by specifying a rule ontology of a hierarchical or tree-like arrangement, complex evaluations of patient information may be achieved.

Figure 8:
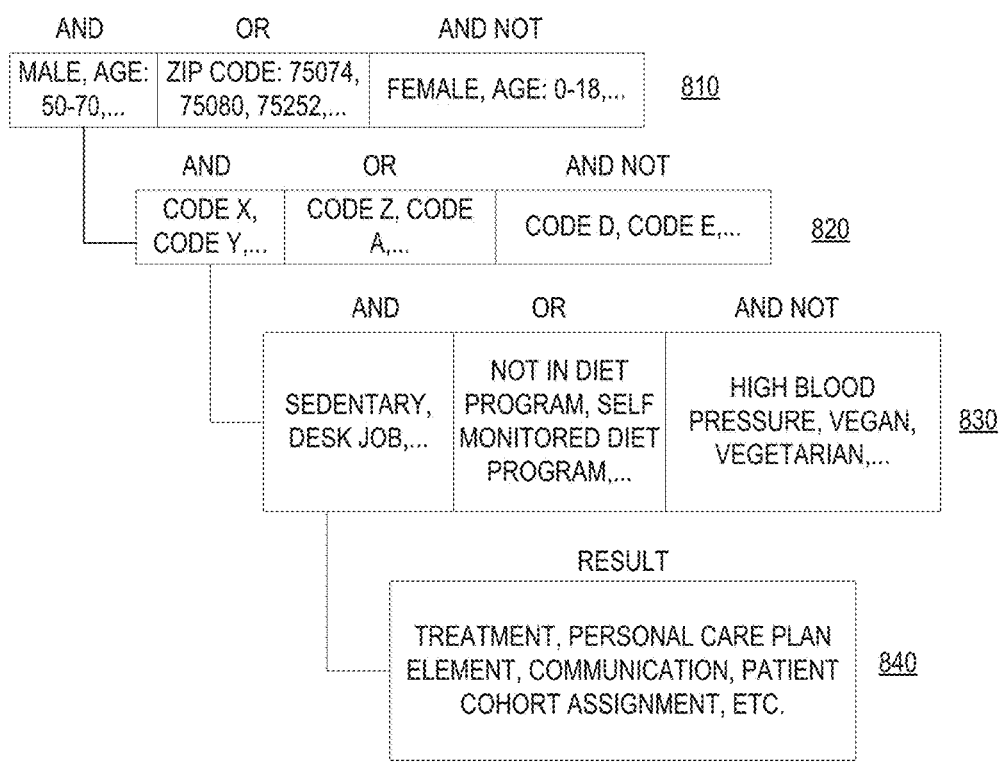
FIG. 8 is an example diagram of an example hierarchical set of rules in accordance with one illustrative embodiment.

FIG. 8 is an example diagram of an example hierarchical set of rules in accordance with one illustrative embodiment. As shown in FIG. 8, a nested hierarchical arrangement is provided comprising rules 810-830. The triggering of a rule 810, for example, causes a subsequent rule 820 to be evaluated to determine if it is triggered, which in turn causes a subsequent rule 830 to be evaluated. Each rule's criteria may be evaluated against patient information in a patient registry and/or obtained from other lifestyle and third party information sources. In the example shown in FIG. 8, the rules utilize the AND, OR, and AND NOT format previously mentioned above with the corresponding example criteria being shown in the corresponding boxes of the rule 810-830.

In the depicted example, rule 810 is an example of a demographics rule that uses criteria directed to the demographics of patient information. Rule 820 is an example of a medical code rule that uses criteria that is directed to the presence or absence of medical codes within the patient information. Rule 830 is an example of a rule that combines both lifestyle information and medical information in a single rule. For example, lifestyle information may indicate that the patient is sedentary, has a desk job, is not in a diet program or is in a self-monitored diet program, is or is not a vegan or vegetarian, and the like. Medical information from the patient's EMRs and the like, may indicate that the patient has or does not have high blood pressure, as well as other medical conditions. It should be appreciated that the criteria specified in the rules may include spatial and or temporal qualifiers as well, although not explicitly shown in FIG. 8. For example, a rule's criteria may specify that the patient has medical code X and also has medical code Y within 1 year of the time the patient was diagnosed with medical code X.

As shown in FIG. 8, the result generated from the triggering of rule 810 is to evaluate rule 820. Similarly, the result generated from triggering rule 820 is to evaluate rule 830. If all of the rules 810-830 are triggered, the final result 840 of rule 830 is performed. This final result 840 may comprise some recommendation for treatment, an addition of a personal care plan element to the patient's personal care plan, initiating a communication with the patient or medical personnel, or other suitable operation based on the particular implementation. If any of the rules in the hierarchy do not trigger, then the subsequent evaluations are not performed, i.e. the results of triggering the rule are not followed. It should be appreciated that the resources database 418 may comprise a complex set of rules of these types in various hierarchies or tree-structures for application to patient information.

Figure 9B:
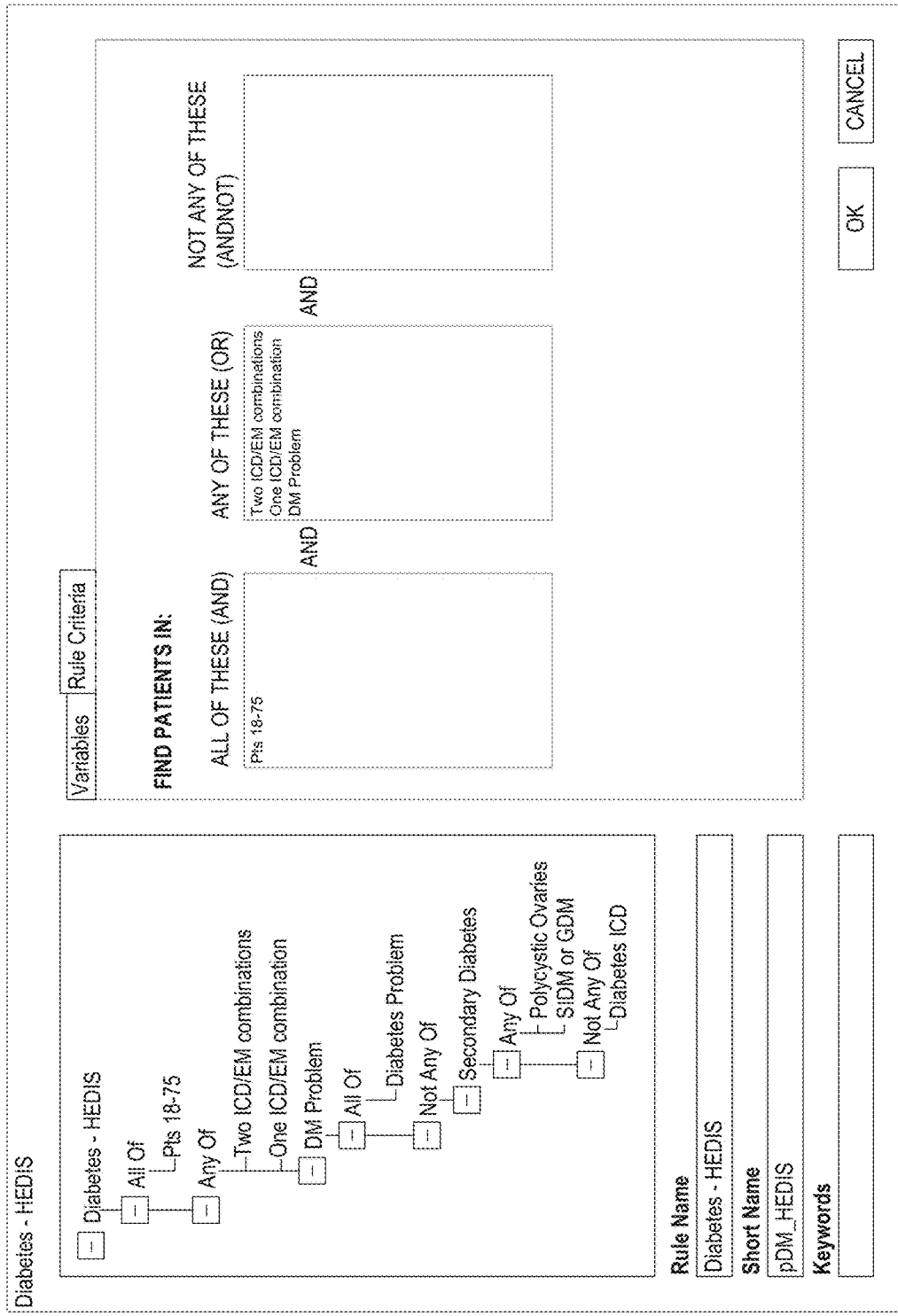

FIGS. 9A-9C are diagrams illustrating example graphical user interfaces for rule generation in accordance with one illustrative embodiment. The graphical user interfaces (GUIs) shown in FIGS. 9A-9C may be presented by the resource generation engine 490 to a user via the user's client computing device and one or more data networks and may be used by the user to define one or more rules for application to patient information, such as patient information in the patient registry.

FIG. 9A illustrates an example GUI for defining various medical codes that are recognizable by the mechanisms of the illustrative embodiments and used in the various rules of the illustrative embodiments. In FIG. 9A, medical codes indicating a diagnosis of diabetes are entered into a list of codes. In this example GUI, these codes are used by rules to identify diabetic patients when a matching code is found within the patient's medical record. Matching codes are then subjected to further selection criteria described within the rules engine, as shown in FIG. 9C described hereafter.

FIG. 9B illustrates an example GUI for defining a rule for identifying patients that are part of a classification of patients. As shown in FIG. 9B, the GUI comprises a field for specifying a rule name, e.g., "Diabetes—HEDIS", and a field for the short name of the rule which may be used to reference the rule in other rules, where HEDIS refers to the Healthcare Effectiveness Data and Information Set tool. The rule comprises an AND set of criteria, e.g., patients aged 18-75, an OR set of criteria, e.g., Two ICD/EM combinations or one ICD/EM combination and a DM Problem, and a ANDNOT set of criteria (none shown in the depicted example). The rule hierarchy is shown in the top left portion of the GUI. Various rules may be generated using this GUI and hierarchical combinations of rules may be generated through references to the short names of other rules. The hierarchies may be depicted in the top left portion of the GUI during generation. In this GUI example shown in FIG. 9B, the user has selected the rule at the top of the tree. The tree shows the hierarchy of the entire rule, while the lists depicted on the right side of the screen show the details for the top level of the hierarchy. The user can edit the rules and move them around in the hierarchy using the tree or by manipulating items on the detailed view displayed on the right hand side of the screen. Users can use the tree or the detailed view to add/edit/delete rules from the rule hierarchy. Users can also drag/drop or cut/copy/paste individual rules or an entire rule hierarchy from another rule.

FIG. 9C illustrates an example GUI for adding a medical code based rule referenced by the rule shown in FIG. 9B. In this example, the user has selected a code rule in the hierarchy "Two ICD9/EM combinations" that searches for instances of the list of diabetes codes depicted in FIG. 9A. When a user selects the code rule in the tree or double-clicks it in the detailed view, the detailed view changes to show details about the code rule. The detailed view shown in FIG. 9C depicts the criteria for the code based rule. This rule requires a two instances of diabetes codes entered on the same date as an office visit. Applicable office visit codes are identified within the ENC-27 code table (not shown, but similar to FIG. 9A). In this case, the medical code rule GUI comprises a title field for defining the title of the medical code rule, a code table field that specifies the medical code table that comprises the medical code information referenced by the medical code rule, e.g., the medical code table data structure defined using the GUI of FIG. 9A. Various tabs and corresponding fields are provided that permit the definition of the particular medical codes, combinations of medical codes, and requirements associated with these medical codes to satisfy the criteria of the medical code based rule shown in FIG. 9C.

FIG. 9D illustrates an example GUI for assembling rule relationships in accordance with one illustrative embodiment. In this example, multiple rules are defined as a starting point for another rule. In the example shown, only patients that match the criteria specified by both "sDM_A1C_INVERSE" rule AND the "sDM_A1C_VH" rules will be considered. The GUI allows the user to add or remove related rules as needed. Patients that match both of these rules will be matched against criteria for the "sDM_A1C_UNC" rule, which contains additional code rule and other criteria to identify diabetic patients with uncontrolled HBA1C levels.

Figure 9E:
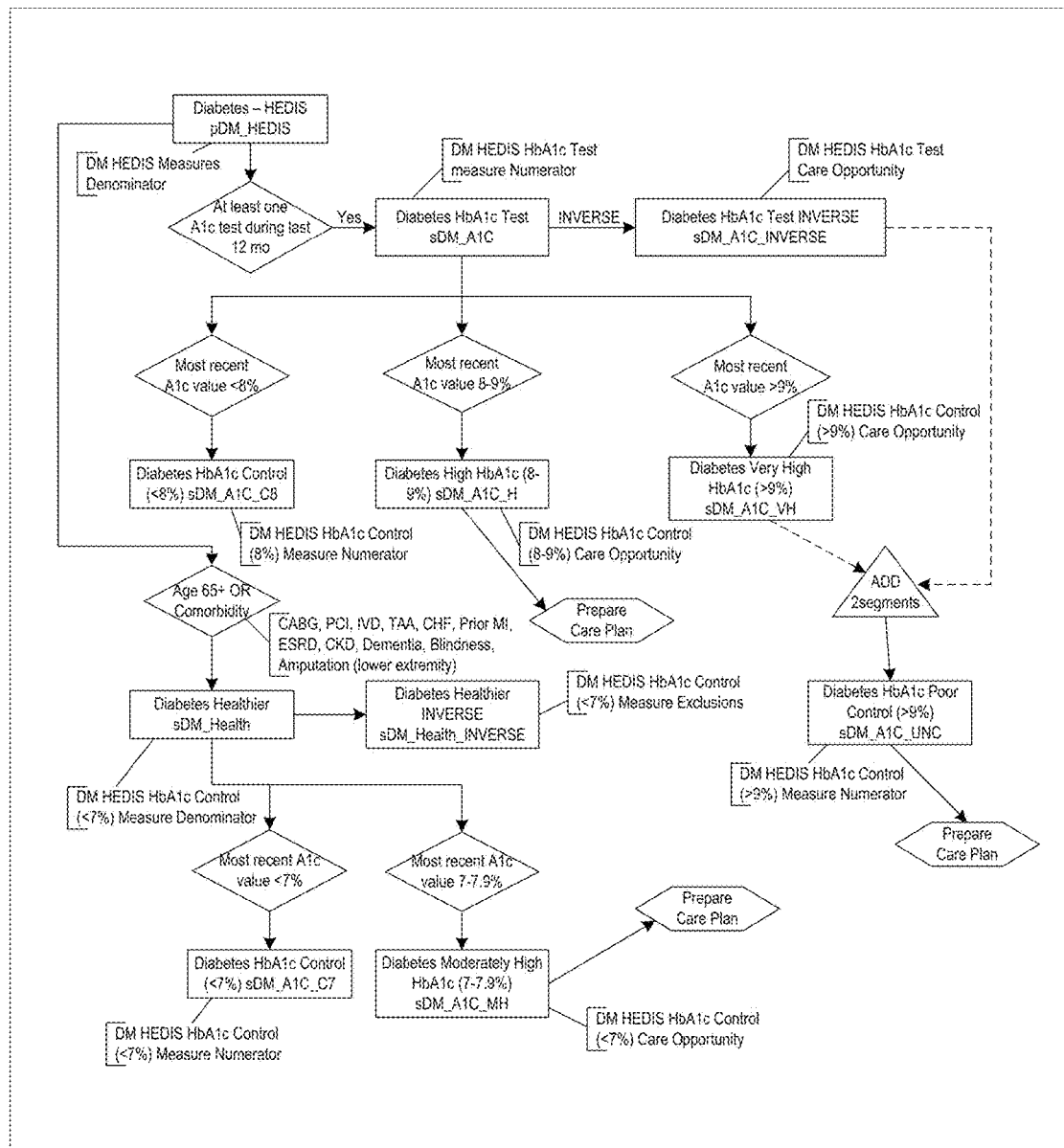
FIG. 9E represents an example rule flow illustrating the application of a rule in accordance with one illustrative embodiment.

FIG. 9E represents an example rule flow illustrating the application of a rule in accordance with one illustrative embodiment. This is the high-level logical flow for the rules depicted by the GUI shown in FIGS. 9A-9D. This diagram also shows how the registry rules are used to flow into a care plan for a patient.

The resulting rules may be stored in the resources database 418 and used by one or more of the analysis engines 412, 413 and personalized care plan monitor engine 415 to generate personalized care plans for patients, initiate communications with patients and/or medical personnel, or the like. In some illustrative embodiments, the rules may be used to identify patients that represent care opportunities, where a care opportunity is a patient whose condition or medical care is not sufficient to manage the patient's health or where modifications to the medical care may likely improve the patient's medical condition or management of their medical condition. The identification of care opportunities may be a basis for initiating other operations, such as instigating communication with the patient in accordance with communication workflows, identifying the patient as a candidate for improving medical personnel goal attainment, initiating the application of a medical campaign to the patient, or the like.

It should be appreciated that the rules may be stored in the resources database 418 in various sets or ontologies directed to performing different types of operations. For example, one set of rules may be directed to selecting patients for which a communication workflow should be applied to try to have the patient perform a compliance operation, e.g., schedule a doctor's appointment, submit to a particular test or medical procedure, fill a prescription, take medication, or the like.

In some illustrative embodiments, different sets of rules are established for determining whether patients are in compliance with their associated patient care plans or that the medical conditions are believed to be "under control" due to the patient and medical personnel performing the necessary actions to manage the medical condition. For example, the rules will be evaluated to identify the patient as either "in compliance", "non-compliant", or "excluded." Excluded patients are identified by a set of exclusion rules that define conditions that excuse a patient from normal clinical guidelines. For example, rules identifying patients due for a mammogram will include "EXCLUDE" rules in order to excuse those patients whose medical history includes a dual-mastectomy or active breast cancer so that they are considered compliant. Those excluded patients may be addressed under other rules that address different medical guidance specific to their condition.

A rule, or rules, may specify criteria for considering the patient to be in compliance with their treatment. If the rule, or set of rules, triggers, then the patient is considered compliant. If not, the patient is considered non-compliant, unless some other criteria is met to indicate that the patient is "excluded." Thus, based on the application of rules such as those discussed above, it may be determined that treatment A, from a set of treatments A-D, is to be associated with the patient. A separate set of rules may be applied to the patient information after treatment A has been prescribed, to determine if the patient is in compliance with their treatment or not. Those patients that are determined to be non-compliant are considered care opportunities for which additional actions may be triggered. For example, enrolling the patient in a campaign, performing an outreach operation by initiating a communication with the patient, generating or modifying the patient care plan, such as described above, or the like.

Communication with Patients Based on Historical Analysis

As mentioned above, the illustrative embodiments provide mechanisms for generating personalized patient care plans, monitoring a patient's adherence or compliance with a personalized patient care plan, and determining appropriate intervention actions to take to increase the likelihood that the patient will become compliant or adhere to the personalized patient care plan if the patient becomes non-compliant or does not adhere to the patient care plan ascribed to them. In determining appropriate intervention actions to perform, if the intervention action involves a communication with the patient, which most often it will, is desirable to communicate with the patient in a mode that is most likely going to result in the patient performing a compliance action or event so as to generate a successful outcome. A compliance action or event is one that brings the patient into compliance with the prescribed personalized patient care plan, or in greater compliance if not complete compliance with the prescribed personalized patient care plan.

In some illustrative embodiments, the mechanisms of the illustrative embodiments analyze the patient's personal patient information to identify instances in the patient's history where communications were made to the patient which resulted in a subsequent compliance action or event, e.g., an email reminder message sent to the patient followed by the patient scheduling an appointment within a predetermined period of time from the date/time of the email reminder message. These instances may indicate particular communication types or particular communication workflows, as described hereafter. Instances where communications were made that did not result in a compliance action or event may also be identified as well. A measure may be calculated for each communication type, combination of communication types, communication workflows, or the like, with regard to how often the communication(s) or workflow resulted in a subsequent compliance action or event within a predetermined period of time, indicative of the subsequent compliance action or event being attributable to the corresponding communication(s) or workflow. Positive instances (where a compliance action/event occurred within the predetermined time period) may increase this measure while negative instances (where a compliance action/event did not occur within the predetermined time period) may decrease this measure. Moreover, the type of compliance action or event may be identified with regard to each measure so as to identify which communication type(s) or workflows worked best for this particular patient for influencing the patient to perform a particular compliance action or event. That is, these measures may be compared to each other to determine which communication(s) are best for which types of compliance actions/events desired.

In addition, this information may be correlated with specific preferences and consents specified in the patient information. For example, only communication modes (or types) for which the patient has given a consent to be communicated with may be considered. For those communication modes, the corresponding best modes of communication as determined from the patient's history of communications in the patient information may be selected. For example, if, for a particular type of compliance action/event desired, the best modes of communication based on the patient's history indicate electronic mail and text messaging, but the patient has only given consent to be contacted by electronic mail, then only electronic mail may be utilized even if text messaging is determined to be the relative better mode to result in the compliance action/event. Such selection may further be based on the patient's specified preferences. Thus, if the patient, in the above example, consented to both electronic mail messaging and text messaging, but has indicated a preference for text messaging, then text messaging may be selected for use in communicating with the patient to elicit the compliance action/event.

It should be appreciated that the identification of communication mode(s) to utilize for eliciting a compliance action/event from a patient may comprise identifying a sequence or pattern of communication mode(s) as well as timing of communication mode(s) and content of communications. These may be specified in communication workflows as discussed below, or as sequences or patterns of communication mode(s) occurring prior to a compliance action/event occurring within a specified time period of a communication. Thus, for example, a patient's history in the patient information may indicate that the patient received an electronic mail message followed by a text message 3 days later, and followed by a phone call 2 days after the text message. This pattern or sequence of communication mode(s) may be identified in the patient information and used as a basis for potential selection for use in eliciting a compliance action or event from the patient in a current or future situation where the patient is determined to be non-compliant.

In addition to the communication modes, the illustrative embodiments may identify the more/less successful communication content for the individual non-compliant patient. For example, in embodiments where the communications utilize pre-defined templates or scripts, identifiers of the templates or scripts may be maintained in the patient information along with other communication mode information. These identifiers may be used in a similar manner to the identifiers of the communication modes to identify which templates/scripts, and thus, content, of communications are more/less successful in eliciting a compliance action/event from the patient. The templates/scripts may be associated, such as via metadata associated with the template/script, with different types of personality type or emotional characteristics which may be used to identify the types of content that are more/less successful with the particular patient. For example, the word choice in a template/script may be considered "forceful" or "friendly" or "urgent" and the patient's history information may indicate that the patient does not respond well to "forceful" communications but responds more readily to "friendly" communications. Therefore, if one wishes to elicit a compliance action/event from the patient, it is more likely to occur if a friendly content communication is utilized. This information may be combined with the selected communication mode(s) to determine a best mode and content for the communication(s) to bring the non-compliant patient into compliance.

It should be appreciated that the evaluation of content of communications is not limited to implementations where templates/scripts are utilized. To the contrary, natural language processing of the content of previous communications may be performed and keywords or key phrases may be extracted and correlated with emotional or personality characteristics so as to generate metadata associated with the communication instance. This information may be included in the patient information in association with the communication instance information so as to provide an indicator of content in the communication which can be analyzed in the manner discussed above.

Thus, illustrative embodiments are provided that include mechanisms for identifying one or more communication modes for communicating with a patient based on individual non-compliant patient information with regard to a history of responsiveness to different modes of communication. In addition to the patient information already discussed above, the patient information for a particular patient may include communication log data structures for tracking communications initiated with the patient including dates/times, types of communications, identifiers of particular scripts or templates used for the communications, content metadata, initiators of the communications, whether the communication resulted in a successful contact with the patient or not, and whether a subsequent compliance action or event occurred. The communication log data structures may be analyzed by the mechanisms of the illustrative embodiments to identify which modes of communication, and which types of content, are more successful with the particular non-compliant patient than others. This information may be used along with other patient information for the patient, such as communication mode preferences, communication mode consents, and the like, to select a communication mode that is most likely going to result in a compliance action or event. In some cases, while the patient may prefer one mode of communication, if the communication log data structures indicate that the patient is non-responsive to that mode of communication, an alternative mode of communication may be selected based on the communication log data structures, or "communication logs."

In some illustrative embodiments, the communication logs may store identifiers of communication workflows. A communication workflow is a set of one or more communications of the same or different communication modes and/or content, temporal information about the one or more communications, and content information specifying the type of content of the particular one or more communications, e.g., metadata indicating personality or emotional characteristics of the content. For example, a communication workflow may comprise a first email having content matching template A being sent at 7 pm on a Wednesday, an automated telephone call using script Q being made at 6 pm five days later, and a text message being sent two days later at 3 pm using a template Z. Communication workflows may be pre-defined and associated with an identifier. Thus, for example, there may be 10 different communication workflows with identifiers 1-10 and the communication logs may store this identifier in the communication log for a patient as part of the patient's information. The communication workflows may be associated with success/failure indicators indicating whether the communication workflow resulted in a responsive communication from the patient, e.g., the patient picking up the telephone, the patient replying to an electronic mail message, a read receipt from the patient being received, the patient clicking on a hyperlink in the communication or a graphical user interface element, or any other suitable indication that the patient received the communication. This information may also be correlated with patient information indicating the patient's actions thereafter with regard to scheduling an appointment with their physician, obtaining a lab test, filling a prescription for medication at a pharmacy, or any other compliance action or event.

It should be appreciated that the communication workflows identify combinations of communication modes and a temporal aspect of communication regarding an ordering of communication modes, a timing of communications, a number of times each communication mode is to be utilized, and the like. In some cases, the patient information may not specify an identifier of a specific pre-defined communication workflow. In such cases, sequence or patterns of communications modes and content may be identified through pattern analysis of the patient information. Thus, for example, an instance of an email at one date and time, followed by a phone call 2 days later, followed by a text message 3 days later, followed by a doctor's appointment being scheduled 30 days later represents a pattern of communications. Logic may be provided for identifying such patterns in patient information using temporal boundaries, e.g., communications that are within specific time frames of one another, triggering actions/events such as the compliance action/event, and the like, as basis for identifying these patterns.

Hence, an ad hoc sequence or pattern identifier is provided that can identify sequences/patterns of communications without pre-defined communication workflows. These ad hoc sequences/patterns may be used either alone or in combination with communication workflow identifiers to select a best communication mode or sequence/pattern of communication modes to use to elicit the compliance action/event from the non-compliant patient. Thus, the illustrative embodiments may perform a complex evaluation to determine what particular combinations of communication modes, and what temporal sequence, to utilize for particular types of patients based on historical analysis of both individual non-compliant patient and the aggregate of similar patients.

Figure 10:
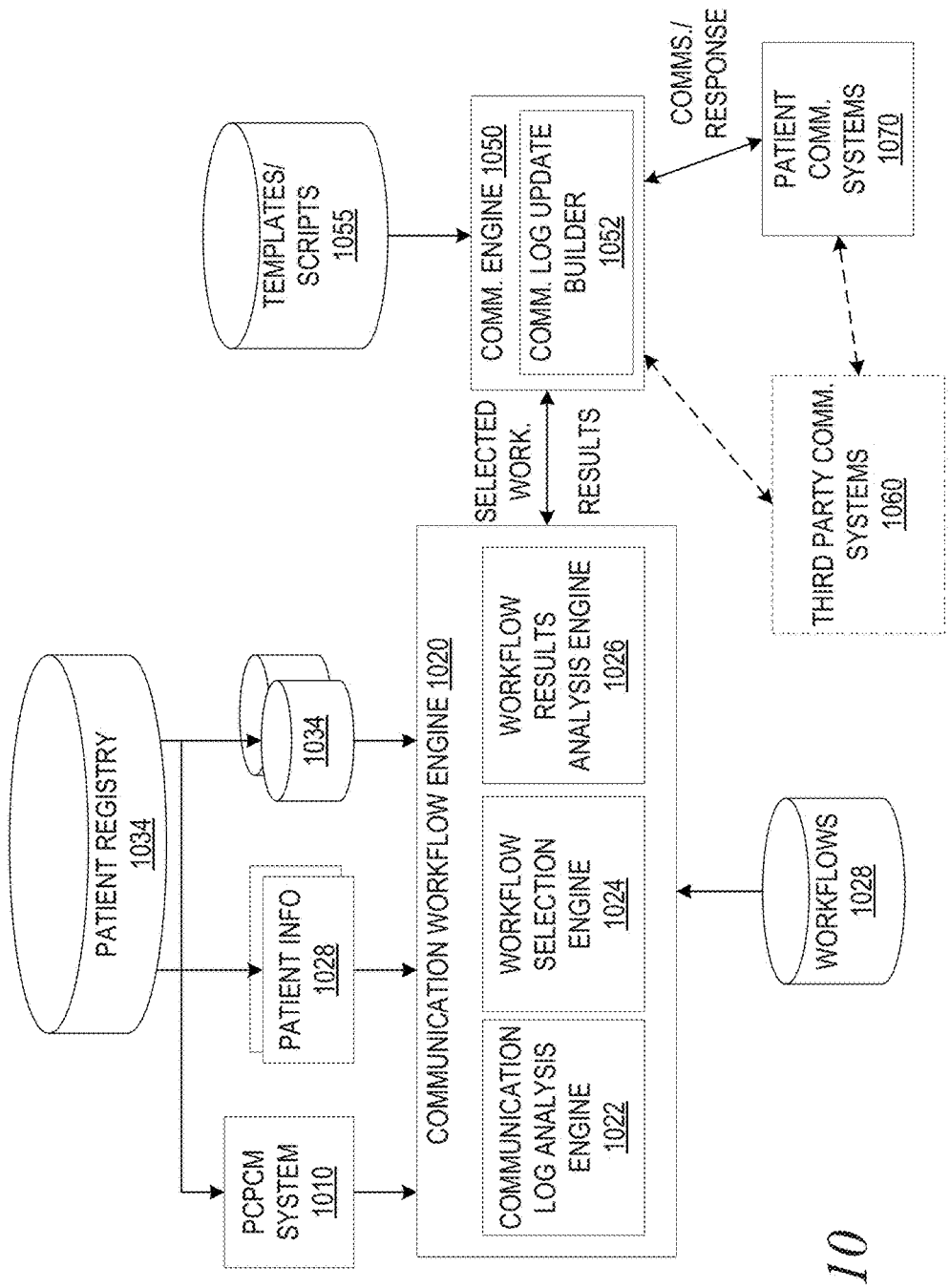
FIG. 10 is an example block diagram of the primary operational elements for selecting an optimum or best communication mode or sequence/pattern of communication modes in accordance with one illustrative embodiment.

FIG. 10 is an example block diagram of the primary operational elements for selecting an optimum or best communication mode or sequence/pattern of communication modes in accordance with one illustrative embodiment. The example shown in FIG. 10 assumes a communication workflow based implementation for purposes of illustration. However, as noted above, the illustrative embodiments do not require pre-defined communication workflows to be utilized and may in fact operate on ad hoc communication sequences/patterns identified in patient information based on pattern analysis or the like. FIG. 10 is only intended to be one example implementation and those of ordinary skill in the art will recognize that many modifications may be made to the depicted example without departing from the spirit and scope of the present invention.

As shown in FIG. 10, the primary operational elements comprise the PCPCM system 1010, a communication workflow engine 1020, a patient registry 1030, a communications engine 1050, and patient communication systems 1070. The PCPCM 1010 and patient registry 1030 operate in the manner previously described above. In addition, these elements interface with the communication workflow engine 1020 to facilitate operations for selecting one or more communication modes for contacting a non-compliant patient to elicit a compliance action/event. In particular, the PCPCM system 1010 provides information regarding non-compliant patients to the communication workflow engine 1020 and the patient registry 1030 provides patient information 1032 and communication logs 1034 for the non-compliant patient to the communication workflow engine 1020 for use in selecting a communication workflow to use to communicate with the non-compliant patient. Although communication workflow engine 1020, communication engine 1050, workflows 1028, and templates/scripts database 1055 are shown as separate entities in FIG. 10 from the PCPCM system 1010, it should be appreciated in other illustrative embodiments one or more of these entities may be integrated into the PCPCM system 1010 without departing from the spirit and scope of the illustrative embodiments.

The communication workflow engine 1020 interfaces with communication engine 1050 to facilitate the sending of communications, in accordance with a selected communication workflow, to patient communication systems 1070 and receive responses back from the patient systems 1070. In addition, the communication engine 1050 provides information back to the communication workflow engine 1020 to update communication logs 1034 associated with patient information 1032 in the patient register 1030.

In operation, the PCPCM system 1010 may identify a non-compliant patient, e.g., a patient that is not following their prescribed patient care plan, has failed to keep an appointment, or any other event that causes the patient to not be in compliance with prescribed treatments for curing or managing their medical condition. The PCPCM system 1010 may send a request message to the communication workflow engine 1020 indicating the identifier of the non-compliant patient and the nature of the failure to comply, e.g., an identifier of the type of compliance action/event that is desired from the non-compliant patient. The communication workflow engine 1020 sends a request for patient information 1032 and communication log information 1034 to the registry 1030. The patient registry 1030 provides the patient information 1032 and communication logs 1034.

The communication log analysis engine 1022 of the communication workflow engine 1020 analyzes the communication logs 1034 of the non-compliant patient to identify instances of communication workflows and their associated success/failure conditions with regard to the particular type of compliance action/event desired as specified in the request message from the PCPCM system 1010. Measures of success/failure of the various communication workflows are calculated, possibly weighting different success/failure values for different communication workflows depending on the implementation. For example, weights may be applied based on preferences, consents, or other information in the non-compliant patient's patient information to prefer some communication modes and/or communication workflows over others. In some cases, greater weight is given to communications or sequences/patterns that are more recent as opposed to those that are more temporally remote from the present date/time. Other weighting schemes may likewise be used, such as default weights set according to subject matter expert determinations, or the like.

The workflow selection engine 1024 selects a communication workflow based on the calculated success/failure measures, retrieves the corresponding communication workflow from the workflows database 1028, and provides the selected communication workflow to the communications engine 1050. The selected communication workflow is used by the communication engine 1050 to retrieve corresponding templates/scripts for the communications in the communication workflow from the templates/script database 1055. The retrieved templates/scripts are optionally customized based on patient information 1032 for the non-compliant patient to generate one or more communications to be sent to patient communication systems 1070 associated with the non-compliant patient using communication information (telephone numbers, email addresses, text message identifiers, etc.) specified in the patient's information 1032. These communications are sent using the particular communication mode(s) specified in the selected communication workflow at the specified times indicated in the selected communication workflow. Alternatively, these communications may be performed by third party communication providers 1060, such as companies that specialized in large scale automated calls, electronic mail distributions, text messaging, or the like.

The communication engine 1050 monitors the communications for results and communication log update building logic 1052 builds a communication log update based on the results. For example, the monitoring of the communications may indicate whether the results of the communications with the patient communication systems 1070 may indicate a hang-up on the call, busy signal, answering machine pick-up, auto-responder email response, email delivery failure, read receipt received, response text, user selecting a graphical user interface element (such as a virtual button or the like), or any other response that can be provided in response to a particular type of communication. This information may be added to a communication log update data structure that is provided back to the communication workflow engine 1020 in response to the workflow being completed.

The workflow results analysis engine 1026 analyzes the communication log update data structure to identify communication log updates to be applied to the communication logs 1034 of the non-compliant patient. For example, the workflow results analysis engine 1026 may analyze the various responses captured by the communication log update builder logic 1052 and determines whether these represent success/failure of the particular communication mode, communication content, and/or sequence/pattern of communications. The communication logs 1034 are then updated with the identifier of the communication workflow utilized, the date/time of the communication workflow selection and/or completion, and the success/failure of the communication workflow. Of course, this could also be done on an individual communication mode basis as well. In this way, the communication logs 1034 of the non-compliant patient are updated to reflect the most recent communication workflow attempt and thereby influence future communication workflow selections.

The PCPCM system 1010 may continue to monitor the patient registry 1020 to determine if updates to the patient information 1032 indicate a compliance action/event occurring within a specified time period of the most recent communication workflow selection/completion. The time period may be a predetermined time period which is a default or which is specific to the type of compliance action/event. If such a compliance action/event is identified, then the patient may be evaluated to be in compliance. If such a compliance action/event is not identified, then the patient may continue to be considered non-compliant and the operation to select another communication workflow may be performed again to again try to attempt to bring the patient into compliance.

Figure 11:
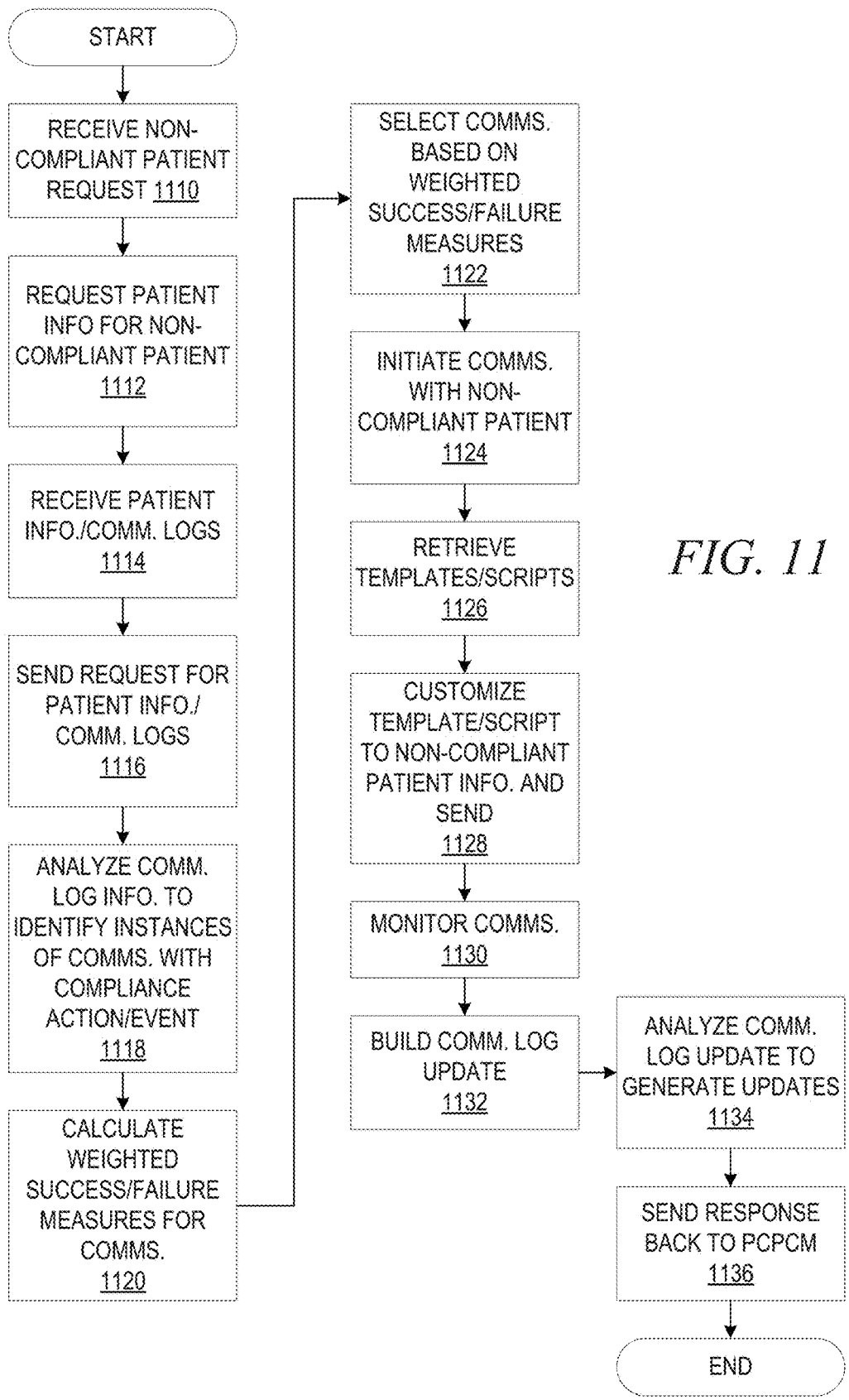
FIG. 11 is a flowchart outlining an example operation for selecting a best mode or sequence/pattern of communication modes in accordance with one illustrative embodiment.

FIG. 11 is a flowchart outlining an example operation for selecting a best mode or sequence/pattern of communication modes in accordance with one illustrative embodiment. The operation outlined in FIG. 11 may be performed, for example, by a communication workflow engine, such as communication workflow engine 1020 in FIG. 10, for example.

The communication workflow engine receives a request message identifying a non-compliant patient and a desired compliance action/event (step 1110). The communication workflow engine sends requests for patient information to the patient registry (step 1112). The communication workflow engine receives the patient information/communication logs for the non-compliant patient (step 1114) and sends a request for patient information and communication log information (step 1116).

The communication log information is analyzed to identify instances of communications of sequences/patterns of communications associated with the compliance action/event sought as specified in the request message (step 1118). Weighted success/failure measures are calculated for the various communications or sequence/patterns of communications (step 1120). A communication or sequence/pattern of communications is selected based on the weighted success/failure measures (step 1122). The selected communication(s) are then used as a basis for initiating communications with the non-compliant patient (step 1124). Corresponding templates/scripts are retrieved from a template/script database (step 1126) and optionally customized based on patient information for the non-compliant patient to generate one or more communications to be sent to communication systems associated with the non-compliant patient using communication information (telephone numbers, email addresses, text message identifiers, etc.) specified in the patient's information (step 1128).

The communications sent as part of the selected communication(s) are monitored to determine if the patient responds to the communications (step 1130). A communication log update is built based on the monitoring of the responses, if any, to indicate the success/failure of the communications (step 1132). This communication log update is analyzed to generate an update to the communication log for the non-compliant patient (step 1134) and a response is sent back to the PCPCM system indicating whether the patient responded or not (step 1136). The operation then terminates.

It should be appreciated that the PCPCM system may further monitor the patient information in the patient register to determine if there is any subsequent compliance action/event performed by the non-compliant patient to determine if the patient has come into compliance. If so, the patient may be re-classified as being a compliant patient. If not, then the process above may be repeated as the patient is still non-compliant. However, since the communication logs have been updated, the measures of success/failure may be adjusted so as to be less likely to select the same modes of communication or sequence/pattern of communications, communication workflow, and/or content of communications for subsequent communication operations.

Thus, the illustrative embodiments further provide mechanisms for selecting communication modes, sequences or patterns of communication modes, and communication content for communicating with non-compliant patients to attempt to bring them in compliance with their personalized patient care plans, treatments, or the like. The illustrative embodiments may look at the communication history of the non-compliant patient and patients having similar characteristics. Moreover, weighted calculations of success/failure of previous communications may be used to calculated values for selection of communication modes to be used. Furthermore, the selection may be based on the particular type of compliance action/event desired to be elicited from the non-compliant patient.

Continuous Health Care Plan Coordination Via Mobile Application

An important aspect of providing health care to patients with chronic medical maladies or conditions is to establish frequent, and medical condition and/or health care plan specific, communication with the patient so as to increase the likelihood that the patient will perform the recommended actions to maintain them in compliance with their health care plan. The illustrative embodiments provide additional mechanisms for facilitating continuous health care plan coordination between the patient and the patient's care team, i.e. a group of one or more human individuals that assist the patient in complying with the personalized health care plan, i.e. their personalized care plan (PCP). The patient's care team may comprise one or more assessors as previously described above which may utilize assessor systems, such as assessor systems 430, to monitor the patient's adherence to their PCP in the manner previously described above with regard to one or more illustrative embodiments and provide communication with the patient via the patient's communication device(s) 446.

The PCPCM system 410 in FIG. 4 may further include additional logic for implementing a continuous health care plan coordination engine as described hereafter which is used to coordinate the communications between the patient and the patient's care team member(s) so as to send pre-defined or ad hoc messages that are specific to the patient's current medical malady or condition, their monitored adherence to their PCP, the goals of the PCP, the patient's personal lifestyle information, and/or the like, such that the content of the messages are specific to the dynamic situation of the patient. In some illustrative embodiments in which the patient's care team comprises multiple care team members, or assessors, continuous communication may further be performed based on the dynamic assessment of the patient's situation and the identification of a care team member whose responsibility or specialization is directed to the particular situation that is a basis of the need for communication between the patient's care team and the patient. In this way, the patient is placed in communication with a particular care team member that can best assist the patient in the particular area of need of the patient as it is determined dynamically.

It should be appreciated that a care team member, or assessor, may monitor and communicate with a plurality of different patients. Thus, there is a need for a mechanism to assist the care team members with organizing and managing the various interactions the care team member has with a plurality of different patients. In some illustrative embodiments, mobile applications executed on mobile communication devices associated with the patient and/or the patient's care team members, or assessors, are provided that extend the reach of the care team member to help monitor patients and provide care to more patients.

As noted above, the assessor system(s) 430 in FIG. 4, for example, may pull in health/activity data from patient system(s) 441, such as sensor data from patient monitoring devices, e.g., smart scales, wearable monitoring devices such as FitBit™, or other Internet of Things (IoT) devices. The PCPCM system 410 generates a personalized care plan (PCP) for the patient and the care plan manager that sets forth a set of goals with regard to aspects of the patient's health (e.g., weight, diet, activity, medication, etc.). The PCPCM system 410 may utilize scripted and ad hoc messaging mechanisms to exchange messages between the system, the patient, and the care team member(s), such as via communication workflow engine 1420 and communication engine 1450, for example. The patient's communication device(s), e.g., patient communication device(s) 446, and the care team member(s) communication device(s), e.g., 434 in FIG. 4, may send/receive communications with each other and with the PCPCM system 410 via the mobile application of the illustrative embodiments. The scripts may be specific to the particular goals associated with the patient's care plan (e.g., weight, diet, activity, medication, etc.) with corresponding goal specific triggering conditions and timings.

The mobile application utilized by the patient's care team member, or assessor, communication system may utilize cognitive agents, such as described in commonly assigned and co-pending U.S. patent application Ser. No. 15/197,067, which is hereby incorporated by reference in its entirety, to facilitate automated responses to messages sent from the patient. The patient's care team member mobile application may have interface elements that allow the care team member to take over the communications in an ad hoc manner, such as in response to monitoring the patient's adherence to the patient's PCP and a particular detected deviation of the patient's monitored health/activity from the patient's PCP, monitoring of scripted or ad hoc messaging with the patient and an evaluation by the care team member that a particular response to a communication sent to the patient requires interaction with the care team member, or the like.

The PCPCM system 410 may send communications, such as via communication engine 450 in FIG. 4, to the patient's care team member(s) via the mobile application to instruct the patient's care team member regarding the communications that the patient's care team member should initiate with the patient and thereby coordinate communication between the patient and the patient's care team member. Such communications may indicate to the care team member the reasoning why the communication with the patient is needed, what the content of that communication should include, and the goals to be achieved by such communication. Moreover, the particular care team member to which the PCPCM system 410 sends the communication may be determined, from among a plurality of care team members, based on the particular responsibilities and/or specializations of the care team members compared with the particular area of need identified for the patient, e.g., if it is determined based on the monitoring of the patient's adherence to their PCP that the patient needs assistance with their diet to be in compliance with their PCP, then the PCPCM system 410 may send a communication to a care team member of the patient's care team that is a nutritionist or is responsible for assessing and communicating with the patient regarding their diet.

In some cases the communication from the PCPCM system 410 may be a command message that provides an automatic triggering of the care team member's mobile application to send automatically generated scripted or pre-defined communications to the patient's communication device to initiate or continue a communication session with the patient. In other words, the PCPCM system 410 may instruct the care team member's mobile application on their communication device to send a scripted or pre-defined communication from their device to the patient's communication device. The care team member still has the option to intercede in the communication and provide ad hoc communication with the patient as part of the communication session with the patient. Thus, a communication session with the patient may comprise automatically generated communications and/or manually generated/selected communications that are manually generated/selected by the care team member.

In some illustrative embodiments, the use of automatically generated scripted or pre-defined communications may be automatically implemented in response to a predefined time period having expired since a last communication from the patient, e.g., the patient sends a communication and the patient care team member has not been able to respond yet. In order to maintain a continuous communication session between the patient and the patient's care team member, automatically generated scripted or pre-defined communications may be sent to the patient to cause the patient to perceive that the patient's care team member is engaged in the communication session. An alert may be provided to the care team member via their mobile application on their communication device indicating a need to attend to the communication session. By providing automated communication mechanisms, communication with the patient may be maintained while the patient care team member is communicating with other patients as well, thereby allowing the patient care team member to work with a larger number of patients and continuous coordination of communications between the patient and the patient's care manager are facilitated.

In addition, to further extend the patient care team member's ability to work with a large number of patients, the mobile application may maintain separate communication sessions for each patient being managed by the patient care team member. Each separate communication session may include a communication history or log so that the care team member may review the status of the communication history at any point and be able to generate appropriate messages to send to the patient and/or PCPCM system. Management mechanisms are provided for maintaining the separate communication sessions and informing the care team member, via user interface based mechanisms, of the need to communicate with the various patients based on dynamic assessment of the communications being handled in each communication session, e.g., sending alerts when particular communication sessions have not been handled by the care team member within a specified period of time.

The mobile application may provide pre-defined communications which may be selected by the patient care team member quickly through a user interface, e.g., a menu of categories of responses with subsequent individual messages organized by particular categories of deviations of the patient from the PCP, e.g., patient is not meeting weight goal, patient is not adhering to their diet requirements, patient is not adhering to exercise requirement, etc. Pre-defined scripts or templates may be associated with each of these pre-defined communications which may be selected by the patient care team member. In some embodiments, the particular subset of communications that the patient care team member may select from may be based on the particular patient care team member's specialization or responsibilities for the particular patient, e.g., if the patient care team member is responsible for assessing the patient's adherence to their diet, then only those categories of communications associated with diet and nutrition may be made available to that the patient care team member need not sift through a large set of pre-defined communications that are not associated with their particular responsibilities or specialization with regard to assessing and communicating with the particular patient.

Figure 12:
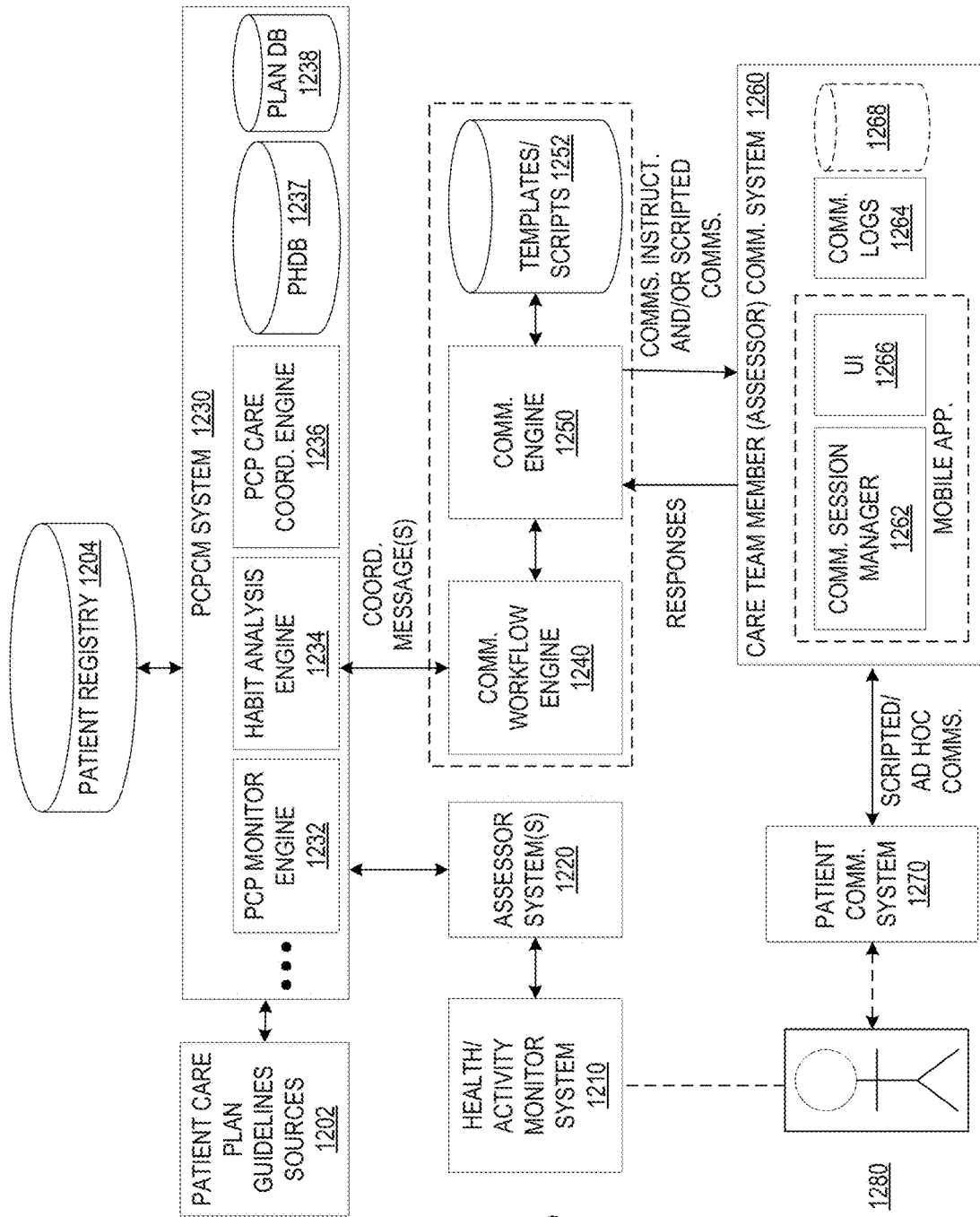
FIG. 12 is a block diagram illustrating an example interaction of elements of a personalized patient care plan system with communication system elements to achieve continuous health care plan coordination between a patient and a patient care team member in accordance with one illustrative embodiment.

To further illustrate the additional functionality and mechanisms of the illustrative embodiments directed to continuous health care plan coordination, FIG. 12 is provided herein as a block diagram illustrating an example interaction of elements of a personalized patient care plan system with communication system elements to achieve continuous health care plan coordination between a patient and a patient care team member in accordance with one illustrative embodiment. Some elements in FIG. 12 are similar to elements of previously described embodiments having similar names and thus, perform similar functions. However, additional elements, such as the habit analysis engine 1234 and PCP care coordination engine 1236, are provided and additional logic and corresponding functionality, as described hereafter, may be integrated into the other elements of FIG. 12 to facilitate interaction of these elements with the new elements of these extended embodiments and introduce new functionality in addition to, or in replacement of, the functionality of one or more of the previously described embodiments. It should be appreciated that the mechanisms and functionality described hereafter may be combined with one or more of the previously described embodiments without departing from the spirit and scope of the illustrative embodiments.

As shown in FIG. 12, the PCPCM system 1230 comprises various elements such as those previously described, not all of which are shown in FIG. 12 for the sake of focusing on the additional mechanisms and functionality provided for performing continuous PCP care coordination and habit analysis. The operation that is outlined herein with regard to FIG. 12 assumes that a patient 1280 has already had a PCP generated by the PCPCM system 1230 using the mechanisms of one or more of the illustrative embodiments previously described above. Of course, the mechanisms of the extended illustrative embodiments are not tied to the specific mechanisms for generating PCPs as described previously and other mechanisms for PCP generation may be used as a basis for the extended functionality of the habit analysis engine 1234 and PCP care coordination engine 1236 without departing from the spirit and scope of the extended embodiments.

As shown in FIG. 12, the PCPCM system 1230 comprises, among other elements not specifically depicted in FIG. 12, a PCP monitor engine 1232, a habit analysis engine 1234, a APCP care coordination engine 1236, a patient history database (PHDB) 1237, and a plan database 1238. The PCP monitor engine 1232 and plan database 1238 may operate in a similar manner to similarly labeled elements previously described above to both store PCPs for patients in plan database 1238 and to monitor a patient's adherence to their prescribed PCP. As mentioned above, other elements that are not shown in FIG. 12 for the sake of brevity and to focus on the additional functionality of the extended illustrative embodiments may include elements similar to those described above with regard to FIG. 4, for example. It is assumed for purposes of the following description that the PCPCM system 1230 has already generated a PCP for the patient 1280, based on the patient registry 1204 and patient care plan guidelines sources 1202 as well as any dynamic modifications of the PCP based on monitoring of the patient, and stored that PCP in the plan database 1238.

The PCPCM system 1230 obtains information about the patient's current condition from the health/activity monitory system 1210 associated with the patient 1280 via the assessor systems 1220 in a manner as previously described above. This information is used by the PCP monitor engine 1232 to determine the patient's adherence or deviation from the patient's prescribed PCP, e.g., the health/activity monitor system 1210 may include a smart scale which communicates the patient's current weight to the assessor system 1220 which in turn communicates that information to the PCP monitor engine 1232 of the PCPCM system 1230. The weight information may be compared to the patient's PCP to determine whether the patient is adhering to their prescribed PCP of a certain amount of weight loss per unit time, maintaining their weight within a specified range or tolerance of their previous weight or goal weight, etc.

The determination of a deviation of the patient's monitored health data and/or activity data from that expected as indicated by the patient's PCP may be communicated to the PCP care coordination engine 1236 which coordinates the communications between the patient and the patient's care team member(s) so as to send pre-defined and/or ad hoc messages that are specific to the patient's current medical condition, their monitored adherence to their PCP, the goals of the PCP, the patient's personal lifestyle information, and/or the like, such that the content of the messages are specific to the dynamic situation of the patient. That is, the PCP care coordination engine 1236 retrieves the information about the patient's medical condition and lifestyle from the patient registry 1204, and the PCP information from the plan database 1238, and uses that information in combination with the determined deviation from the patient's PCP to determine the nature and content of the communications to be sent to the patient by the patient's care team to assist the patient in becoming compliant with their PCP.

The PCP care coordination engine 1236 may determine, or be informed by the PCP monitor engine 1232, the type of the deviation of the patient from the PCP, e.g., weight loss deviation, exercise deviation, diet deviation, etc. Based on the type of deviation, the PCP care coordination engine 1236 may further evaluate the patient's lifestyle information from the patient registry 1204 to determine portions of the patient's lifestyle information that may have an effect on the deviation. The PCP care coordination engine 1236 may further analyze a patient's historical health/activity monitoring data, such as may be stored in a patient history database 1237 or the like, to perform pattern analysis to identify patterns or trends in the patient's health/activity monitoring data obtained from health/activity monitor system 1210 and logged or stored by the PCPCM system 1230. The patterns or trends identified may be correlated with the lifestyle information to identify habits as will be described hereafter, and which may be indicative of a potential cause for the deviation from the patient's PCP.

For example, if it is determined that the patient has deviated from a weight loss aspect of their PCP, and the patient supplied lifestyle information includes a food journal or log, the food journal or log may be analyzed to determine a potential reason for the deviation, e.g., the patient consumed too many calories. Moreover, historical activity tracking data for the particular time period being considered, e.g., a time period from time point when the PCPCM system 1230 evaluated the health/activity monitoring information for the patient 1280, may be retrieved from the PHDB 1237 and analyzed to determine an amount of exercise of physical activity reported to the PCPCM system 1230 by the health/activity monitoring system 1210 via the assessor systems) 1220. In this example, it may be determined that the patient did not perform enough exercise to balance the additional calories.

The PCP care coordination engine 1236 composes one or more coordination messages to be sent to the communication workflow engine 1240 that specify the identifier of the patient, the type of deviation, the amount of the deviation and the particular health/activity metric(s) which indicate the deviation, the determined reasons for the deviation based on the patient's lifestyle information and historical monitoring data, and the like. The coordination messages are sent to the communication workflow engine 1240 which performs operations similar to that described above to determine the appropriate communication workflow for the particular patient and instruct the communication engine 1250 to select or generate communications, or send communication instructions, in accordance with the communication workflow for communicating with the patient that are specific to the dynamically identified deviation of the patient from the patient's PCP. It should be appreciated that this may be a continuous or periodic operation performed based on the continuous or periodic obtaining of health/activity monitoring data from the health/activity monitoring system 1210 associated with the patient 1280.

It should be appreciated that the health/activity monitoring system 1210 may send health/activity monitoring data to the assessor system(s) 1220 which are then provided to the PCP monitor engine 1232 and which indicate multiple different types of deviations of the patient from the patient's prescribed PCP. Thus, the PCP care coordination engine 1236 may be required to evaluate multiple different types of deviations and send appropriate coordination messages to coordinate communication between the patient and the care team members regarding a plurality of different types of deviations.

In some illustrative embodiments in which the patient's care team comprises multiple care team members, or assessors, continuous communication may further be performed based on the dynamic assessment of the patient's deviation(s) and the identification of a care team member whose responsibility or specialization is directed to the particular deviation(s) which are a basis of the need for communication between the patient's care team and the patient. That is, in establishing a patient's PCP as discussed above, the PCP may include assessor plans as well. These assessor plans may be generated identifying a particular care team that is to be associated with the patient, where the care team comprises one or more care team members. Information regarding the particular care team assigned to the patient may be stored in association with the PCP in the plan database 1238. This information may include identifiers of the care team member(s), or assessors, each care team member's specialization or responsibilities for monitoring and/or communicating with the patient, and other information used to establish communications with the care team member. Thus, when determining a deviation of the patient from the PCP, the particular care team member whose specialization or responsibilities are associated with the type of deviation may be identified based on a mapping of deviation type to care team member specialization or responsibility maintained in a configuration data structure (not shown) of the PCP care coordination engine 1236. In this way, the coordination messages may further indicate the particular care team member that should interact with the patient. Thus, the patient is placed in communication with a particular care team member that can best assist the patient in the particular area of need of the patient as it is determined dynamically.

In response to receiving the coordination message(s) from the PCPCM system 1230, the communication workflow engine 1240 selects a communication workflow for the particular patient identified in the coordination message(s). The communication engine 1250 may further select appropriate templates/scripts for communications based on a matching of the information included in the coordination message(s) with characteristics of the templates/scripts 1252 and insert information specific to the patient and/or the patient's current condition and/or the determined deviation into appropriate portions of the templates/scripts. For example, various templates/scripts 1252 may be established for various different deviation types. Based on the deviation type indicated in the coordination message(s), a corresponding template/script 1252 may be selected and populated with information from the patient registry 1204 about the patient, the particular deviation as indicated in the coordination message(s), or the like. These constructed communications, or scripted communications, may then be sent to the identified care team member's communication system 1260 along with a command to cause the care team member's communication system 1260 to transmit the scripted communication to the patient communication system 1270 as part of a newly generated or previously existing communication session between the care team member's communication system 1260 and the patient communication system 1270.

In some cases, rather than automatically selecting a template/script 1252 and populating it for automatic transmission by the care team member communication system 1260 to the patient communication system 1270, the communication engine 1250 may instead send a communication instruction to the care team member communication system 1260 which may be output to the care team member via an output device of the communication system 1260 to inform the care team member of a need to communicate with the patient 1280 regarding the specified deviation. The communication instruction may specify the deviation type and other information included in the coordination message(s) from the PCPCM system 1230, and may further provide information regarding the selected communication workflow for communicating with the patient 1280. Based on the communication instructions, the care team member may interact with their communication system 1260 to select templates/scripts for sending to the patient communication system 1270 or generate ad hoc communications for sending.

The care team member (or assessor) communication system 1260 comprises a communication session manager 1262, a communication logs database 1264, a user interface engine 1266, and optionally a set of local templates/scripts 1268 which may be selectable by the care team member to facilitate communication with the patient communication system 1270. The set of local templates/scripts 1268 are optional in that in some illustrative embodiments the communication workflow engine 1240, communication engine 1250, and templates/scripts 1252 may in fact be integrated into the care team member communication system 1260, in which case the optional set of local templates/scripts 1268 may in fact be the templates scripts 1252. In other illustrative embodiments, these elements 1240-1252 are not integrated into the care team member communication system 1260 and thus, to facilitate ease of communication with the patient communication system 1270, a set of local templates/scripts 1268, which may be the same as or different from the templates/scripts 1252, may be provided in the care team member communication system 1260. It should further be appreciated that in some illustrative embodiments, one or more of the elements 1240-1252 may be integrated into the PCPCM system 1230 or may be executed using a separate computing system.

The communication session manager 1262 of the care team member communication system 1260 provides the logic for managing a communication session with the patient 1280 via their patient communication system 1270. The particular type of communication session may be dependent upon the particular type of communication currently being utilized as part of the selected communication workflow, e.g., email, instant messaging, telephone calls, etc. The communication session manager 1262 is responsible for establishing communications, monitoring communications, logging communications in the communication logs database 1264, and the like. The communication session manager 1262 may manage communication sessions with a plurality of different patient communication systems 1270 associated with a plurality of different patients 1280.

In managing communication sessions, the communication session manager 1262 may further identify instances where a care team member's attention to a particular communication session is warranted. For example, the communication session manager 1262 may monitor communication sessions for responses from patients 1280 received from the patient communication systems 1270. In response to a patient's response message being received, a time period since receiving the response message may be monitored by the communication session manager and if the time period meets or exceeds a threshold time without a subsequent communication being sent to the patient communication system 1270, and the communication session is still active, then a corresponding action may be taken to continue the communication so that the patient 1280 perceives the communications between the patient and the care team member to be a continuing conversation. The action may be to send a scripted communication to the patient communication system 1270 and/or to alert the care team member via a user interface generated by the user interface (UI) engine 1266 indicating that the care team member's attention is needed for the particular communication session. In the case of a scripted communication, the scripted communication may be selected from the local set of templates/scripts 1268 based on an analysis of keywords and phrases in the last response from the patient communication system 1270 in the communication session, e.g., a natural language processing of the response communication may be performed and the key terms/phrases extracted which are then matched to key terms/phrases associated with the templates/scripts 1268 with the selection of a highest ranking template/script 1268, e.g., a template/script that has the most matching key terms/phrases.

The communication logs database 1264 stores a history of the communications and their content exchanged with the patient 1280 for a particular communication session. The communication logs database 1264 may store separate communication logs for separate communication sessions with different patient communication systems 1270. The communication logs provide the care team member the ability to review the communications exchanged with the patient 1280 to determine an appropriate follow-on communication to be sent to the patient 1280. Thus, the communication log may be output to the care team member for review, such as via a user interface of the communication system 1260.

The user interface (UI) engine 1266 provides the logic for generating user interfaces for the care team member which may be output on an output device (not shown) associated with the communication system 1260. The UI engine 1266 may generate UIs that output details of communication logs 1264 and provide logic for alerting the care team member of the need for their attention or interaction with a particular communication session, as indicated by the communication session manager 1262, e.g., by highlighting particular communication sessions in a UI, generating a pop-up message, automatically opening or activating a portion of the UI associated with the particular communication session, or the like. Moreover, the UIs may include user selectable elements to allow the care team member to provide ad hoc communications which are sent to the patient communication system 1270. For example, the care team member may determine from reviewing the communication log that personal intervention in the communication session is required and may override scripted communication and provide an ad hoc message that is sent to the patient communication system 1270. Thus, a communication session between the patient communication system 1270 and the care team member communication system 1260 may comprise one or both of scripted communications and ad hoc communications from the care team member communication system 1260.

In some illustrative embodiments, one or both of the patient communication system 1270 and care team member (or assessor) communication system 1260 are mobile communication devices, such as tablet computers, smart phone devices, or the like. As such, mobile applications may be provided and executed on these mobile communication devices 1260, 1270 associated with the patient and/or the patient's care team members and thus, the communication session manager 1262 and user interface engine 1266 may be provided as part of a mobile application which interacts with communication logs database 1264 and optionally local templates/scripts 1268 stored on the mobile communication device 1260. As mentioned above, the mobile application executed by the care team member communication system 1260 may utilize cognitive agents, such as described in commonly assigned and co-pending U.S. patent application Ser. No. 15/197,067, filed Jun. 29, 2016, to facilitate automated responses to messages sent from the patient communication system 1270. Moreover, as noted above, the patient's care team member mobile application may have interface elements that allow the care team member to take over the communications in an ad hoc manner.

The PCPCM system 1230 may send coordination messages, such as via communication engine 1250, to the patient's care team member via the mobile application to instruct the patient's care team member regarding the communications that the patient's care team member should initiate with the patient and thereby coordinate communication between the patient and the patient's care team member. Such communications may indicate to the care team member the reasoning why the communication with the patient is needed, what the content of that communication should include, and the goals to be achieved by such communication, e.g., the patient has deviated from their weight loss goal of their PCP by not losing 2 pounds this week, the patient's food log indicates ingestion of too many calories according to their PCP, the patient's activity monitoring indicates not enough activity to accommodate the additional calories, nutritionist needs to communicate with patient about ingesting fewer calories and/or increasing activity in order to achieve 2 pound loss goal.

As noted above, in some cases the communication from the PCPCM system 1230 via the communication engine 1250 may be a command instruction that provides an automatic triggering of the care team member's mobile application to send automatically generated scripted or pre-defined communications, such as may be selected from templates/scripts 1252 and/or 1268, to the patient's communication system 1270 to initiate or continue a communication session with the patient. The care team member still has the option to intercede in the communication session and provide ad hoc communications with the patient as part of the communication session with the patient via their user interface(s) generated by the UI engine 1266. The user interface(s) generated by the UI engine 1266 may further provide UI elements, such as menus, buttons, and the like, through which the care team member may select pre-defined communications for transmission to the patient communication system 1270, e.g., a menu of categories of responses with subsequent individual messages organized by particular categories of deviations of the patient from the PCP, e.g., patient is not meeting weight goal, patient is not adhering to their diet requirements, patient is not adhering to exercise requirement, etc. Predefined scripts or templates in local templates/scripts 1268 may be associated with each of these pre-defined communications which may be selected by the patient care team member. In some embodiments, the particular subset of communications that the patient care team member may select from may be based on the particular patient care team member's specialization or responsibilities for the particular patient, as discussed above.

Thus, the illustrative embodiments may further comprise mechanisms for implementing and managing communication sessions between a mobile application of a care team member and one or more patient communication systems 1270 of patients 1280 being monitored by the care team member. The illustrative embodiments provide two separate levels of communication management. A first level of communication management exists at the PCPCM system 1230 which determines deviations of a patient from their prescribed PCP based on data obtained from health/activity monitoring system 1210 associated with the patient 1280, which may include wearable health/activity monitoring devices, health/activity log applications executing on a computing device associated with the patient 1280, e.g., on patient communication system 1270, or the like. Based on the detected deviation(s), the PCPCM system 1230 coordinates communication between the patient's care team and the patient, and in some cases, a particular patient care team member and the patient based on a correlation of the deviation with the care team member's specialization or responsibilities within the patient care team.

The results of this first level of communication management are sent to a second level of communication management which exists in the care team member communication system 1260. This second level of communication management involves the management of one or more communication sessions between a mobile application executing on the care team member communication system 1260 and one or more patient communication systems 1270. In addition, this second level of communication management involves the selection of predefined templates/scripts for communicating with the patient communication system 1270 and the patient 1280 and/or the providing of ad hoc communications by the care team member. It should be appreciated that the interaction between the first level of communication management and the second level of communication management may be facilitated by a communication workflow engine 1240 and/or communication engine 1250.

Figures 13A, 13B:
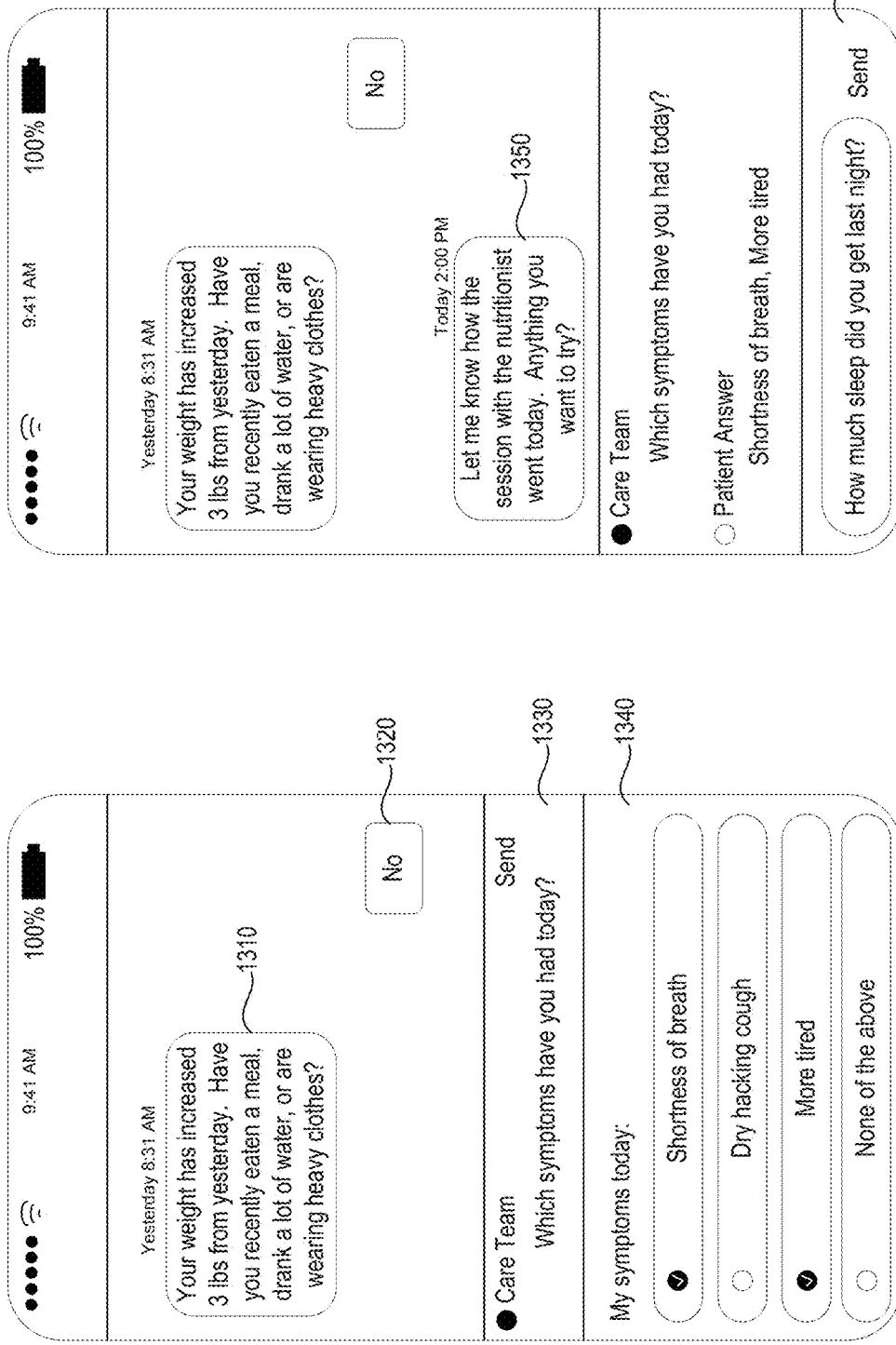
FIGS. 13A-13B are example diagrams of a mobile application interface through which communication between a patient and a patient care team member communication system is provided in accordance with one illustrative embodiment.

FIGS. 13A-13B are example diagrams of a mobile application interface through which communication between a patient and a patient care team member communication system is provided in accordance with one illustrative embodiment. It should be appreciated that the diagrams shown in FIGS. 13A-13B are for a communication session between a single patient and a corresponding care team member communication system. Similar diagrams may be provided for situations in which multiple communication sessions with multiple patients are being handled by a care team member communication system and managed via a communication session manager as discussed above. The care team member communication system's mobile application interface may have a plurality of such user interface displays similar to what is shown in diagrams 13A-13B and may alert or otherwise bring the attention of the care team member to the particular ones that need the care team member's intervention based on evaluations of the dynamic patient data and/or responsive communications as mentioned above.

FIG. 13A illustrates an example communication interface from the perspective of a patient's mobile communication device using a mobile application in accordance with one illustrative embodiment. As shown in FIG. 13A, the communication exchange depicted shows a message 1310 from the care team member's computing device asking the patient about a recent increase in the patient's weight. This message may be an automatically generated (scripted) or manually generated by the care team member, however the patient's interface does not distinguish between whether the message 1310 is automatically generated or manual. The patient may response to the message 1310 with their responsive message 1320 as if the patient is speaking with a human being, which they may or may not be depending on the particular timing during the communication session. Thus, the patient has the perspective that the messages 1310, 1320 that are being exchanged are with a human being even though there may be a mixture of automated and manually generated messages such that the human care team member only periodically interfaces with the patient while other times the automated system performs the communications.

In addition to the portion of the interface in which the communications 1310, 1320 are depicted, the interface further comprises a section 1330 via which scripted questions may be posed to the patient with structured responses 1340 being provided for selection by the patient. For example, it may be determined based on evaluation of the patient's data, lifestyle information, deviations from PCP, etc., that the system should inquire with the patient as to their current symptoms and specifically with regard to symptoms that are directed to the particular patient's medical condition, deviations from the patient's PCP, and the like. The patient may select the symptoms that apply and press the "Send" element to send this information.

FIG. 13B illustrate an example communication interface from the perspective of the cate team member's mobile communication device using a mobile application in accordance with one illustrative embodiment. As shown in FIG. 13B, the system has generated and sent a responsive message 1350 to the patient, which is a scripted message based on information in the patient's data indicating that the patient has an appointment with a nutritionist. Again, the communication 1350 appears to be originating from a human being rather than automated, from the perspective of the patient. In addition, the patient's response to the request regarding symptoms is shown to the care team member. In response to the patient's answer, the care team member may interject a manually generated question via interface elements 1360 which allow the care team member to compose their own communication and send it to the patient's communication device. The question may be posed to the patient as another communication similar to 1310 in FIG. 13A but without any designation that the question was manually generated, thereby maintaining the appearance that all of the communications are with a human being care team member.

Figure 14:
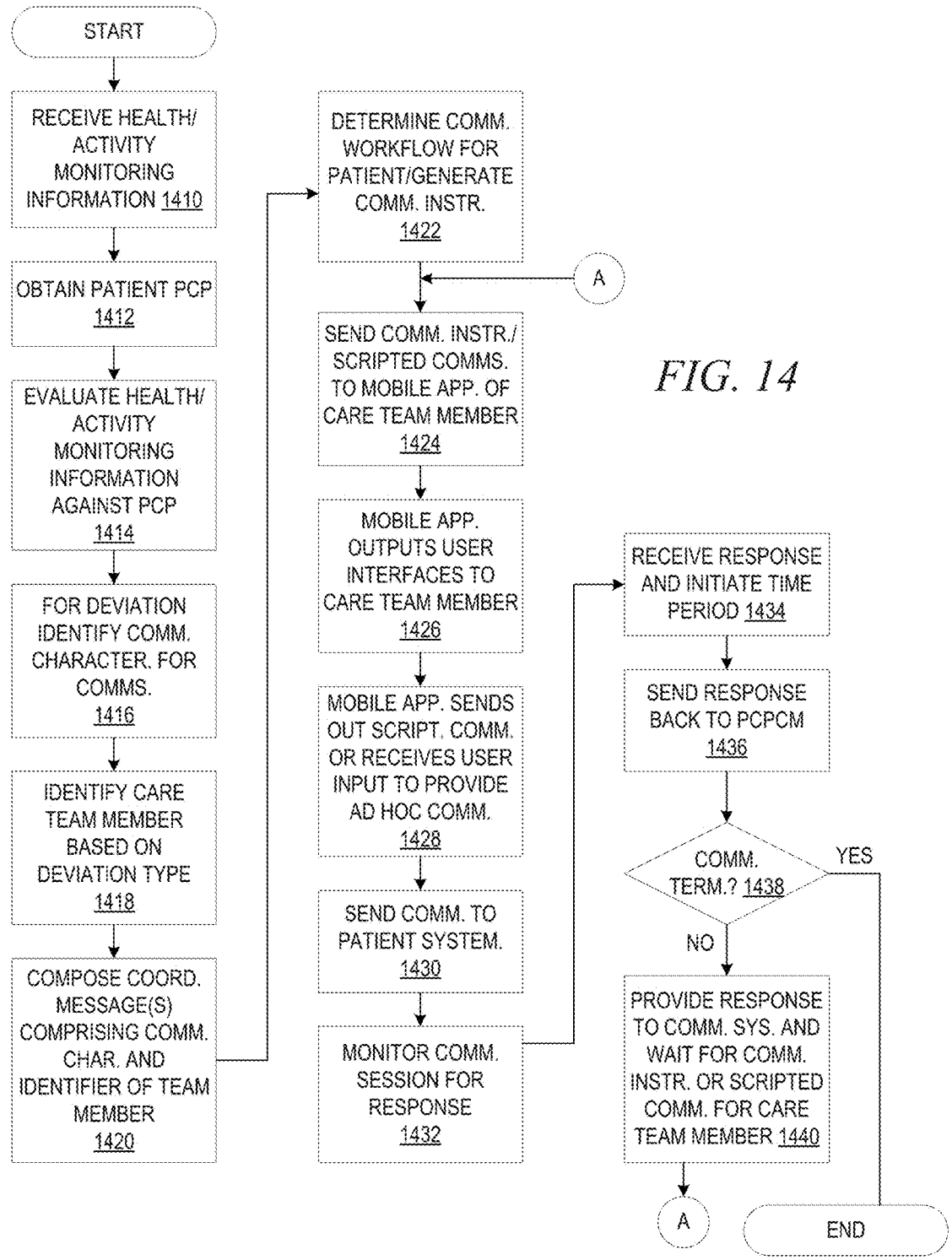
FIG. 14 is a flowchart outlining an example operation for performing continuous patient care plan coordination between a patient and a care team member in accordance with one illustrative embodiment.

FIG. 14 is a flowchart outlining an example operation for performing continuous patient care plan coordination between a patient and a care team member in accordance with one illustrative embodiment. The operation outlined in FIG. 14 may be implemented by a combination of care coordination logic of the PCPCM system, such as the PCP care coordination engine 1236 in FIG. 12, for example, and a mobile application executing on a care team member communication system, such as the mobile application executing on care team member communication session 1260 in FIG. 12.

As shown in FIG. 14, the operation starts by receiving health/activity monitoring information from a health/activity monitoring system associated with a patient (step 1310). A PCP for a patient corresponding to the health/activity monitoring information is retrieved (step 1412) and the health/activity monitoring information is evaluated against the PCP to identify any deviations between the monitored health/activity information and the PCP of the patient (step 1414). For a detected deviation, the patient's lifestyle information, patient history information, and the like are analyzed along with the deviation information to identify communication characteristics for communications that are to be sent by a care team member communication system to a communication system of the patient (step 1416). The communication characteristics comprise information specifying the deviation type, the metrics that are the source of the deviation, the reasons for the deviation as determined from patient lifestyle information, goals to be achieved by the communication, and the like.

Based on a determined deviation type of the deviation, a particular care team member in the care team assigned to the patient is selected to perform the communication (step 1418). As noted above, the selection may be based on a matching or mapping of deviation type with a specialization or responsibility associated with care team members in the care team to thereby select a care team member whose specialty or responsibility matches the problem area or need of the patient with regard to their deviation from their prescribed PCP.

One or more coordination messages are composed, comprising the communication characteristics information and the identification/communication information for the selected care team member, and sent to a communication system (step 1420). The communication system may determine an appropriate communication workflow to utilize to communicate with the patient and may select one or more templates/scripts to utilize when communicating with the patient (step 1422). Alternatively, the communication system may generate communication instructions to inform a care team member of the types of communications the care team member should perform with the patient, or which automatically cause the care team member communication system to transmit predefined template/scripted communications to the patient communication system.

The communication instructions and/or scripted communications are sent to the care team member communication system executing a mobile application for managing communication sessions with one or more patient communication systems (step 1424). The mobile application receives the instructions/scripted communications and outputs one or more user interfaces to the care team member for monitoring the communication session with the patient communication system (step 1426). Depending on the nature of the instructions/scripted communications, the mobile application either sends out a predefined scripted communication to the patient communication system automatically or receives user input to provide an ad hoc communication or selection of a predefined template/script from a local template/script database (step 1428). The communication is sent to the patient communication system (step 1430) and the communication session is monitored for a response from the patient (step 1432). If a response is received from the patient, a time period between the response and a subsequent communication from the care team member is monitored (step 1434). In response to the time period reaching or exceeding a threshold, the mobile application alerts the care team member of the need for attention to the communication session (step 1436).

A determination is then made as to whether or not the communication session has been terminated (step 1438). If not, the operation provides the response from the patient to the communication system and waits for a communication instruction and/or scripted communication to be provided by the communication system or the care team member to continue the communication (step 1440). The operation then returns to step 1424. Otherwise, if the communication session has been terminated, the operation ends with regard to the communication session but may be repeated with regard to other communication sessions that may be managed by the mobile application of the care team member communication system.

Thus, in addition to the mechanisms for generating, monitoring, and modifying a patient's personalized care plan and selecting the best communication modes for communicating with a patient, the illustrative embodiments may further provide mechanisms for providing continuous coordination of communications between a patient and one or more care team members of the patient's assigned care team. In some illustrative embodiments a method, computer program product, and/or apparatus are provided in which a personalized health care management system receives a personalized health care plan for a patient and dynamic patient monitoring data from one or more patient monitoring devices associated with the patient. The personalized health care management system analyzes the dynamic patient monitoring data to identify at least one pattern of dynamic patient monitoring data representing a habit of the patient. The personalized health care management system generates desired pattern data based on results of the analysis, where the desired pattern data represents at least one desired habit for the patient. The personalized health care management system also determines at least one communication to output to the patient via a patient computing device or patient communication device to elicit conformance of the patient with the at least one desired habit based on the generated desired pattern data and the personalized health care plan. Moreover, the personalized health care management system outputs the at least one communication to the patient computing device or patient communication device.

In some illustrative embodiments, the personalized health care plan comprises at least one health goal of the patient. In such a case, the desired pattern data is generated based on an analysis of the at least one pattern of dynamic patient monitoring data and the at least one health goal of the patient.

In some illustrative embodiments, the personalized health care management system analyzes the dynamic patient monitoring data to identify at least one pattern of dynamic patient monitoring data representing a habit of the patient at least by correlating the dynamic patient monitoring data with patient lifestyle information to identify a cause for a deviation of the dynamic patient monitoring data from expected patient monitoring data corresponding to the personalized health care plan for the patient. In some embodiments, the patient lifestyle information comprises at least one of first patient lifestyle information defining activity performed by the patient over a specified period of time or second patient lifestyle information defining consumption by the patient over a specified period of time.

With some illustrative embodiments, the personalized health care management system continuously receives dynamic patient monitoring data over a specified period of time and performs the analyze, generate, determine, and output operations in response to receiving new dynamic patient monitoring data during the specified period of time. Furthermore, in some embodiments, the determining at least one communication to output comprises determining a difference between the desired pattern data and the at least one pattern of dynamic patient monitoring data, and determining a communication to be output to the patient that is directed to minimizing the difference between the desired pattern data and the at least one pattern of dynamic patient monitoring data.

It should be appreciated that in some embodiments, the at least one communication is a pre-defined scripted communication associated with the at least one health goal and the at least one desired habit. Moreover, in some embodiments, the at least one communication is an ad hoc communication between the patient and a human patient care manager.

Furthermore, the personalized health care management system may operate to determine at least one second communication to output to a care plan manager computing device associated with a human patient care manager associated with the patient, where the at least one second communication provides instructions to the human patient care manager to facilitate interaction between the human patient care manager and the patient that will elicit conformance of the patient with the at least one desired habit. The personalized health care management system may also output the at least one second communication to the care plan manager computing device. In some illustrative embodiments, the personalized health care management system determines at least one second communication to output at least by determining a type of difference between the desired pattern data and the at least one pattern of dynamic patient monitoring data and identifying a care plan manager associated with the patient whose specialization or responsibilities are directed to the type of difference. The at least one second communication may be output to the identified care plan manager.

Detection of Habits and Eliciting of Desired Habits

Returning to FIG. 12, the PCPCM system 1230 may further include a habit analysis engine 1234 which operates on currently obtained data from the various health/activity monitoring devices, such as may be obtained by health/activity monitoring system 1210 in FIG. 12, and patient history information stored in the patient history database 1237, to identify trends and patterns in the patient's monitored health metrics and/or activity metrics. Moreover, the habit analysis engine 1234 may analyze lifestyle information, e.g., food logs, activity logs, EMR data, and the like, from the patient registry 1204 to identify habits apparent in a pattern of behavior of the patient, e.g., the food logs and activity logs may indicate patterns in food/drink ingestion and activities performed by the patient. This information may be correlated by the habit analysis engine 1234 with data indicating habits that would be beneficial for the patient based on the goals of their particular personalized care plan.

That is, the habit analysis engine 1234 may access resource data structures, such as resources 418 in FIG. 4, that store information about particular predefined habits and their correlation with one or more personalized care plan (PCP) goals and/or deviation types from the one or more PCP goals. The particular desirable habit information for goals associated with the particular patient's PCP may be retrieved from the resources 418 and used by the habit analysis engine 1234 to evaluate the patient's actual habits as indicated from pattern analysis of the health/activity information obtained from the health/activity monitoring system 1210, stored in the patient history database 1237, and lifestyle information for the patient indicated in the patient registry 1204. Moreover, the particular desirable habit information retrieved may be specific to a detected deviation of the patient's health/activity monitoring information identified by the PCP monitor engine 1232 in the manner previously described above. Thus, for example, the PCP monitor engine 1232 may determine, based on health/activity monitoring information from system 1210, such as a smart scale, that the patient has not lost weight in accordance with their PCP. Thus, the deviation type is a weight loss deviation type. This deviation type may then be used to identify a set of one or more desirable habit information entries in the resources 418 that correspond to that deviation type. e.g., weight loss.

In some illustrative embodiments, a particular desirable habit and corresponding desirable habit information entry in the one or more desirable habit information entries, to be utilized for communicating with the patient may be selected using a sorting algorithm that leverages insights from multiple inputs, such as similarity analytics, personal preferences, organizational preferences, geo location, and the like. The particular desirable habit may be selected from the set and used to communicate with the patient to elicit the patient adopting the desirable habit. If the patient does not adopt the selected desirable habit, the next desirable habit in the set may be selected to replace the previous selected desirable habit, and the process is repeated until either the patient adopts a desirable habit or all of the desirable habits in the set have been tried. It should be appreciated that the selection may be automated based on the analytical scoring generated by evaluating the insight inputs and/or manual in that the patient may select which desirable habit they wish to attempt to adopt. Of course a combination of automated and manual processes may also be utilized.

The desirable habit information may comprise a variety of desirable habits for achieving particular goals of a PCP and there may be multiple desirable habits for achieving the same goal. Thus, when retrieving desirable habit information for a particular patient, a set of desirable habit information may be retrieved for a particular goal of the patient's PCP. For example, a habit of eating smaller meals more frequently may be associated with a goal of weight loss, a habit of checking blood sugar levels may be associated with a goal of managing a diabetes condition, a habit of taking medication after every meal may be associated with a goal of achieving medical condition management through proper administration of medication, etc. These desirable habits may have associated attributes which indicate patient health metric patterns, activity metric patterns, lifestyle information patterns, and the like, that are indicative of a patient achieving a desirable habit. These desirable habit attributes may be compared to actual habit pattern data for patient to determine whether the patient is exhibiting the desirable habit or not.

The actual habit pattern data may be obtained, as noted above, through analysis of health/activity data from the health/activity monitoring system 1210, lifestyle information stored in the patient registry 1204, and previously stored health/activity data and/or lifestyle information stored in the patient history database 1237. The information in the patient history database 1237 provides a historical set of data which can be analyzed using pattern analysis techniques to identify patterns and trends with regard to particular health/activity information metrics, lifestyle information changes and the like. For example, multiple instances of readings of a patient's weight may be used to identify a pattern in which the patient's weight fluctuates over particular time periods, trends indicating increasing or decreasing weight over time, or the like. This information may be used and correlated with other lifestyle information to identify habits of the patient, e.g., the weight metrics indicate that the patient loses weight slightly during the week but gains weight on weekends and the lifestyle information comprising food logs and activity logs indicates that the patient eats more on the weekends, skips meals during the week, and has less activity during the week indicating a habit to overeat on the weekend and be sedentary during the week.

Differences between the patient's actual habits and the desired habits are then identified by the habit analysis engine 1234 and corresponding actions to bring the patient's existing habits in conformance with the desired habits may be identified. Thus, for example, if the patient's actual habit is to eat more calories on weekends and skip lunch on weekdays, and the desired habit is to eat smaller meals more often, then the habit analysis engine 1234 may determine that the difference is that the patient is currently eating less often and larger meals having more calories per meal. Thus, actions would require reducing the size of the current meals, adding small lunchtime meals during weekdays, and adding additional small meals at specified times periods during the day to each of the days. The result is that the patient will tend to be less hungry during the day and may consume fewer calories over all as a result leading to weight loss.

It should be appreciated that the above is just one example of good habits that may be adopted via the mechanisms of the illustrative embodiments and the present invention and illustrative embodiments are not limited to such. Various other types of good habits may be utilized as well depending on the particular patient medical condition, personalized care plan, goals, etc. For example, other good habits that may be elicited via the mechanisms of the illustrative embodiments may be taking medications, improving diet, increasing or maintaining an exercise regimen, performing range of motion exercises, performing required blood pressure monitoring operations, performing blood glucose monitoring, etc. Good habits are those that promote health, wellness, are in support of evidence based medicine, or that support items of the patient's personalized care plan or otherwise assist the patient in achieving the goals of the personalized care plan.

The information regarding habits and actions to adjust the behavior of the patient with regard to their existing habits to be in conformance with desired habits may then be provided to the PCP care coordination engine 1236 for use in coordinating communications between the patient's care team and the patient. For example, the PCP care coordination engine 1236 may utilize this habit information along with other information as discussed above to select a care team member that has a specialization or responsibility within the care team that matches the particular type of habit that is attempting to be adjusted. In addition, the habit information may be used to populate information in coordination messages to inform the care team member of the habit information, the reason that the care team member is to communicate with the patient, and the desired outcome of the of the communication, e.g., the patient is not meeting their weight loss goal and has the habit of gaining weight on the weekends but then losing weight during weekdays, from the patient lifestyle information the patient shows a habit of eating excess calories on the weekend and skipping mid-day meals during weekdays, to conform to the PCP it is desirable to adjust the patient's habit to eat fewer calories on the weekend and incorporate mid-day meals during weekdays.

Thus, the habit analysis engine 1234 identifies patterns that represent habits of the patient which may or may not be beneficial to the patient's overall health and the particular goals associated with that patient's personalized care plan. The patterns may be analyzed to identify ways in which the patterns may be adjusted to cause the patient to perform actions that will result in desirable habits, i.e. minimize the difference between detected habits of the patient and desired habits of the patient that will assist the patient in achieving the goals associated with their personalized patient care plan. Thus, the detected patterns (or habits) may be leveraged by the personalized patient care plan to generate and/or exchange messages with the mobile application to customize the activities in the personalized patient care plan and the care manager plan, in view of the detected habits, to try to elicit the desirable habits for the patient. The messaging is coordinated between the mobile application and the patient's associated care team. In this way, a continuous care management system is provided that dynamically learns the habits of the patient, determines the desired habits related to the patient's current habits that will assist the patient in achieving the goals of their personalized patient care plan, and generates and coordinates the messaging, of various types, between the mobile application used by the patient and the care team.

Figure 15:
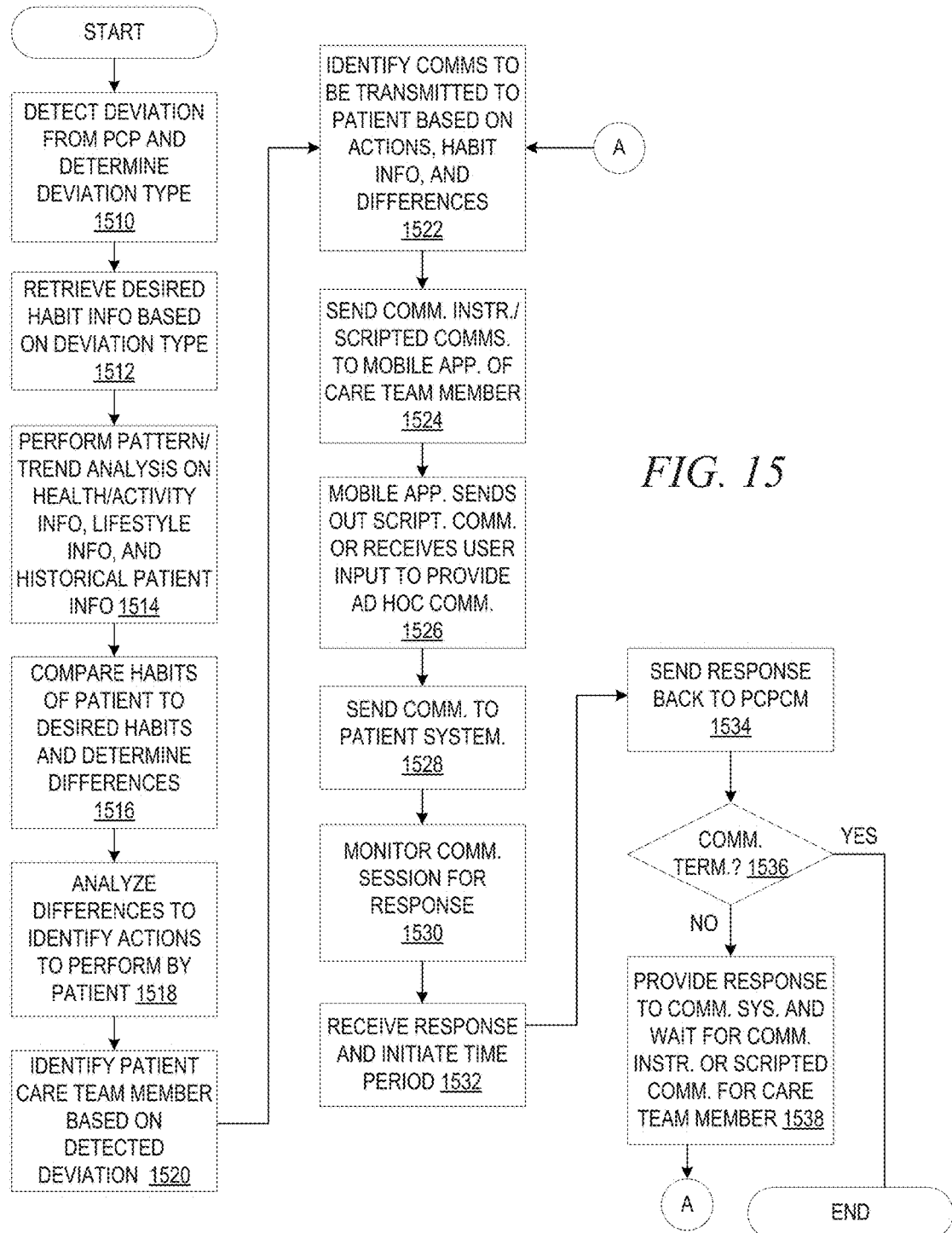
FIG. 15 is a flowchart outlining an example operation for performing habit analysis and patient communication in accordance with one illustrative embodiment.

FIG. 15 is a flowchart outlining an example operation for performing habit analysis and patient communication in accordance with one illustrative embodiment. The operation outlined in FIG. 15 may be implemented by logic configured to perform pattern/trend analysis on data to identify habits of a patient, such as, for example, pattern/trend analysis performed by the habit analysis engine 1234 in FIG. 12 based on data obtained from the health/activity monitoring system 1210, the patient registry 1204, and stored patient history information in the PHDB 1237. The depicted example, in FIG. 15 assumes an implementation in which the operation is initiated based on a determination of a deviation of the health/activity information of the patient from the patient's prescribed PCP, with the habit analysis being directed to habits associated with the particular deviation.

As shown in FIG. 15, the operation starts by detecting a deviation in the patient's health/activity information from the patient's prescribed PCP (step 1510). The identification of the deviations as well as gathering information about the deviation, such as deviation type, health/activity metrics involved in the deviation, and the like, may be performed in a similar manner to that described previous, such as with regard to FIG. 14, for example. The deviation type is used to identify and retrieve a set of one or more desired habit entries corresponding to the particular deviation type (step 1512). Pattern/trend analysis is performed on the health/activity information gathered from the health/activity monitor system, the lifestyle information in the patient registry, and historical patient information obtained from the PHDB to thereby the habit(s) of the patient (step 1514). The habit(s) of the patient are compared to the desired habit(s) for the particular deviation and differences are identified (step 1516). The differences are analyzed to identify actions that may be performed by the patient to bring their current habits closer to conformance with the desired habits (step 1518). A particular patient care team member whose specialization or responsibilities map to the detected deviation from the PCP may be identified (step 1520). Moreover, the habit information, differences information, and actions information may be utilized to identify one or more communications to be transmitted from a patient care team member to the patient's communication device (step 1522). Communication instructions and/or scripted communications may be sent to a mobile application of the patient care team member's communication device (step 1524).

Depending on the nature of the instructions/scripted communications, the mobile application either sends out a predefined scripted communication to the patient communication system automatically or receives user input to provide an ad hoc communication or selection of a predefined template/script from a local template/script database (step 1526). The communication is sent to the patient communication system (step 1528) and the communication session is monitored for a response from the patient (step 1530). If a response is received from the patient, a time period between the response and a subsequent communication from the care team member is monitored (step 1532). In response to the time period reaching or exceeding a threshold, the mobile application alerts the care team member of the need for attention to the communication session (step 1534).

A determination is then made as to whether or not the communication session has been terminated (step 1536). If not, the operation provides the response from the patient to the communication system and waits for a communication instruction and/or scripted communication to be provided by the communication system or the care team member to continue the communication (step 1538). The operation then returns to step 1522. Otherwise, if the communication session has been terminated, the operation ends with regard to the communication session but may be repeated with regard to other communication sessions that may be managed by the mobile application of the care team member communication system.

Thus, the illustrative embodiments provide a method, computer program product, and apparatus that implements a personalized health care management system that operates to receive a personalized health care plan for a patient and dynamic patient monitoring data from one or more patient monitoring devices associated with the patient. The personalized health care management system analyzes the dynamic patient monitoring data to identify at least one pattern of dynamic patient monitoring data representing a habit of the patient. The personalized health care management system generates desired pattern data based on results of the analysis. The desired pattern data represents at least one desired habit for the patient. The personalized health care management system determines at least one communication to output to the patient via a patient computing device or patient communication device to elicit conformance of the patient with the at least one desired habit based on the generated desired pattern data and the personalized health care plan, and outputting, by the personalized health care management system, the at least one communication to the patient computing device or patient communication device.

In some illustrative embodiments, the personalized health care plan comprises at least one health goal of the patient, and the desired pattern data is generated based on an analysis of the at least one pattern of dynamic patient monitoring data and the at least one health goal of the patient. With some illustrative embodiments, analyzing the dynamic patient monitoring data to identify at least one pattern of dynamic patient monitoring data representing a habit of the patient comprises correlating the dynamic patient monitoring data with patient lifestyle information to identify a cause for a deviation of the dynamic patient monitoring data from expected patient monitoring data corresponding to the personalized health care plan for the patient. In still further illustrative embodiments, the patient lifestyle information comprises at least one of first patient lifestyle information defining activity performed by the patient over a specified period of time or second patient lifestyle information defining consumption by the patient over a specified period of time.

With some illustrative embodiments, the personalized health care management system continuously receives dynamic patient monitoring data over a specified period of time and performs the analyze, generate, determine, and output operations in response to receiving new dynamic patient monitoring data during the specified period of time. Moreover, in some illustrative embodiments, determining at least one communication to output comprises determining a difference between the desired pattern data and the at least one pattern of dynamic patient monitoring data, and determining a communication to be output to the patient that is directed to minimizing the difference between the desired pattern data and the at least one pattern of dynamic patient monitoring data.

In some illustrative embodiments, the at least one communication is a pre-defined scripted communication associated with the at least one health goal and the at least one desired habit. Furthermore, in some illustrative embodiments, the at least one communication is an ad hoc communication between the patient and a human patient care manager.

With some illustrative embodiments, the personalized health care management system further operates to determine at least one second communication to output to a care plan manager computing device associated with a human patient care manager associated with the patient. The at least one second communication provides instructions to the human patient care manager to facilitate interaction between the human patient care manager and the patient that will elicit conformance of the patient with the at least one desired habit. Furthermore, the personalized health care management system outputs the at least one second communication to the care plan manager computing device. In yet some illustrative embodiments, determining at least one second communication to output further comprises determining a type of difference between the desired pattern data and the at least one pattern of dynamic patient monitoring data, and identifying a care plan manager associated with the patient whose specialization or responsibilities are directed to the type of difference, wherein the at least one second communication is output to the identified care plan manager.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, wherein the at least one memory comprises instructions which are executed by the at least one processor to configure the data processing system to implement a personalized health care management system that operates to perform the method, wherein the method comprises:

receiving, by the personalized health care management system, a personalized health care plan for a patient, wherein the personalized health care plan comprises at least one health goal of the patient;

receiving, by the personalized health care management system, dynamic patient monitoring data from one or more patient monitoring devices associated with the patient;

analyzing, by the personalized health care management system, the dynamic patient monitoring data to determine at least one first communication to output to the patient containing content eliciting conformance of the patient with the personalized health care plan to achieve the at least one health goal;

sending, by the personalized health care management system, to a patient care manager computing device of a patient care manager associated with the patient, a second communication based on results of analyzing the dynamic patient monitoring data;

initiating or continuing, by the patient care manager computing device, a communication session between the patient care manager computing device and a patient communication device associated with the patient, the second communication causing the patient care manager computing device to automatically send a scripted communication corresponding to the at least one first communication to the patient communication device via the communication session;

outputting, on a first mobile application executing on the patient care manager computing device, an interface for managing a plurality of communication sessions with a plurality of patients; and providing, via the first mobile application executing on the patient care manager computing device, an alert output indicating a need for a patient care manager's attention to a communication session associated with the patient in response to results of the analysis.

2. The method of claim 1, wherein the personalized health care management system continuously receives dynamic patient monitoring data over a specified period of time and performs the analyze and send operations in response to receiving new dynamic patient monitoring data during the specified period of time.

3. The method of claim 1, wherein the analysis to determine at least one first communication to output comprises:

determining a difference between a desired pattern of patient monitoring data and the at least one pattern of dynamic patient monitoring data; and determining a communication to be output that is directed to minimizing the difference between the desired pattern of patient monitoring data and the at least one pattern of dynamic patient monitoring data.

4. The method of claim 1, wherein analyzing the dynamic patient monitoring data to determine at least one first communication to output to the patient comprises determining a medical condition of the patient, determining a measure of adherence of the patient to an associated patient personalized care plan, determining goals of the associating patient personalized care plan, and determining patient lifestyle information for the patient.

5. The method of claim 4, wherein the at least one first communication comprises content that is specifically customized to the medical condition, measure of adherence, goals, and patient lifestyle information.

6. The method of claim 1, wherein the second communication initiates the new communication session, or continues the existing communication session, between the patient care manager computing device and a patient communication device associated with the patient at least by causing the first mobile application executing on the patient care manager computing device to communicate with a corresponding second mobile application executing on the patient communication device.

7. The method of claim 1, wherein the second communication causes the first mobile application executing on the patient care manager computing device to automatically send a scripted communication corresponding to the at least one first communication to a second mobile application executing on the patient communication device.

8. The method of claim 7, wherein the scripted communication is sent from the first mobile application to the second mobile application in response to expiration of a time period since a last communication having been received by the first mobile application from the second mobile application.

9. The method of claim 1, wherein the interface comprises selectable elements for selecting a pre-defined scripted communication, from a plurality of pre-defined scripted communications, to send to the patient communication device, and wherein the plurality of pre-defined scripted communications is a subset, specific to an area of responsibility of the patient care manager, of a set of pre-defined scripted communications.

10. A computer program product comprising a non-transitory computer readable medium having a computer readable program stored therein, wherein the computer readable program, when executed on a computing device, causes the computing device to implement a personalized health care management system that operates to:

receive a personalized health care plan for a patient, wherein the personalized health care plan comprises at least one health goal of the patient;

receive dynamic patient monitoring data from one or more patient monitoring devices associated with the patient;

analyze the dynamic patient monitoring data to determine at least one first communication to output to the patient containing content eliciting conformance of the patient with the personalized health care plan to achieve the at least one health goal;

send, to a patient care manager computing device of a patient care manager associated with the patient, a second communication based on results of analyzing the dynamic patient monitoring data;

initiate or continue, by the patient care manager computing device, a communication session between the patient care manager computing device and a patient communication device associated with the patient, the second communication causing the patient care manager computing device to automatically send a scripted communication corresponding to the at least one first communication to the patient communication device;

output, on a first mobile application executing on the patient care manager computing device, an interface for a plurality of communication sessions with a plurality of patients; and provide, via the first mobile application executing on the patient care manager computing device, an alert output indicating a need for a patient care manager's attention to a communication session associated with the patient in response to results of the analysis.

11. The computer program product of claim 10, wherein the personalized health care management system continuously receives dynamic patient monitoring data over a specified period of time and performs the analyze and send operations in response to receiving new dynamic patient monitoring data during the specified period of time.

12. The computer program product of claim 10, wherein the analysis to determine at least one first communication to output comprises:

determining a difference between a desired pattern of patient monitoring data and the at least one pattern of dynamic patient monitoring data; and determining a communication to be output that is directed to minimizing the difference between the desired pattern of patient monitoring data and the at least one pattern of dynamic patient monitoring data.

13. The computer program product of claim 10, wherein the computer readable program further causes the computing device to analyze the dynamic patient monitoring data to determine at least one first communication to output to the patient at least by determining a medical condition of the patient, determining a measure of adherence of the patient to an associated patient personalized care plan, determining goals of the associating patient personalized care plan, and determining patient lifestyle information for the patient.

14. The computer program product of claim 13, wherein the at least one first communication comprises content that is specifically customized to the medical condition, measure of adherence, goals, and patient lifestyle information.

15. The computer program product of claim 10, wherein the second communication initiates the new communication session, or continues the existing communication session, between the patient care manager computing device and a patient communication device associated with the patient at least by causing the first mobile application executing on the patient care manager computing device to communicate with a corresponding second mobile application executing on the patient communication device.

16. The computer program product of claim 10, wherein the second communication causes the first mobile application executing on the patient care manager computing device to automatically send a scripted communication corresponding to the at least one first communication to a second mobile application executing on the patient communication device.

17. The computer program product of claim 16, wherein the scripted communication is sent from the first mobile application to the second mobile application in response to expiration of a time period since a last communication having been received by the first mobile application from the second mobile application.

18. The computer program product of claim 10, wherein the interface comprises selectable elements for selecting a pre-defined scripted communication, from a plurality of pre-defined scripted communications, to send to the patient communication device, and wherein the plurality of pre-defined scripted communications is a subset, specific to an area of responsibility of the patient care manager, of a set of pre-defined scripted communications.

19. An apparatus comprising:

a processor; and a memory coupled to the processor, wherein the memory comprises instructions which, when executed by the processor, cause the processor to:

receive a personalized health care plan for a patient, wherein the personalized health care plan comprises at least one health goal of the patient;

receive dynamic patient monitoring data from one or more patient monitoring devices associated with the patient;

analyze the dynamic patient monitoring data to determine at least one first communication to output to the patient containing content eliciting conformance of the patient with the personalized health care plan to achieve the at least one health goal; and send, to a patient care manager computing device of a patient care manager associated with the patient, a second communication based on results of analyzing the dynamic patient monitoring data;

initiate or continue, by the patient care manager computing device, a communication session between the patient care manager computing device and a patient communication device associated with the patient, the second communication causing the patient care manager computing device to automatically send a scripted communication corresponding to the at least one first communication to the patient communication device;

output, on a first mobile application executing on the patient care manager computing device, an interface for managing a plurality of communication sessions with a plurality of patients; and provide, via the first mobile application executing on the patient care manager computing device an alert output indicating a need for a patient care manager's attention to a communication session associated with the patient in response to results of the analysis.

20. The apparatus of claim 19, wherein the interface comprises selectable elements for selecting a pre-defined scripted communication, from a plurality of pre-defined scripted communications, to send to the patient communication device, and wherein the plurality of pre-defined scripted communications is a subset, specific to an area of responsibility of the patient care manager, of a set of pre-defined scripted communications.

* * * * *